United States Patent
Solan et al.

(10) Patent No.: US 7,423,101 B2
(45) Date of Patent: Sep. 9, 2008

(54) CATALYST COMPOSITION AND USE THEREOF

(75) Inventors: Gregory A. Solan, Leicestershire (GB); Christopher J. Davies, Manchester (GB)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/943,163

(22) Filed: Nov. 20, 2007

(65) Prior Publication Data

US 2008/0071047 A1 Mar. 20, 2008

Related U.S. Application Data

(62) Division of application No. 11/042,217, filed on Jan. 25, 2005, now Pat. No. 7,317,057.

(60) Provisional application No. 60/553,839, filed on Mar. 17, 2004.

(51) Int. Cl.
C08F 4/06 (2006.01)
(52) U.S. Cl. ........................ 526/172; 526/175; 526/169; 526/161; 502/103; 502/155; 502/167; 556/1; 556/45; 556/138
(58) Field of Classification Search ................ 526/161, 526/172, 175, 169; 502/103, 155, 167; 556/1, 556/45, 138
See application file for complete search history.

(56) References Cited

U.S. PATENT DOCUMENTS 3,661,898 A 5/1972 Dehnert et al. .......... 260/240 G

FOREIGN PATENT DOCUMENTS

| WO | 00/20427 | | 4/2000 |
|---|---|---|---|
| WO | WO 00/20427 | * | 4/2000 |
| WO | 01/10875 | | 2/2001 |
| WO | 03/054038 | | 7/2003 |
| WO | 2004/007509 | | 1/2004 |

OTHER PUBLICATIONS

Fernandes et al., "Polymerisation of ethylene catalysed by mono-imine-2,6-diacetylpyridine iron/methylaluminoxane (MAO) catalyst system: effect of the ligand on polymer microstructure", Polymer International, 2002, vol. 51, pp. 1301-1303.
Luks et al., "The Template Synthesis and Characterization of New Mono- and Dinuclear Podand Schiff Base Complexes of Scandium Group Elements", Collect. Czech. Chem. Commun, 1998, vol. 63, pp. 371-377.
Pritchard et al., "Isolation of ternary complex precursors and partially condensed intermediates to macrocyclic complexes of nickel(II) and copper(II)", Transition Metal Chemistry (London), 1998, vol. 23, pp. 609-613.
Gebbink et al., "Oxidatively Robust Monophenolate-Copper(II) Complexes as Potential Models of Galactose Oxidase", Chem. Commun, 2003, pp. 630-631.
Bardwell et al., "The Coordination Chemistry of Mixed Pyridine-Phenol and Phenanthroline-Phenol Ligands; Synthesis and Crystal Structure of [PdL$^1$Cl] (CH$_2$Cl$_2$) [HL$^1$=6-(2-Hydroxyphenyl)-2,2'-Bipyridine]", Polyhedron, vol. 12, No. 13, pp. 1577-1580, 1993.
Jensen et al., "Biomimetic Aryl Hydroxylation Derived from Alkyl Hydroperoxide at a Nonheme Iron Center. Evidence for an Fe$^{IV}$=O Oxidant", J. Am. Chem. Soc. 2003, vol. 125, pp. 2113-2128.

* cited by examiner

*Primary Examiner*—Robert D. Harlan
(74) *Attorney, Agent, or Firm*—Catherine L. Bell

(57) ABSTRACT

The present invention is directed toward Group 4, 5, 6, 7, 8, 9, 10 or 11 transition metal compounds containing neutral, mono- or di-anionic tridentate nitrogen/oxygen based ligands that are useful, with or without activators, to polymerize olefins, particularly α-olefins, or other unsaturated monomers. For the purposes of this disclosure, "α-olefins" includes ethylene. The present invention is also directed toward Group 4, 5, 6, 7, 8, 9, 10 or 11 transition metal compounds containing neutral, bidentate nitrogen/oxygen based ligands that are useful to polymerize olefins, particularly α-olefins, or other unsaturated monomers.

37 Claims, 3 Drawing Sheets

CATALYST COMPOSITION AND USE THEREOF

This application is a divisional of U.S. Ser. No. 11/042,217 (allowed), filed Jan. 25, 2005 now U.S. Pat. No. 7,317,057, which claims the benefit of U.S. Patent Application 60/553,839 filed Mar. 17, 2004.

FIELD OF THE INVENTION

This invention relates to catalyst compounds useful for polymerization and or oligomerization of unsaturated monomers, such as olefins.

BACKGROUND OF THE INVENTION

As is well known, various processes and catalysts exist for the homopolymerization or copolymerization of olefins.

New polymerization catalysts are of great interest in the industry because they offer many new opportunities for providing new processes and products to the markets in a cheaper and more efficient manner. The following invention relates to new polymerization technology based upon new late transition metal catalyst compounds.

References of general interest related to the instant invention include:

WO 2000/020427; WO 2001/010875; WO 2003/054038; Polymer International, (2002) 51 (12), 1301-1303; Collection of Czechoslovak Chemical Communications (1988), 63(3), 371-377; and Transition Metal Chemistry (London) (1988) 23 (5), 609-613.

SUMMARY OF THE INVENTION

The present invention is directed toward Group 4, 5, 6, 7, 8, 9, 10 or 11 transition metal compounds containing neutral, mono- or di-anionic tridentate nitrogen/oxygen based ligands that are useful, with or without activators, to polymerize olefins, particularly α-olefins, or other unsaturated monomers. For the purposes of this disclosure, "α-olefins" includes ethylene.

The present invention is also directed toward Group 4, 5, 6, 7, 8, 9, 10 or 11 transition metal compounds containing neutral, bidentate nitrogen/oxygen based ligands that are useful, with or without activators, to polymerize olefins, particularly α-olefins, or other unsaturated monomers.

The oligomerization or polymerization compositions of this invention preferably comprise transition metal compounds of formula: $[LMX_w]_z$ wherein w is 1, 2 or 3;

z is 1 or 2;

each M is, independently, a Group 4 to 11 metal, preferably a Group 4, 7, 8, 9, or 10 metal;

each L is, independently, a neutral, mono- or di-anionic tridentate ligand that is bonded to M by two nitrogen atoms and one oxygen atom, (where one of the nitrogen atoms and the oxygen atom are terminal atoms and the other nitrogen atom is a central atom), and the central nitrogen atom is part of a pyridinyl ring, and the central nitrogen atom is connected to the terminal oxygen atom at one ortho position of the pyridinyl ring via a group having at least two carbon atoms, and the central nitrogen atom is connected to the terminal nitrogen atom at the other ortho position of the pyridinyl ring via a group having at least one carbon atom (preferably at least two carbon atoms), and the terminal nitrogen atom is substituted with one $C_3$-$C_{50}$ hydrocarbyl or one hydrogen or substituted with one $C_3$-$C_{50}$ hydrocarbyl and one hydrogen atom or two hydrocarbyls wherein at least one hydrocarbyl is a $C_3$-$C_{50}$ hydrocarbyl, and the terminal oxygen atom is bonded to two different carbon atoms or one carbon atom and one hydrogen atom to give a neutral donor or one carbon atom to form a mono-anionic donor; and X is independently a monoanionic ligand.

The oligomerization or polymerization compositions of this invention also preferably comprises transition metal compounds of formula: $[LMX_w]_z$ wherein w is 1, 2 or 3;

z is 1 or 2;

each M is, independently, a Group 4 to 11 metal, preferably a Group 4, 7, 8, 9, or 10 metal;

each L is, independently, a neutral bidentate ligand that is bonded to M by two nitrogen atoms, (where one of the nitrogen atoms is a terminal atom and the other nitrogen atom is a central atom), and the central nitrogen atom is part of a pyridinyl ring and the central nitrogen atom is connected to the terminal nitrogen atom at one ortho position of the pyridinyl ring via a group having at least one carbon atom (preferably at least two carbon atoms), and the other ortho position of the pyridyl ring is substituted with a group represented by the formula —CR═CR—O—R, wherein each R is independently a C1 to C12 alkyl group, and the terminal nitrogen atom is substituted with one $C_3$-$C_{50}$ hydrocarbyl or one hydrogen or substituted with one $C_3$-$C_{50}$ hydrocarbyl and one hydrogen atom or two hydrocarbyls wherein at least one hydrocarbyl is a $C_3$-$C_{50}$ hydrocarbyl; and X is independently a monoanionic ligand.

This invention further relates to transition metal compounds represented by formulae 1 to 6.

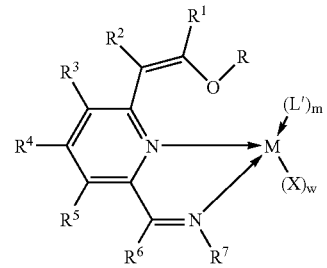

Formula 1

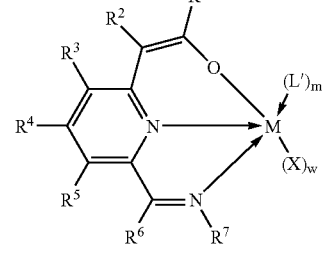

Formula 2

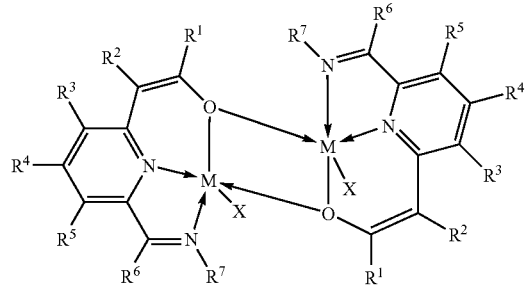

Formula 3

-continued

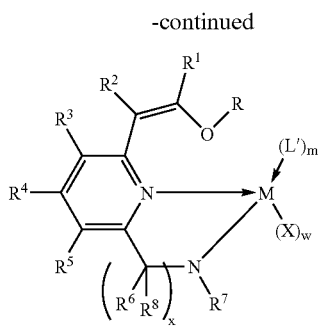

Formula 4

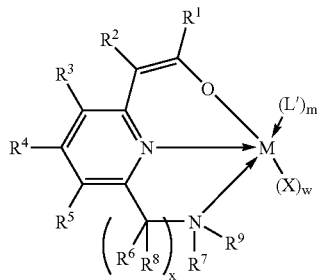

Formula 5 wherein
each M is, independently, a group 4, 5, 6, 7, 8, 9, 10, or 11 transition metal;
N is nitrogen;
O is oxygen;
each X is, independently, an anionic monodentate ligand;
w is 1, 2 or 3;
each R is, independently, a hydrogen, a hydrocarbyl, a substituted hydrocarbyl, a halocarbyl, or a substituted halocarbyl;
each $R^1$ and $R^2$ is, independently, a hydrogen, a hydrocarbyl, a substituted hydrocarbyl, a halocarbyl, or a substituted halocarbyl, or independently, may join together to form a cyclic or polycyclic ring structure;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl, a halocarbyl, or a substituted halocarbyl;
each $R^8$ is, independently, a hydrogen, a $C_3$ to $C_{50}$ hydrocarbyl or a $C_3$ to $C_{50}$ halocarbyl;
each x is, independently, 1, 2, 3 or 4;
each $R^9$ is, independently, a hydrocarbyl, a substituted hydrocarbyl, a halocarbyl, or a substituted halocarbyl;
and L' is a neutral ligand bonded to M, and
m is 0, 1 or 2.

Formula 6

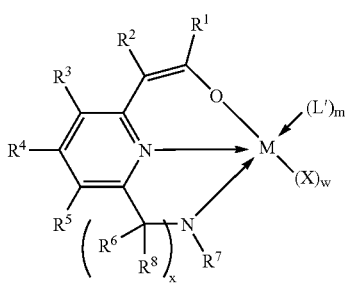

wherein
each M is, independently, a group 4, 5 or 6 transition metal;
N is nitrogen;
O is oxygen;
each X is, independently, an anionic monodentate ligand,
w is 1, 2, or 3;
each R is, independently, a hydrogen, a hydrocarbyl, a substituted hydrocarbyl, a halocarbyl, or a substituted halocarbyl;
each $R^1$ and $R^2$ is, independently, a hydrogen, a hydrocarbyl, a substituted hydrocarbyl, a halocarbyl, or a substituted halocarbyl, or independently, may join together to form a cyclic or polycyclic ring structure;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl, a halocarbyl, or a substituted halocarbyl;
each $R^8$ is, independently, a hydrogen, a $C_3$ to $C_{50}$ hydrocarbyl or a $C_3$ to $C_{50}$ halocarbyl;
each x is, independently, 1, 2, 3 or 4;
and L' is a neutral ligand bonded to M, and
m is 0, 1 or 2.

In the formulae depicted throughout this specification and the claims, a solid line indicates a bond, and an arrow indicates that the bond may be dative.

This invention further relates to a process to oligomerize or polymerize an unsaturated monomer using the compositions described herein.

BRIEF DESCRIPTION OF DRAWINGS

FIG. 1 is a drawing of the molecular structure of compound 4a.
FIG. 2 is a drawing of the molecular structure of compound 5a.
FIG. 4 is a drawing of the molecular structure of compound 8a.

DEFINITIONS

Figure 1:
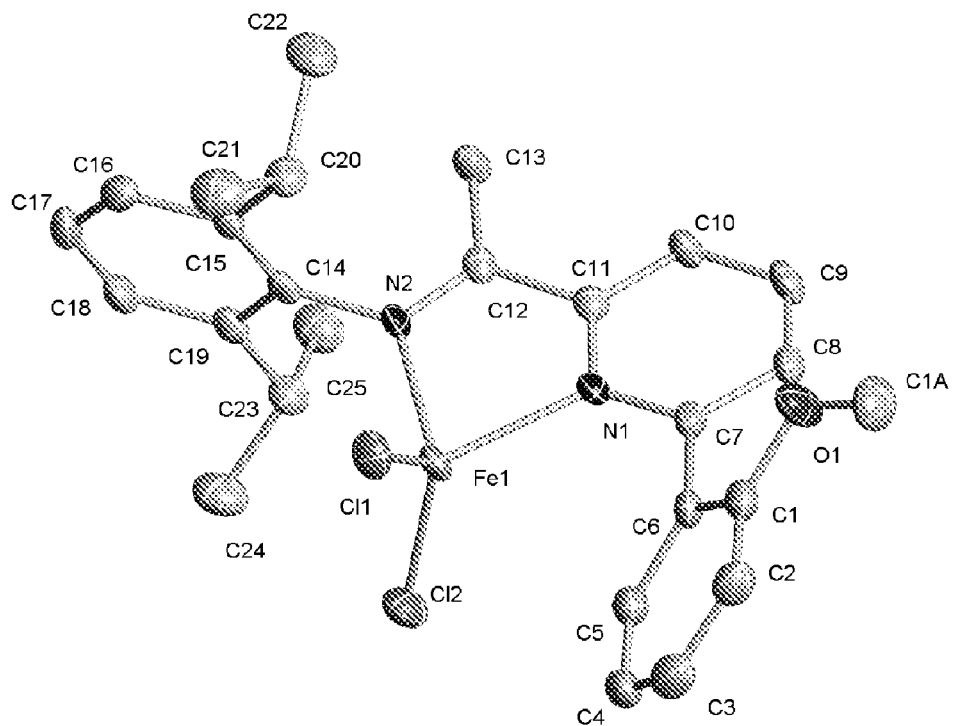

As used herein, the new notation for the Periodic Table Groups is used as described in CHEMICAL AND ENGINEERING NEWS, 63(5), 27 (1985).

Neutral ligands are defined as ligands that are neutral, with respect to charge, when formally removed from the metal in their closed shell electronic state. Neutral ligands contain at least one lone pair of electrons, pi-bond or sigma bond that are capable of binding to the transition metal. Neutral ligands may also be polydentate when more than one Neutral ligand is connected via a bond or a hydrocarbyl, substituted hydrocarbyl or a functional group tether. A Neutral ligand may be a substituent of another metal complex, either the same or different, such that multiple complexes are bound together.

Anionic ligands are defined as ligands that are anionic, with respect to charge, when formally removed from the metal in their closed shell electronic state. Anionic ligands include hydride, halide, hydrocarbyl, substituted hydrocarbyl or functional group. Non-limiting examples of anionic ligands include hydride, fluoride, chloride, bromide, iodide, alkyl, aryl, alkenyl, alkynyl, allyl, benzyl, acyl, trimethylsilyl. Anionic ligands may also be polydentate when more than one anionic ligand is connected via a bond or a hydrocarbyl, substituted hydrocarbyl or a functional group tether. An anionic ligand may be a substituent of another metal complex, either the same or different, such that multiple complexes are bound together. A mono-anionic ligand is defined to be an anionic ligand that has a −1 charge. A di-anionic ligand is defined to be an anionic ligand that has a −2 charge.

The terms "hydrocarbyl radical," "hydrocarbyl" and hydrocarbyl group" are used interchangeably throughout this document. Likewise the terms "group" and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$ and the like or where at least one non-hydrocarbon atom or group has been inserted within the hydrocarbyl radical, such as O, S, Se, Te, $NR*$, $PR*$, $AsR*$, $SbR*$, $BR*$, $SiR*_2$, $GeR*_2$, $SnR*_2$, $PbR*_2$ and the like, where $R*$ is independently a hydrocarbyl or halocarbyl radical.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$ and the like or where at least one non-carbon atom or group has been inserted within the halocarbyl radical such as O, S, Se, Te, $NR*$, $PR*$, $AsR*$, $SbR*$, $BR*$, $SiR*_2$, $GeR*_2$, $SnR*_2$, $PbR*_2$ and the like where $R*$ is independently a hydrocarbyl or halocarbyl radical provided that at least one halogen atom remains on the original halocarbyl radical.

Silylcarbyl radicals (also called silylcarbyls) are groups in which the silyl functionality is bonded directly to the indicated atom or atoms. Examples include $SiH_3$, $SiH_2R*$, $SiHR*_2$, $SiR*_3$, $SiH_2(OR*)$, $SiH(OR*)_2$, $Si(OR*)_3$, $SiH_2(NR*_2)$, $SiH(NR*_2)_2$, $Si(NR*_2)_3$, and the like where $R*$ is independently a hydrocarbyl or halocarbyl radical as defined above and two or more $R*$ may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R*$, $GeHR*_2$, $GeR^5_3$, $GeH_2(OR*)$, $GeH(OR*)_2$, $Ge(OR*)_3$, $GeH_2(NR*_2)$, $GeH(NR*_2)_2$, $Ge(NR*_2)_3$, and the like where $R*$ is independently a hydrocarbyl or halocarbyl radical as defined above and two or more $R*$ may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR*_2$, $OR*$, $SeR*$, $TeR*$, $PR*_2$, $AsR*_2$, $SbR*_2$, $SR*$, $BR*_2$, $SnR*_3$, $PbR*_3$ and the like where $R*$ is independently a hydrocarbyl, substituted hydrocarbyl, halocarbyl or substituted halocarbyl radical as defined above and two $R*$ may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

In the context of this document, "homopolymerization" would produce a polymer made from one monomer. For example, homopolymerization of propylene would produce homopolypropylene, also called polypropylene. Homopolymerization of ethylene would produce homopolyethylene, also called polyethylene. It should be noted, however, that some of the catalysts of this invention homopolymerize ethylene or propylene to non-traditional "polyethylene" and "polypropylene" structures, respectively. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and -silicon atoms such as for example B, O, S, Se, Te, N, P, Ge, Sn, Pb, As, F, Cl, Br, or I, are contemplated, where such non-carbon or -silicon moieties are sufficiently far removed from the double bond so as not to interfere with the coordination polymerization reaction with the catalyst and so to retain the generally hydrocarbyl characteristic. By being sufficiently far removed from the double bond we intend that the number of carbon atoms, or the number of carbon and silicon atoms, separating the double bond and the non-carbon or -silicon moiety may be 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or -silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. All documents cited herein are incorporated by reference for purposes of all jurisdictions where such practice is allowed. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

The terms "catalyst" and "catalyst compound" are defined to mean a compound capable of initiating catalysis. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. The term "catalyst system" is defined to mean: 1) a catalyst precursor/activator pair, and or 2) a catalyst compound capable of initiating catalysis without an activator. When "catalyst system" is used to describe such a pair before activation, it means the unactivated catalyst (pre-catalyst) together with an activator and, optionally, a co-activator. When it is used to describe such a pair after activation, it means the activated catalyst and the activator or other charge-balancing moiety.

The catalyst compound may be neutral as in a pre-catalyst or a catalyst system not requiring an activator, or may be a charged species with a counter ion as in an activated catalyst system.

The terms "activator" and "cocatalyst" are used interchangeably herein. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

For purposes of this invention and the claims thereto, in describing a ligand, a terminal nitrogen atom, is a nitrogen atom that is indirectly bonded to only one other nitrogen atom. A central nitrogen atom is a nitrogen atom that is indirectly bonded to at least one other nitrogen atom and at least one oxygen atom. A terminal oxygen atom is an oxygen atom that is indirectly bonded to only the central nitrogen atom. An example is illustrated below:

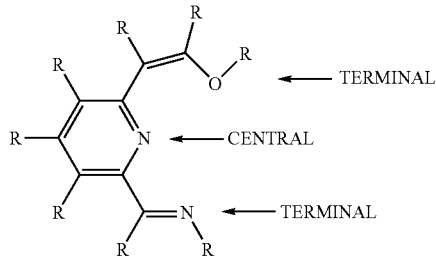

DETAILED DESCRIPTION OF THE INVENTION

This invention further relates to transition metal compounds represented by formulae 1 to 5 and 7 to 11.

Formula 1

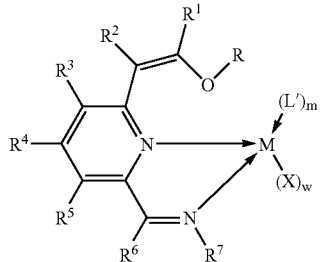

Formula 2

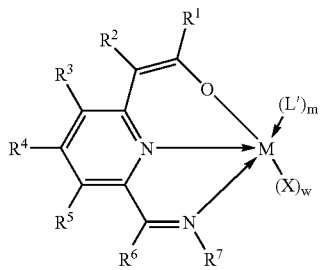

Formula 3

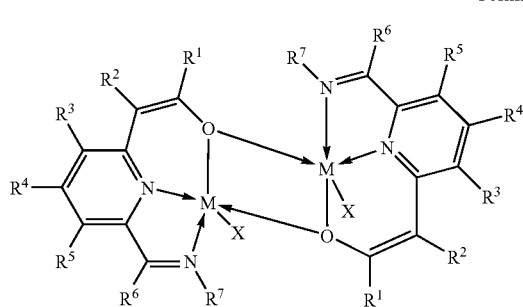

-continued

Formula 4

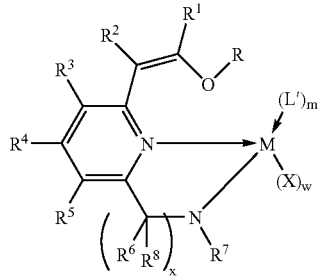

Formula 5

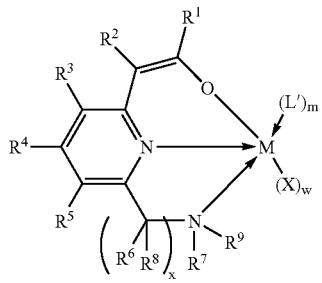

Formula 7

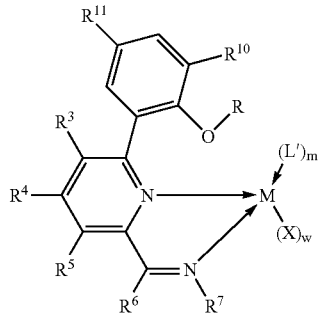

Formula 8

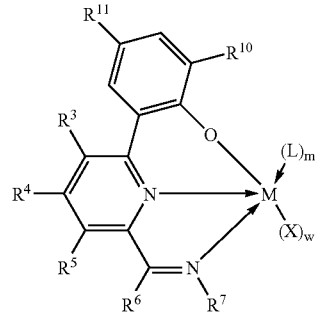

-continued

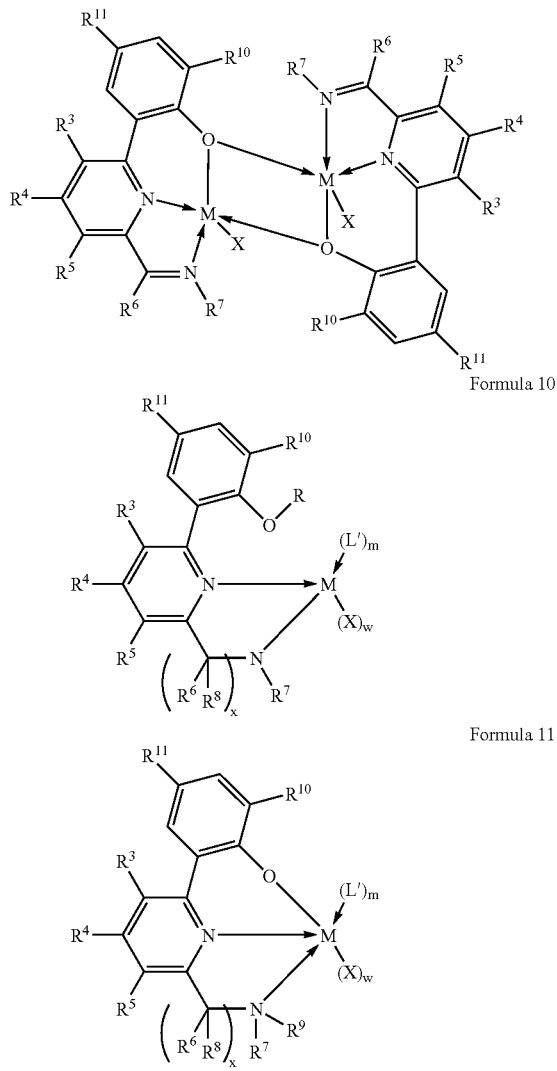

Formula 9

Formula 10

Formula 11 wherein
each M is, independently, a group 4, 5, 6, 7, 8, 9, 10, or 11 transition metal, preferably a group 6, 7, 8, 9 or 10 transition metal, preferably chromium, manganese, iron, cobalt or nickel;
N is nitrogen;
O is oxygen;
w is 1, 2, or 3;
each X is, independently, a hydride, a halogen, a hydrocarbyl, a substituted hydrocarbyl, a halocarbyl, or a substituted halocarbyl;
additionally, X may independently be selected from halogen, alkoxide, aryloxide, amide, phosphide, or other anionic ligand when Lewis-acid activators (such as methylalumoxane, aluminum alkyls, alkylaluminum alkoxides) or alkylaluminum halides (capable of donating a hydride, hydrocarbyl, substituted hydrocarbyl, halocarbyl or substituted halocarbyl X ligand to the transition metal component) are used, or when an ionic activator is capable of extracting X, provided that the resulting activated catalyst contains as least one M—H or M—C bond into which an olefin can insert;
each R is, independently, hydrogen, or a hydrocarbyl, a substituted hydrocarbyl, a halocarbyl, a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;
each $R^1$ and $R^2$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or independently, may join together to form a $C_4$ to $C_{62}$ cyclic or polycyclic ring structure;
each $R^3$, $R^4$, $R^5$, is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or independently, may join together to form a $C_4$ to $C_{62}$ cyclic or polycyclic ring structure;
each $R^6$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;
each $R^7$ and $R^9$ is, independently, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;
each $R^8$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;
each $R^{10}$ is, independently, a hydrocarbyl, a substituted hydrocarbyl, a halocarbyl, or a substituted halocarbyl;
each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group; and
each x is, independently, 1, 2, 3 or 4, preferably, x is 1;
L' is a neutral ligand bonded to M that may include molecules such as but not limited to acetonitrile, diethyl ether, tetrahydrofuran, dimethylaniline, trimethylamine, tributylamine, trimethylphosphine, triphenylphosphine lithium chloride, ethylene, propylene, butene, octene, styrene, and the like; and
m is 0, 1 or 2 and indicates the absence or presence of L'.

In a preferred embodiment the halocarbyls are fluorocarbyls and the substituted halocarbyls are substituted fluorocarbyls.

To illustrate members of the transition metal catalyst compounds useful in this invention, select any combination of the species listed in Table 1.

| R', R¹, R², R³, R⁴, R⁵, R⁶, R¹⁰, R¹¹ | R⁷ | X | M | L' |
|---|---|---|---|---|
| hydrogen | propyl | chloride | vanadium | acetonitrile |
| methyl | butyl | bromide | chromium | diethyl ether |
| ethyl | pentyl | iodide | cobalt | tetrahydrofuran |
| propyl | hexyl | methyl | manganese | furan |
| butyl | heptyl | ethyl | iron | thiofuran |
| pentyl | octyl | propyl | nickel | chromane |
| hexyl | nonyl | butyl | copper | isochromane |
| heptyl | decyl | pentyl | niobium | thiochromane |
| octyl | undecyl | hexyl | tantalum | thioisochromane |
| nonyl | dodecyl | heptyl | molybdenum | quinuclidine |
| decyl | tridecyl | octyl | tungsten | benzofuran |
| undecyl | tetradecyl | nonyl | technetium | chromene |
| dodecyl | octacosyl | decyl | rhenium | isobenzofuran |
| tridecyl | nonacosyl | undecyl | ruthenium | isoquinoline |
| tetradecyl | triacontyl | dodecyl | osmium | oxazole |
| octacosyl | cyclohexyl | tridecyl | rhodium | phenanthridine |
| nonacosyl | cyclopentyl | tetradecyl | iridium | pyran |
| triacontyl | cycloheptyl | pentadecyl | palladium | pyridine |
| cyclohexyl | cyclooctyl | hexadecyl | platinum | quinoline |
| cyclopentyl | cyclodecyl | heptadecyl | silver | selenophene |
| cycloheptyl | cyclododecyl | octadecyl | gold | thiophene |
| cyclooctyl | naphthyl | nonadecyl | | trimethylamine |
| cyclodecyl | phenyl | eicosyl | | triethylamine |
| cyclododecyl | tolyl | heneicosyl | | tributylamine |
| naphthyl | benzyl | docosyl | | dimethylaniline |
| phenyl | phenethyl | tricosyl | | trimethylphosphine |
| tolyl | dimethylphenyl | tetracosyl | | triphenylphosphine |
| benzyl | trimethylphenyl | pentacosyl | | ethylene |
| phenethyl | methylphenyl | hexacosyl | | propylene |
| dimethylphenyl | ethylphenyl | heptacosyl | | butene |
| diethylphenyl | diethylphenyl | octacosyl | | hexene |
| anthracenyl | triethylphenyl | nonacosyl | | octene |
| adamantyl | propylphenyl | triacontyl | | cyclohexene |
| norbornyl | dipropylphenyl | hydride | | vinylcyclohexene |
| CF₃ | tripropylphenyl | phenyl | | benzene |
| NO₂ | Methylethylphenyl | benzyl | | styrene |
| t-butyl | dibutylphenyl | phenethyl | | methylstyrene |
| i-propyl | butylphenyl | tolyl | | |
| naphthyl | | methoxy | | |
| fluoride | | ethoxy | | |
| | | propoxy | | |
| | | butoxy | | |
| | | dimethylamido | | |
| | | diethylamido | | |
| | | methylethylamido | | |
| | | phenoxy | | |
| | | benzoxy | | |
| | | allyl | | |

A selection of catalyst precursors are detailed below. These are by way of an example only and are not intended to list every catalyst precursor that is within the scope of the invention:

[2-acetyl(2,6-diisopropylanil)-6-phenyl(2'-methoxy)-pyridine]iron dichloride
[2-acetyl(2,6-diisopropylanil)-6-phenyl(2'-methoxy)-pyridine]cobalt dichloride
[2-acetyl(2,6-diisopropylanil)-6-phenyl(2'-methoxy)-pyridine]nickel dichloride
[2-acetyl(2,6-diisopropylanil)-6-phenyl(2'-methoxy)-pyridine]copper dichloride
[2-acetyl(2,4,6-trimethylanil)-6-phenyl(2'-methoxy)-pyridine]iron dichloride
[2-acetyl(2,4,6-trimethylanil)-6-phenyl(2'-methoxy)-pyridine]cobalt dichloride
[2-acetyl(2,4,6-trimethylanil)-6-phenyl(2'-methoxy)-pyridine]nickel dichloride
[2-acetyl(2,4,6-trimethylanil)-6-phenyl(2'-methoxy)-pyridine]copper dichloride
[2-acetyl(2,3,4,5,6-pentafluoroanil)-6-phenyl(2'-methoxy)-pyridine]iron dichloride
[2-acetyl(2,3,4,5,6-pentafluoroanil)-6-phenyl(2'-methoxy)-pyridine]cobalt dichloride
[2-acetyl(2,3,4,5,6-pentafluoroanil)-6-phenyl(2'-methoxy)-pyridine]nickel dichloride
[2-acetyl(2,3,4,5,6-pentafluoroanil)-6-phenyl(2'-methoxy)-pyridine]copper dichloride
[2-acetyl(2,6-diisopropylanil)-6-phenyl(2'-methoxy,3'-phenyl)-pyridine]iron dichloride
[2-acetyl(2,6-diisopropylanil)-6-phenyl(2'-methoxy,3'-phenyl)-pyridine]cobalt dichloride
[2-acetyl(2,6-diisopropylanil)-6-phenyl(2'-methoxy,3'-phenyl)-pyridine]nickel dichloride
[2-acetyl(2,6-diisopropylanil)-6-phenyl(2'-methoxy,3'-phenyl)-pyridine]copper dichloride
[2-acetyl(2,4,6-trimethylanil)-6-phenyl(2'-methoxy,3'-phenyl)-pyridine]iron dichloride
[2-acetyl(2,4,6-trimethylanil)-6-phenyl(2'-methoxy,3'-phenyl)-pyridine]cobalt dichloride

[2-acetyl(2,4,6-trimethylanil)-6-phenyl(2'-methoxy,3'-phenyl)-pyridine]nickel dichloride
[2-acetyl(2,4,6-trimethylanil)-6-phenyl(2'-methoxy,3'-phenyl)-pyridine]copper dichloride
[2-acetyl(2,3,4,5,6-pentafluoroanil)-6-phenyl(2'-methoxy,3'-phenyl)-pyridine]iron dichloride
[2-acetyl(2,3,4,5,6-pentafluoroanil)-6-phenyl(2'-methoxy,3'-phenyl)-pyridine]cobalt dichloride
[2-acetyl(2,3,4,5,6-pentafluoroanil)-6-phenyl(2'-methoxy,3'-phenyl)-pyridine]nickel dichloride
[2-acetyl(2,3,4,5,6-pentafluoroanil)-6-phenyl(2'-methoxy,3'-phenyl)-pyridine]copper dichloride
[2-acetyl(2,6-diisopropylanil)-6-phenyl(2'-methoxy,3'-t-butyl)-pyridine]iron dichloride
[2-acetyl(2,6-diisopropylanil)-6-phenyl(2'-methoxy,3'-t-butyl)-pyridine]cobalt dichloride
[2-acetyl(2,6-diisopropylanil)-6-phenyl(2'-methoxy,3'-t-butyl)-pyridine]nickel dichloride
[2-acetyl(2,6-diisopropylanil)-6-phenyl(2'-methoxy,3'-t-butyl)-pyridine]copper dichloride
[2-acetyl(2,4,6-trimethylanil)-6-phenyl(2'-methoxy,3'-t-butyl)-pyridine]iron dichloride
[2-acetyl(2,4,6-trimethylanil)-6-phenyl(2'-methoxy,3'-t-butyl)-pyridine]cobalt dichloride
[2-acetyl(2,4,6-trimethylanil)-6-phenyl(2'-methoxy, 3'-t-butyl)-pyridine]nickel dichloride
[2-acetyl(2,4,6-trimethylanil)-6-phenyl(2'-methoxy,3'-t-butyl)-pyridine]copper dichloride
[2-acetyl(2,3,4,5,6-pentafluoroanil)-6-phenyl(2'-methoxy,3'-t-butyl)-pyridine]iron dichloride
[2-acetyl(2,3,4,5,6-pentafluoroanil)-6-phenyl(2'-methoxy,3'-t-butyl)-pyridine]cobalt dichloride
[2-acetyl(2,3,4,5,6-pentafluoroanil)-6-phenyl(2'-methoxy,3'-t-butyl)-pyridine]nickel dichloride
[2-acetyl(2,3,4,5,6-pentafluoroanil)-6-phenyl(2'-methoxy,3'-t-butyl)-pyridine]copper dichloride
[2-acetyl(2,6-diisopropylanil)-6-phenyl(2'-hydroxy)-pyridine]iron dichloride
[2-acetyl(2,6-diisopropylanil)-6-phenyl(2'-hydroxy)-pyridine]cobalt dichloride
[2-acetyl(2,6-diisopropylanil)-6-phenyl((2'-hydroxy)-pyridine]nickel dichloride
[2-acetyl(2,6-diisopropylanil)-6-phenyl(2'-hydroxy)-pyridine]copper dichloride
[2-acetyl(2,4,6-trimethylanil)-6-phenyl(2'-hydroxy)-pyridine]iron dichloride
[2-acetyl(2,4,6-trimethylanil)-6-phenyl(2'-hydroxy)-pyridine]cobalt dichloride
[2-acetyl(2,4,6-trimethylanil)-6-phenyl(2'-hydroxy)-pyridine]nickel dichloride
[2-acetyl(2,4,6-trimethylanil)-6-phenyl(2'-hydroxy)-pyridine]copper dichloride
[2-acetyl(2,3,4,5,6-pentafluoroanil)-6-phenyl(2'-hydroxy)-pyridine]iron dichloride
[2-acetyl(2,3,4,5,6-pentafluoroanil)-6-phenyl(2'-hydroxy)-pyridine]cobalt dichloride
[2-acetyl(2,3,4,5,6-pentafluoroanil)-6-phenyl(2'-hydroxy)-pyridine]nickel dichloride
[2-acetyl(2,3,4,5,6-pentafluoroanil)-6-phenyl(2'-hydroxy)-pyridine]copper dichloride
[2-acetyl(2,6-diisopropylanil)-6-phenyl(2'-hydroxy,3'-phenyl)-pyridine]iron dichloride
[2-acetyl(2,6-diisopropylanil)-6-phenyl(2'-hydroxy,3'-phenyl)-pyridine]cobalt dichloride
[2-acetyl(2,6-diisopropylanil)-6-phenyl(2'-hydroxy,3'-phenyl)-pyridine]nickel dichloride
[2-acetyl(2,6-diisopropylanil)-6-phenyl(2'-hydroxy,3'-phenyl)-pyridine]copper dichloride
[2-acetyl(2,4,6-trimethylanil)-6-phenyl(2'-hydroxy,3'-phenyl)-pyridine]iron dichloride
[2-acetyl(2,4,6-trimethylanil)-6-phenyl(2'-hydroxy,3'-phenyl)-pyridine]cobalt dichloride
[2-acetyl(2,4,6-trimethylanil)-6-phenyl(2'-hydroxy,3'-phenyl)-pyridine]nickel dichloride
[2-acetyl(2,4,6-trimethylanil)-6-phenyl(2'-hydroxy,3'-phenyl)-pyridine]copper dichloride
[2-acetyl(2,3,4,5,6-pentafluoroanil)-6-phenyl(2'-hydroxy,3'-phenyl)-pyridine]iron dichloride
[2-acetyl(2,3,4,5,6-pentafluoroanil)-6-phenyl(2'-hydroxy,3'-phenyl)-pyridine]cobalt dichloride
[2-acetyl(2,3,4,5,6-pentafluoroanil)-6-phenyl(2'-hydroxy,3'-phenyl)-pyridine]nickel dichloride
[2-acetyl(2,3,4,5,6-pentafluoroanil)-6-phenyl(2'-hydroxy,3'-phenyl)-pyridine]copper dichloride
[2-acetyl(2,6-diisopropylanil)-6-phenyl(2'-hydroxy,3'-t-butyl)-pyridine]iron dichloride
[2-acetyl(2,6-diisopropylanil)-6-phenyl(2'-hydroxy,3'-t-butyl)-pyridine]cobalt dichloride
[2-acetyl(2,6-diisopropylanil)-6-phenyl(2'-hydroxy,3'-t-butyl)-pyridine]nickel dichloride
[2-acetyl(2,6-diisopropylanil)-6-phenyl(2'-hydroxy,3'-t-butyl)-pyridine]copper dichloride
[2-acetyl(2,4,6-trimethylanil)-6-phenyl(2'-hydroxy,3'-t-butyl)-pyridine]iron dichloride
[2-acetyl(2,4,6-trimethylanil)-6-phenyl(2'-hydroxy,3'-t-butyl)-pyridine]cobalt dichloride
[2-acetyl(2,4,6-trimethylanil)-6-phenyl(2'-hydroxy,3'-t-butyl)-pyridine]nickel dichloride
[2-acetyl(2,4,6-trimethylanil)-6-phenyl(2'-hydroxy,3'-t-butyl)-pyridine]copper dichloride
[2-acetyl(2,3,4,5,6-pentafluoroanil)-6-phenyl(2'-hydroxy,3'-t-butyl)-pyridine]iron dichloride
[2-acetyl(2,3,4,5,6-pentafluoroanil)-6-phenyl(2'-hydroxy,3'-t-butyl)-pyridine]cobalt dichloride
[2-acetyl(2,3,4,5,6-pentafluoroanil)-6-phenyl(2'-hydroxy,3'-t-butyl)-pyridine]nickel dichloride
[2-acetyl(2,3,4,5,6-pentafluoroanil)-6-phenyl(2'-hydroxy,3'-t-butyl)-pyridine]copper dichloride
[2-formyl(2,6-diisopropylanil)-6-phenyl(2'-methoxy)-pyridine]iron dichloride
[2-formyl(2,6-diisopropylanil)-6-phenyl(2'-methoxy)-pyridine]cobalt dichloride
[2-formyl(2,6-diisopropylanil)-6-phenyl(2'-methoxy)-pyridine]nickel dichloride
[2-formyl(2,6-diisopropylanil)-6-phenyl(2'-methoxy)-pyridine]copper dichloride
[2-acetyl(2,6-diisopropylanil)-6-phenyl(2'-methoxy)-pyridine]iron dibromide
[2-acetyl(2,6-diisopropylanil)-6-phenyl(2'-methoxy)-pyridine]cobalt dibromide
[2-acetyl(2,6-diisopropylanil)-6-phenyl(2'-methoxy)-pyridine]nickel dibromide
[2-acetyl(2,6-diisopropylanil)-6-phenyl(2'-methoxy)-pyridine]copper dibromide
[2-acetyl(2,4,6-trimethylanil)-6-phenyl(2'-methoxy)-pyridine]iron dibromide
[2-acetyl(2,4,6-trimethylanil)-6-phenyl(2'-methoxy)-pyridine]cobalt dibromide
[2-acetyl(2,4,6-trimethylanil)-6-phenyl(2'-methoxy)-pyridine]nickel dibromide
[2-acetyl(2,4,6-trimethylanil)-6-phenyl(2'-methoxy)-pyridine]copper dibromide

[2-acetyl(2,3,4,5,6-pentafluoroanil)-6-phenyl(2'-methoxy)-pyridine]iron dibromide
[2-acetyl(2,3,4,5,6-pentafluoroanil)-6-phenyl(2'-methoxy)-pyridine]cobalt dibromide
[2-acetyl(2,3,4,5,6-pentafluoroanil)-6-phenyl(2'-methoxy)-pyridine]nickel dibromide
[2-acetyl(2,3,4,5,6-pentafluoroanil)-6-phenyl(2'-methoxy)-pyridine]copper dibromide
[2-acetyl(2,6-diisopropylanil)-6-phenyl(2'-methoxy,3'-phenyl)-pyridine]iron dibromide
[2-acetyl(2,6-diisopropylanil)-6-phenyl(2'-methoxy,3'-phenyl)-pyridine]cobalt dibromide
[2-acetyl(2,6-diisopropylanil)-6-phenyl(2'-methoxy,3'-phenyl)-pyridine]nickel dibromide
[2-acetyl(2,6-diisopropylanil)-6-phenyl(2'-methoxy,3'-phenyl)-pyridine]copper dibromide
[2-acetyl(2,4,6-trimethylanil)-6-phenyl(2'-methoxy,3'-phenyl)-pyridine]iron dibromide
[2-acetyl(2,4,6-trimethylanil)-6-phenyl((2'-methoxy,3'-phenyl)-pyridine]cobalt dibromide
[2-acetyl(2,4,6-trimethylanil)-6-phenyl(2'-methoxy,3'-phenyl)-pyridine]nickel dibromide
[2-acetyl(2,4,6-trimethylanil)-6-phenyl(2'-methoxy,3'-phenyl)-pyridine]copper dibromide
[2-acetyl(2,3,4,5,6-pentafluoroanil)-6-phenyl(2'-methoxy,3'-phenyl)-pyridine]iron dibromide
[2-acetyl(2,3,4,5,6-pentafluoroanil)-6-phenyl(2'-methoxy,3'-phenyl)-pyridine]cobalt dibromide
[2-acetyl(2,3,4,5,6-pentafluoroanil)-6-phenyl(2'-methoxy,3'-phenyl)-pyridine]nickel dibromide
[2-acetyl(2,3,4,5,6-pentafluoroanil)-6-phenyl(2'-methoxy,3'-phenyl)-pyridine]copper dibromide
[2-acetyl(2,6-diisopropylanil)-6-phenyl(2'-methoxy,3'-t-butyl)-pyridine]iron dibromide
[2-acetyl(2,6-diisopropylanil)-6-phenyl(2'-methoxy,3'-t-butyl)-pyridine]cobalt dibromide
[2-acetyl(2,6-diisopropylanil)-6-phenyl(2'-methoxy,3'-t-butyl)-pyridine]nickel dibromide
[2-acetyl(2,6-diisopropylanil)-6-phenyl(2'-methoxy,3'-t-butyl)-pyridine]copper dibromide
[2-acetyl(2,4,6-trimethylanil)-6-phenyl(2'-methoxy,3'-t-butyl)-pyridine]iron dibromide
[2-acetyl(2,4,6-trimethylanil)-6-phenyl(2'-methoxy,3'-t-butyl)-pyridine]cobalt dibromide
[2-acetyl(2,4,6-trimethylanil)-6-phenyl(2'-methoxy, 3'-t-butyl)-pyridine]nickel dibromide
[2-acetyl(2,4,6-trimethylanil)-6-phenyl(2'-methoxy,3'-t-butyl)-pyridine]copper dibromide
[2-acetyl(2,3,4,5,6-pentafluoroanil)-6-phenyl(2'-methoxy,3'-t-butyl)-pyridine]iron dibromide
[2-acetyl(2,3,4,5,6-pentafluoroanil)-6-phenyl(2'-methoxy,3'-t-butyl)-pyridine]cobalt dibromide
[2-acetyl(2,3,4,5,6-pentafluoroanil)-6-phenyl(2'-methoxy,3'-t-butyl)-pyridine]nickel dibromide
[2-acetyl(2,3,4,5,6-pentafluoroanil)-6-phenyl(2'-methoxy,3'-t-butyl)-pyridine]copper dibromide
[2-acetyl(2,6-diisopropylanil)-6-phenyl(2'-hydroxy)-pyridine]iron dibromide
[2-acetyl(2,6-diisopropylanil)-6-phenyl(2'-hydroxy)-pyridine]cobalt dibromide
[2-acetyl(2,6-diisopropylanil)-6-phenyl((2'-hydroxy)-pyridine]nickel dibromide
[2-acetyl(2,6-diisopropylanil)-6-phenyl(2'-hydroxy)-pyridine]copper dibromide
[2-acetyl(2,4,6-trimethylanil)-6-phenyl(2'-hydroxy)-pyridine]iron dibromide
[2-acetyl(2,4,6-trimethylanil)-6-phenyl(2'-hydroxy)-pyridine]cobalt dibromide
[2-acetyl(2,4,6-trimethylanil)-6-phenyl(2'-hydroxy)-pyridine]nickel dibromide
[2-acetyl(2,4,6-trimethylanil)-6-phenyl(2'-hydroxy)-pyridine]copper dibromide
[2-acetyl(2,3,4,5,6-pentafluoroanil)-6-phenyl(2'-hydroxy)-pyridine]iron dibromide
[2-acetyl(2,3,4,5,6-pentafluoroanil)-6-phenyl(2'-hydroxy)-pyridine]cobalt dibromide
[2-acetyl(2,3,4,5,6-pentafluoroanil)-6-phenyl(2'-hydroxy)-pyridine]nickel dibromide
[2-acetyl(2,3,4,5,6-pentafluoroanil)-6-phenyl(2'-hydroxy)-pyridine]copper dibromide
[2-acetyl(2,6-diisopropylanil)-6-phenyl(2'-hydroxy,3'-phenyl)-pyridine]iron dibromide
[2-acetyl(2,6-diisopropylanil)-6-phenyl(2'-hydroxy,3'-phenyl)-pyridine]cobalt dibromide
[2-acetyl(2,6-diisopropylanil)-6-phenyl(2'-hydroxy,3'-phenyl)-pyridine]nickel dibromide
[2-acetyl(2,6-diisopropylanil)-6-phenyl(2'-hydroxy,3'-phenyl)-pyridine]copper dibromide
[2-acetyl(2,4,6-trimethylanil)-6-phenyl(2'-hydroxy,3'-phenyl)-pyridine]iron dibromide
[2-acetyl(2,4,6-trimethylanil)-6-phenyl(2'-hydroxy,3'-phenyl)-pyridine]cobalt dibromide
[2-acetyl(2,4,6-trimethylanil)-6-phenyl(2'-hydroxy,3'-phenyl)-pyridine]nickel dibromide
[2-acetyl(2,4,6-trimethylanil)-6-phenyl(2'-hydroxy,3'-phenyl)-pyridine]copper dibromide
[2-acetyl(2,3,4,5,6-pentafluoroanil)-6-phenyl(2'-hydroxy,3'-phenyl)-pyridine]iron dibromide
[2-acetyl(2,3,4,5,6-pentafluoroanil)-6-phenyl(2'-hydroxy,3'-phenyl)-pyridine]cobalt dibromide
[2-acetyl(2,3,4,5,6-pentafluoroanil)-6-phenyl(2'-hydroxy,3'-phenyl)-pyridine]nickel dibromide
[2-acetyl(2,3,4,5,6-pentafluoroanil)-6-phenyl(2'-hydroxy,3'-phenyl)-pyridine]copper dibromide
[2-acetyl(2,6-diisopropylanil)-6-phenyl(2'-hydroxy,3'-t-butyl)-pyridine]iron dibromide
[2-acetyl(2,6-diisopropylanil)-6-phenyl(2'-hydroxy,3'-t-butyl)-pyridine]cobalt dibromide
[2-acetyl(2,6-diisopropylanil)-6-phenyl(2'-hydroxy,3'-t-butyl)-pyridine]nickel dibromide
[2-acetyl(2,6-diisopropylanil)-6-phenyl(2'-hydroxy,3'-t-butyl)-pyridine]copper dibromide
[2-acetyl(2,4,6-trimethylanil)-6-phenyl(2'-hydroxy,3'-t-butyl)-pyridine]iron dibromide
[2-acetyl(2,4,6-trimethylanil)-6-phenyl(2'-hydroxy,3'-t-butyl)-pyridine]cobalt dibromide
[2-acetyl(2,4,6-trimethylanil)-6-phenyl(2'-hydroxy,3'-t-butyl)-pyridine]nickel dibromide
[2-acetyl(2,4,6-trimethylanil)-6-phenyl(2'-hydroxy,3'-t-butyl)-pyridine]copper dibromide
[2-acetyl(2,3,4,5,6-pentafluoroanil)-6-phenyl(2'-hydroxy,3'-t-butyl)-pyridine]iron dibromide
[2-acetyl(2,3,4,5,6-pentafluoroanil)-6-phenyl(2'-hydroxy,3'-t-butyl)-pyridine]cobalt dibromide
[2-acetyl(2,3,4,5,6-pentafluoroanil)-6-phenyl(2'-hydroxy,3'-t-butyl)-pyridine]nickel dibromide
[2-acetyl(2,3,4,5,6-pentafluoroanil)-6-phenyl(2'-hydroxy,3'-t-butyl)-pyridine]copper dibromide
[2-formyl(2,6-diisopropylanil)-6-phenyl(2'-methoxy)-pyridine]iron dibromide
[2-formyl(2,6-diisopropylanil)-6-phenyl(2'-methoxy)-pyridine]cobalt dibromide

[2-formyl(2,6-diisopropylanil)-6-phenyl(2'-methoxy)-pyridine]nickel dibromide
[2-formyl(2,6-diisopropylanil)-6-phenyl(2'-methoxy)-pyridine]copper dibromide
[2-acetyl(2,6-diisopropylanil)-6-phenyl(2'-oxo)-pyridine]iron chloride
[2-acetyl(2,6-diisopropylanil)-6-phenyl(2'-oxo)-pyridine]cobalt chloride
[2-acetyl(2,6-diisopropylanil)-6-phenyl(2'-oxo)-pyridine]nickel chloride
[2-acetyl(2,6-diisopropylanil)-6-phenyl(2'-oxo)-pyridine]copper chloride
[2-acetyl(2,4,6-trimethylanil)-6-phenyl(2'-oxo)-pyridine]iron chloride
[2-acetyl(2,4,6-trimethylanil)-6-phenyl(2'-oxo)-pyridine]cobalt chloride
[2-acetyl(2,4,6-trimethylanil)-6-phenyl(2'-oxo)-pyridine]nickel chloride
[2-acetyl(2,4,6-trimethylanil)-6-phenyl(2'-oxo)-pyridine]copper chloride
[2-acetyl(2,3,4,5,6-pentafluoroanil)-6-phenyl(2'-oxo)-pyridine]iron chloride
[2-acetyl(2,3,4,5,6-pentafluoroanil)-6-phenyl(2'-oxo)-pyridine]cobalt chloride
[2-acetyl(2,3,4,5,6-pentafluoroanil)-6-phenyl(2'-oxo)-pyridine]nickel chloride
[2-acetyl(2,3,4,5,6-pentafluoroanil)-6-phenyl(2'-oxo)-pyridine]copper chloride
[2-acetyl(2,6-diisopropylanil)-6-phenyl(2'-oxo),3'-phenyl)-pyridine]iron chloride
[2-acetyl(2,6-diisopropylanil)-6-phenyl(2'-oxo,3'-phenyl)-pyridine]cobalt chloride
[2-acetyl(2,6-diisopropylanil)-6-phenyl(2'-oxo,3'-phenyl)-pyridine]nickel chloride
[2-acetyl(2,6-diisopropylanil)-6-phenyl(2'-oxo,3'-phenyl)-pyridine]copper chloride
[2-acetyl(2,4,6-trimethylanil)-6-phenyl(2'-oxo,3'-phenyl)-pyridine]iron chloride
[2-acetyl(2,4,6-trimethylanil)-6-phenyl(2'-oxo,3'-phenyl)-pyridine]cobalt chloride
[2-acetyl(2,4,6-trimethylanil)-6-phenyl(2'-oxo,3'-phenyl)-pyridine]nickel chloride
[2-acetyl(2,4,6-trimethylanil)-6-phenyl(2'-oxo,3'-phenyl)-pyridine]copper chloride
[2-acetyl(2,3,4,5,6-pentafluoroanil)-6-phenyl(2'-oxo,3'-phenyl)-pyridine]iron chloride
[2-acetyl(2,3,4,5,6-pentafluoroanil)-6-phenyl(2'-oxo,3'-phenyl)-pyridine]cobalt chloride
[2-acetyl(2,3,4,5,6-pentafluoroanil)-6-phenyl(2'-oxo,3'-phenyl)-pyridine]nickel chloride
[2-acetyl(2,3,4,5,6-pentafluoroanil)-6-phenyl(2'-oxo,3'-phenyl)-pyridine]copper chloride
[2-acetyl(2,6-diisopropylanil)-6-phenyl(2'-oxo,3'-t-butyl)-pyridine]iron chloride
[2-acetyl(2,6-diisopropylanil)-6-phenyl(2'-oxo,3'-t-butyl)-pyridine]cobalt chloride
[2-acetyl(2,6-diisopropylanil)-6-phenyl(2'-oxo,3'-t-butyl)-pyridine]nickel chloride
[2-acetyl(2,6-diisopropylanil)-6-phenyl(2'-oxo,3'-t-butyl)-pyridine]copper chloride
[2-acetyl(2,4,6-trimethylanil)-6-phenyl(2'-oxo,3'-t-butyl)-pyridine]iron chloride
[2-acetyl(2,4,6-trimethylanil)-6-phenyl(2'-oxo,3'-t-butyl)-pyridine]cobalt chloride
[2-acetyl(2,4,6-trimethylanil)-6-phenyl(2'-oxo,3'-t-butyl)-pyridine]nickel chloride
[2-acetyl(2,4,6-trimethylanil)-6-phenyl(2'-oxo,3'-t-butyl)-pyridine]copper chloride
[2-acetyl(2,3,4,5,6-pentafluoroanil)-6-phenyl(2'-oxo,3'-t-butyl)-pyridine]iron chloride
[2-acetyl(2,3,4,5,6-pentafluoroanil)-6-phenyl(2'-oxo,3'-t-butyl)-pyridine]cobalt chloride
[2-acetyl(2,3,4,5,6-pentafluoroanil)-6-phenyl(2'-oxo,3'-t-butyl)-pyridine]nickel chloride
[2-acetyl(2,3,4,5,6-pentafluoroanil)-6-phenyl(2'-oxo,3'-t-butyl)-pyridine]copper chloride
[2-formyl(2,6-diisopropylanil)-6-phenyl(2'-oxo)-pyridine]iron chloride
[2-formyl(2,6-diisopropylanil)-6-phenyl(2'-oxo)-pyridine]cobalt chloride
[2-formyl(2,6-diisopropylanil)-6-phenyl(2'-oxo)-pyridine]nickel chloride
[2-formyl(2,6-diisopropylanil)-6-phenyl(2'-oxo)-pyridine]copper chloride
[2-acetyl(2,6-diisopropylanil)-6-phenyl(2'-oxo)-pyridine]iron bromide
[2-acetyl(2,6-diisopropylanil)-6-phenyl(2'-oxo)-pyridine]cobalt bromide
[2-acetyl(2,6-diisopropylanil)-6-phenyl(2'-oxo)-pyridine]nickel bromide
[2-acetyl(2,6-diisopropylanil)-6-phenyl(2'-oxo)-pyridine]copper bromide
[2-acetyl(2,4,6-trimethylanil)-6-phenyl(2'-oxo)-pyridine]iron bromide
[2-acetyl(2,4,6-trimethylanil)-6-phenyl(2'-oxo)-pyridine]cobalt bromide
[2-acetyl(2,4,6-trimethylanil)-6-phenyl(2'-oxo)-pyridine]nickel bromide
[2-acetyl(2,4,6-trimethylanil)-6-phenyl(2'-oxo)-pyridine]copper bromide
[2-acetyl(2,3,4,5,6-pentafluoroanil)-6-phenyl(2'-oxo)-pyridine]iron bromide
[2-acetyl(2,3,4,5,6-pentafluoroanil)-6-phenyl(2'-oxo)-pyridine]cobalt bromide
[2-acetyl(2,3,4,5,6-pentafluoroanil)-6-phenyl(2'-oxo)-pyridine]nickel bromide
[2-acetyl(2,3,4,5,6-pentafluoroanil)-6-phenyl(2'-oxo)-pyridine]copper bromide
[2-acetyl(2,6-diisopropylanil)-6-phenyl(2'-oxo),3'-phenyl)-pyridine]iron bromide
[2-acetyl(2,6-diisopropylanil)-6-phenyl(2'-oxo,3'-phenyl)-pyridine]cobalt bromide
[2-acetyl(2,6-diisopropylanil)-6-phenyl(2'-oxo,3'-phenyl)-pyridine]nickel bromide
[2-acetyl(2,6-diisopropylanil)-6-phenyl(2'-oxo,3'-phenyl)-pyridine]copper bromide
[2-acetyl(2,4,6-trimethylanil)-6-phenyl(2'-oxo,3'-phenyl)-pyridine]iron bromide
[2-acetyl(2,4,6-trimethylanil)-6-phenyl(2'-oxo,3'-phenyl)-pyridine]cobalt bromide
[2-acetyl(2,4,6-trimethylanil)-6-phenyl(2'-oxo,3'-phenyl)-pyridine]nickel bromide
[2-acetyl(2,4,6-trimethylanil)-6-phenyl(2'-oxo,3'-phenyl)-pyridine]copper bromide
[2-acetyl(2,3,4,5,6-pentafluoroanil)-6-phenyl(2'-oxo,3'-phenyl)-pyridine]iron bromide
[2-acetyl(2,3,4,5,6-pentafluoroanil)-6-phenyl(2'-oxo,3'-phenyl)-pyridine]cobalt bromide
[2-acetyl(2,3,4,5,6-pentafluoroanil)-6-phenyl(2'-oxo,3'-phenyl)-pyridine]nickel bromide
[2-acetyl(2,3,4,5,6-pentafluoroanil)-6-phenyl(2'-oxo,3'-phenyl)-pyridine]copper bromide

[2-acetyl(2,6-diisopropylanil)-6-phenyl(2'-oxo,3'-t-butyl)-pyridine]iron bromide
[2-acetyl(2,6-diisopropylanil)-6-phenyl(2'-oxo,3'-t-butyl)-pyridine]cobalt bromide
[2-acetyl(2,6-diisopropylanil)-6-phenyl(2'-oxo,3'-t-butyl)-pyridine]nickel bromide
[2-acetyl(2,6-diisopropylanil)-6-phenyl(2'-oxo,3'-t-butyl)-pyridine]copper bromide
[2-acetyl(2,4,6-trimethylanil)-6-phenyl(2'-oxo,3'-t-butyl)-pyridine]iron bromide
[2-acetyl(2,4,6-trimethylanil)-6-phenyl(2'-oxo,3'-t-butyl)-pyridine]cobalt bromide
[2-acetyl(2,4,6-trimethylanil)-6-phenyl(2'-oxo,3'-t-butyl)-pyridine]nickel bromide
[2-acetyl(2,4,6-trimethylanil)-6-phenyl(2'-oxo,3'-t-butyl)-pyridine]copper bromide
[2-acetyl(2,3,4,5,6-pentafluoroanil)-6-phenyl(2'-oxo,3'-t-butyl)-pyridine]iron bromide
[2-acetyl(2,3,4,5,6-pentafluoroanil)-6-phenyl(2'-oxo,3'-t-butyl)-pyridine]cobalt bromide
[2-acetyl(2,3,4,5,6-pentafluoroanil)-6-phenyl(2'-oxo,3'-t-butyl)-pyridine]nickel bromide
[2-acetyl(2,3,4,5,6-pentafluoroanil)-6-phenyl(2'-oxo,3'-t-butyl)-pyridine]copper bromide
[2-formyl(2,6-diisopropylanil)-6-phenyl(2'-oxo)-pyridine]iron bromide
[2-formyl(2,6-diisopropylanil)-6-phenyl(2'-oxo)-pyridine]cobalt bromide
[2-formyl(2,6-diisopropylanil)-6-phenyl(2'-oxo)-pyridine]nickel bromide
[2-formyl(2,6-diisopropylanil)-6-phenyl(2'-oxo)-pyridine]copper bromide
[2-acetyl(2,6-diisopropylanil)-6-phenyl(2'-oxo)-pyridine]iron methyl
[2-acetyl(2,6-diisopropylanil)-6-phenyl(2'-oxo)-pyridine]cobalt methyl
[2-acetyl(2,6-diisopropylanil)-6-phenyl(2'-oxo)-pyridine]nickel methyl
[2-acetyl(2,6-diisopropylanil)-6-phenyl(2'-oxo)-pyridine]copper methyl
[2-acetyl(2,4,6-trimethylanil)-6-phenyl(2'-oxo)-pyridine]iron methyl
[2-acetyl(2,4,6-trimethylanil)-6-phenyl(2'-oxo)-pyridine]cobalt methyl
[2-acetyl(2,4,6-trimethylanil)-6-phenyl(2'-oxo)-pyridine]nickel methyl
[2-acetyl(2,4,6-trimethylanil)-6-phenyl(2'-oxo)-pyridine]copper methyl
[2-acetyl(2,3,4,5,6-pentafluoroanil)-6-phenyl(2'-oxo)-pyridine]iron methyl
[2-acetyl(2,3,4,5,6-pentafluoroanil)-6-phenyl(2'-oxo)-pyridine]cobalt methyl
[2-acetyl(2,3,4,5,6-pentafluoroanil)-6-phenyl(2'-oxo)-pyridine]nickel methyl
[2-acetyl(2,3,4,5,6-pentafluoroanil)-6-phenyl(2'-oxo)-pyridine]copper methyl
[2-acetyl(2,6-diisopropylanil)-6-phenyl(2'-oxo),3'-phenyl)-pyridine]iron methyl
[2-acetyl(2,6-diisopropylanil)-6-phenyl(2'-oxo),3'-phenyl)-pyridine]cobalt methyl
[2-acetyl(2,6-diisopropylanil)-6-phenyl(2'-oxo),3'-phenyl)-pyridine]nickel methyl
[2-acetyl(2,6-diisopropylanil)-6-phenyl(2'-oxo),3'-phenyl)-pyridine]copper methyl
[2-acetyl(2,4,6-trimethylanil)-6-phenyl(2'-oxo,3'-phenyl)-pyridine]iron methyl
[2-acetyl(2,4,6-trimethylanil)-6-phenyl(2'-oxo,3'-phenyl)-pyridine]cobalt methyl
[2-acetyl(2,4,6-trimethylanil)-6-phenyl(2'-oxo,3'-phenyl)-pyridine]nickel methyl
[2-acetyl(2,4,6-trimethylanil)-6-phenyl(2'-oxo,3'-phenyl)-pyridine]copper methyl
[2-acetyl(2,3,4,5,6-pentafluoroanil)-6-phenyl(2'-oxo,3'-phenyl)-pyridine]iron methyl
[2-acetyl(2,3,4,5,6-pentafluoroanil)-6-phenyl(2'-oxo,3'-phenyl)-pyridine]cobalt methyl
[2-acetyl(2,3,4,5,6-pentafluoroanil)-6-phenyl(2'-oxo,3'-phenyl)-pyridine]nickel methyl
[2-acetyl(2,3,4,5,6-pentafluoroanil)-6-phenyl(2'-oxo,3'-phenyl)-pyridine]copper methyl
[2-acetyl(2,6-diisopropylanil)-6-phenyl(2'-oxo,3'-t-butyl)-pyridine]iron methyl
[2-acetyl(2,6-diisopropylanil)-6-phenyl(2'-oxo,3'-t-butyl)-pyridine]cobalt methyl
[2-acetyl(2,6-diisopropylanil)-6-phenyl(2'-oxo,3'-t-butyl)-pyridine]nickel methyl
[2-acetyl(2,6-diisopropylanil)-6-phenyl(2'-oxo,3'-t-butyl)-pyridine]copper methyl
[2-acetyl(2,4,6-trimethylanil)-6-phenyl(2'-oxo,3'-t-butyl)-pyridine]iron methyl
[2-acetyl(2,4,6-trimethylanil)-6-phenyl(2'-oxo,3'-t-butyl)-pyridine]cobalt methyl
[2-acetyl(2,4,6-trimethylanil)-6-phenyl(2'-oxo,3'-t-butyl)-pyridine]nickel methyl
[2-acetyl(2,4,6-trimethylanil)-6-phenyl(2'-oxo,3'-t-butyl)-pyridine]copper methyl
[2-acetyl(2,3,4,5,6-pentafluoroanil)-6-phenyl(2'-oxo,3'-t-butyl)-pyridine]iron methyl
[2-acetyl(2,3,4,5,6-pentafluoroanil)-6-phenyl(2'-oxo,3'-t-butyl)-pyridine]cobalt methyl
[2-acetyl(2,3,4,5,6-pentafluoroanil)-6-phenyl(2'-oxo,3'-t-butyl)-pyridine]nickel methyl
[2-acetyl(2,3,4,5,6-pentafluoroanil)-6-phenyl(2'-oxo,3'-t-butyl)-pyridine]copper methyl
[2-formyl(2,6-diisopropylanil)-6-phenyl(2'-oxo)-pyridine]iron methyl
[2-formyl(2,6-diisopropylanil)-6-phenyl(2'-oxo)-pyridine]cobalt methyl
[2-formyl(2,6-diisopropylanil)-6-phenyl(2'-oxo)-pyridine]nickel methyl
[2-formyl(2,6-diisopropylanil)-6-phenyl(2'-oxo)-pyridine]copper methyl
[2-acetyl(2,6-diisopropylanil)-6-phenyl(2'-oxo)-pyridine]iron benzyl
[2-acetyl(2,6-diisopropylanil)-6-phenyl(2'-oxo)-pyridine]cobalt benzyl
[2-acetyl(2,6-diisopropylanil)-6-phenyl(2'-oxo)-pyridine]nickel benzyl
[2-acetyl(2,6-diisopropylanil)-6-phenyl(2'-oxo)-pyridine]copper benzyl
[2-acetyl(2,4,6-trimethylanil)-6-phenyl(2'-oxo)-pyridine]iron benzyl
[2-acetyl(2,4,6-trimethylanil)-6-phenyl(2'-oxo)-pyridine]cobalt benzyl
[2-acetyl(2,4,6-trimethylanil)-6-phenyl(2'-oxo)-pyridine]nickel benzyl
[2-acetyl(2,4,6-trimethylanil)-6-phenyl(2'-oxo)-pyridine]copper benzyl
[2-acetyl(2,3,4,5,6-pentafluoroanil)-6-phenyl(2'-oxo)-pyridine]iron benzyl
[2-acetyl(2,3,4,5,6-pentafluoroanil)-6-phenyl(2'-oxo)-pyridine]cobalt benzyl

[2-acetyl(2,3,4,5,6-pentafluoroanil)-6-phenyl(2'-oxo)-pyridine]nickel benzyl
[2-acetyl(2,3,4,5,6-pentafluoroanil)-6-phenyl(2'-oxo)-pyridine]copper benzyl
[2-acetyl(2,6-diisopropylanil)-6-phenyl(2'-oxo),3'-phenyl)-pyridine]iron benzyl
[2-acetyl(2,6-diisopropylanil)-6-phenyl(2'-oxo,3'-phenyl)-pyridine]cobalt benzyl
[2-acetyl(2,6-diisopropylanil)-6-phenyl(2'-oxo,3'-phenyl)-pyridine]nickel benzyl
[2-acetyl(2,6-diisopropylanil)-6-phenyl(2'-oxo,3'-phenyl)-pyridine]copper benzyl
[2-acetyl(2,4,6-trimethylanil)-6-phenyl(2'-oxo,3'-phenyl)-pyridine]iron benzyl
[2-acetyl(2,4,6-trimethylanil)-6-phenyl(2'-oxo,3'-phenyl)-pyridine]cobalt benzyl
[2-acetyl(2,4,6-trimethylanil)-6-phenyl(2'-oxo,3'-phenyl)-pyridine]nickel benzyl
[2-acetyl(2,4,6-trimethylanil)-6-phenyl(2'-oxo,3'-phenyl)-pyridine]copper benzyl
[2-acetyl(2,3,4,5,6-pentafluoroanil)-6-phenyl(2'-oxo,3'-phenyl)-pyridine]iron benzyl
[2-acetyl(2,3,4,5,6-pentafluoroanil)-6-phenyl(2'-oxo,3'-phenyl)-pyridine]cobalt benzyl
[2-acetyl(2,3,4,5,6-pentafluoroanil)-6-phenyl(2'-oxo,3'-phenyl)-pyridine]nickel benzyl
[2-acetyl(2,3,4,5,6-pentafluoroanil)-6-phenyl(2'-oxo,3'-phenyl)-pyridine]copper benzyl
[2-acetyl(2,6-diisopropylanil)-6-phenyl(2'-oxo,3'-t-butyl)-pyridine]iron benzyl
[2-acetyl(2,6-diisopropylanil)-6-phenyl(2'-oxo,3'-t-butyl)-pyridine]cobalt benzyl
[2-acetyl(2,6-diisopropylanil)-6-phenyl(2'-oxo,3'-t-butyl)-pyridine]nickel benzyl
[2-acetyl(2,6-diisopropylanil)-6-phenyl(2'-oxo,3'-t-butyl)-pyridine]copper benzyl
[2-acetyl(2,4,6-trimethylanil)-6-phenyl(2'-oxo,3'-t-butyl)-pyridine]iron benzyl
[2-acetyl(2,4,6-trimethylanil)-6-phenyl(2'-oxo,3'-t-butyl)-pyridine]cobalt benzyl
[2-acetyl(2,4,6-trimethylanil)-6-phenyl(2'-oxo,3'-t-butyl)-pyridine]nickel benzyl
[2-acetyl(2,4,6-trimethylanil)-6-phenyl(2'-oxo,3'-t-butyl)-pyridine]copper benzyl
[2-acetyl(2,3,4,5,6-pentafluoroanil)-6-phenyl(2'-oxo,3'-t-butyl)-pyridine]iron benzyl
[2-acetyl(2,3,4,5,6-pentafluoroanil)-6-phenyl(2'-oxo,3'-t-butyl)-pyridine]cobalt benzyl
[2-acetyl(2,3,4,5,6-pentafluoroanil)-6-phenyl(2'-oxo,3'-t-butyl)-pyridine]nickel benzyl
[2-acetyl(2,3,4,5,6-pentafluoroanil)-6-phenyl(2'-oxo,3'-t-butyl)-pyridine]copper benzyl
[2-formyl(2,6-diisopropylanil)-6-phenyl(2'-oxo)-pyridine] iron benzyl
[2-formyl(2,6-diisopropylanil)-6-phenyl(2'-oxo)-pyridine] cobalt benzyl
[2-formyl(2,6-diisopropylanil)-6-phenyl(2'-oxo)-pyridine] nickel benzyl, and
[2-formyl(2,6-diisopropylanil)-6-phenyl(2'-oxo)-pyridine] copper benzyl.

This invention also further relates to transition metal compounds represented by formulae 11 and 12.

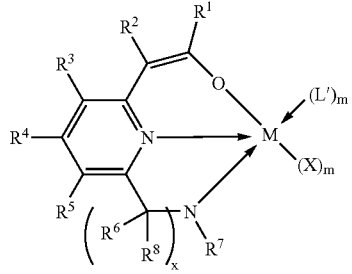

Formula 11

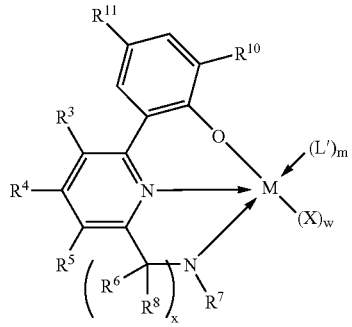

Formula 12 wherein
M is a group 4, 5 or 6 transition metal, preferably a group 4 transition metal, preferably Ti, Zr or Hf;
N is nitrogen;
O is oxygen;
each X is, independently, a hydride, hydrocarbyl, substituted hydrocarbyl, halocarbyl, substituted halocarbyl,
w is 1, 2 or 3;
additionally, X may independently be selected from halogen, alkoxide, aryloxide, amide, phosphide, or other anionic ligand when Lewis-acid activators (such as methylalumoxane, aluminum alkyls, alkylaluminum alkoxides) or alkylaluminum halides (capable of donating a hydride, hydrocarbyl, substituted hydrocarbyl, halocarbyl or substituted halocarbyl X ligand to the transition metal component) are used, or when an ionic activator is capable of extracting X, provided that the resulting activated catalyst contains as least one M—H or M—C bond into which an olefin can insert;
each $R^1$ and $R^2$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or independently, may join together to form a $C_4$ to $C_{62}$ cyclic or polycyclic ring structure;
each $R^3, R^4, R^5$, is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or independently, may join together to form a $C_4$ to $C_{62}$ cyclic or polycyclic ring structure;

each $R^6$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;

each $R^7$ is, independently, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;

each $R^8$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;

each $R^{10}$ is, independently, a hydrocarbyl, a substituted hydrocarbyl, a halocarbyl, or a substituted halocarbyl;

each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group;

x is 1, 2, 3 or 4, preferably, x is 1;

L' is a neutral ligand bonded to M and is preferably selected from the group consisting of acetonitrile, diethyl ether, tetrahydrofuran, dimethylaniline, trimethylamine, tributylamine, trimethylphosphine, triphenylphosphine lithium chloride, ethylene, propylene, butene, octene, styrene, and the like; and m is 0 or 1 and indicates the absence or presence of L'.

In a preferred embodiment the halocarbyls are fluorocarbyls and the substituted halocarbyls are substituted fluorocarbyls.

To illustrate members of the transition metal catalyst compounds useful in this invention, select any combination of the species listed in Table 2.

| R', $R^1$, $R^2$, $R^3$, $R^4$, $R^5$, $R^6$, $R^{10}$, $R^{11}$ | $R^7$ | X | M | L' |
| --- | --- | --- | --- | --- |
| hydrogen | propyl | chloride | titanium | acetonitrile |
| methyl | butyl | bromide | zirconium | diethyl ether |
| ethyl | pentyl | iodide | hafnium | tetrahydrofuran |
| propyl | hexyl | methyl | vanadium | furan |
| butyl | heptyl | ethyl | niobium | thiofuran |
| pentyl | octyl | propyl | tantalum | chromane |
| hexyl | nonyl | butyl | chromium | isochromane |
| heptyl | decyl | pentyl | molybdenum | thiochromane |
| octyl | undecyl | hexyl | tungsten | thioisochromane |
| nonyl | dodecyl | heptyl | | quinuclidine |
| decyl | tridecyl | octyl | | benzofuran |
| undecyl | tetradecyl | nonyl | | chromene |
| dodecyl | octacosyl | decyl | | isobenzofuran |
| tridecyl | nonacosyl | undecyl | | isoquinoline |
| tetradecyl | triacontyl | dodecyl | | oxazole |
| octacosyl | cyclohexyl | tridecyl | | phenanthridine |
| nonacosyl | cyclopentyl | tetradecyl | | pyran |
| triacontyl | cycloheptyl | pentadecyl | | pyridine |
| cyclohexyl | cyclooctyl | hexadecyl | | quinoline |
| cyclopentyl | cyclodecyl | heptadecyl | | selenophene |
| cycloheptyl | cyclododecyl | octadecyl | | thiophene |
| cyclooctyl | naphthyl | nonadecyl | | trimethylamine |
| cyclodecyl | phenyl | eicosyl | | triethylamine |
| cyclododecyl | tolyl | heneicosyl | | tributylamine |
| naphthyl | benzyl | docosyl | | dimethylaniline |
| phenyl | phenethyl | tricosyl | | trimethylphosphine |
| tolyl | dimethylphenyl | tetracosyl | | triphenylphosphine |
| benzyl | trimethylphenyl | pentacosyl | | ethylene |
| phenethyl | methylphenyl | hexacosyl | | propylene |
| dimethylphenyl | ethylphenyl | heptacosyl | | butene |
| diethylphenyl | diethylphenyl | octacosyl | | hexene |
| anthracenyl | triethylphenyl | nonacosyl | | octene |
| adamantyl | propylphenyl | triacontyl | | cyclohexene |
| Norbornyl | dipropylphenyl | hydride | | vinylcyclohexene |
| $CF_3$ | tripropylphenyl | phenyl | | benzene |
| $NO_2$ | Methylethylphenyl | benzyl | | styrene |
| t-butyl | dibutylphenyl | phenethyl | | methylstyrene |
| i-propyl | butylphenyl | tolyl | | lithium chloride |
| naphthyl | | methoxy | | Ammonium chloride |
| fluoride | | ethoxy | | |
| | | propoxy | | |
| | | butoxy | | |
| | | dimethylamido | | |
| | | diethylamido | | |
| | | methylethylamido | | |
| | | phenoxy | | |
| | | benzoxy | | |
| | | allyl | | |

A selection of catalyst precursors are detailed below. These are by way of an example only and are not intended to list every catalyst precursor that is within the scope of the invention:

[2-(2,6-diisopropylphenyl)amido(dimethyl)methyl-6-phenyl(2'-oxo)-pyridine]titanium dichloride
[2-(2,6-diisopropylphenyl)amido(dimethyl)methyl-6-phenyl(2'-oxo)-pyridine]zirconium dichloride
[2-(2,6-diisopropylphenyl)amido(dimethyl)methyl-6-phenyl(2'-oxo)-pyridine]hafnium dichloride
[2-(2,4,6-trimethylphenyl)amido(dimethyl)methyl-6-phenyl(2'-oxo)-pyridine]titanium dichloride
[2-(2,4,6-trimethylphenyl)amido(dimethyl)methyl-6-phenyl(2'-oxo)-pyridine]zirconium dichloride
[2-(2,4,6-trimethylphenyl)amido(dimethyl)methyl-6-phenyl(2'-oxo)-pyridine]hafnium dichloride
[2-(2,3,4,5,6-pentafluorophenyl)amido(dimethyl)methyl-6-phenyl(2'-oxo)-pyridine]titanium dichloride
[2-(2,3,4,5,6-pentafluorophenyl)amido(dimethyl)methyl-6-phenyl(2'-oxo)-pyridine]zirconium dichloride
[2-(2,3,4,5,6-pentafluorophenyl)amido(dimethyl)methyl-6-phenyl(2'-oxo)-pyridine]hafnium dichloride
[2-(2,6-diisopropylphenyl)amido(dimethyl)methyl-6-phenyl(2'-oxo,3'-phenyl)-pyridine]titanium dichloride
[2-(2,6-diisopropylphenyl)amido(dimethyl)methyl-6-phenyl(2'-oxo,3'-phenyl)-pyridine]zirconium dichloride
[2-(2,6-diisopropylphenyl)amido(dimethyl)methyl-6-phenyl(2'-oxo,3'-phenyl)-pyridine]hafnium dichloride
[2-(2,4,6-trimethylphenyl)amido(dimethyl)methyl-6-phenyl(2'-oxo,3'-phenyl)-pyridine]titanium dichloride
[2-(2,4,6-trimethylphenyl)amido(dimethyl)methyl-6-phenyl(2'-oxo,3'-phenyl)-pyridine]zirconium dichloride
[2-(2,4,6-trimethylphenyl)amido(dimethyl)methyl-6-phenyl(2'-oxo,3'-phenyl)-pyridine]hafnium dichloride
[2-(2,3,4,5,6-pentafluorophenyl)amido(dimethyl)methyl-6-phenyl(2'-hydroxy,3'-phenyl)-pyridine]titanium dichloride
[2-(2,3,4,5,6-pentafluorophenyl)amido(dimethyl)methyl-6-phenyl(2'-oxo,3'-phenyl)-pyridine]zirconium dichloride
[2-(2,3,4,5,6-pentafluorophenyl)amido(dimethyl)methyl-6-phenyl(2'-oxo,3'-phenyl)-pyridine]hafnium dichloride
[2-(2,6-diisopropylphenyl)amido(dimethyl)methyl-6-phenyl(2'-oxo,3'-t-butyl)-pyridine]titanium dichloride
[2-(2,6-diisopropylphenyl)amido(dimethyl)methyl-6-phenyl(2'-oxo,3'-t-butyl)-pyridine]zirconium dichloride
[2-(2,6-diisopropylphenyl)amido(dimethyl)methyl-6-phenyl(2'-oxo,3'-t-butyl)-pyridine]hafnium dichloride
[2-(2,4,6-trimethylphenyl)amido(dimethyl)methyl-6-phenyl(2'-oxo,3'-t-butyl)-pyridine]titanium dichloride
[2-(2,4,6-trimethylphenyl)amido(dimethyl)methyl-6-phenyl(2'-oxo,3'-t-butyl)-pyridine]zirconium dichloride
[2-(2,4,6-trimethylphenyl)amido(dimethyl)methyl-6-phenyl(2'-oxo,3'-t-butyl)-pyridine]hafnium dichloride
[2-(2,3,4,5,6-pentafluorophenyl)amido(dimethyl)methyl-6-phenyl(2'-hydroxy,3'-t-butyl)-pyridine]titanium dichloride
[2-(2,3,4,5,6-pentafluorophenyl)amido(dimethyl)methyl-6-phenyl(2'-oxo,3'-t-butyl)-pyridine]zirconium dichloride
[2-(2,3,4,5,6-pentafluorophenyl)amido(dimethyl)methyl-6-phenyl(2'-oxo,3'-t-butyl)-pyridine]hafnium dichloride
[2-(2,6-diisopropylphenyl)amido(dimethyl)methyl-6-phenyl(2'-oxo)-pyridine]titanium dimethyl
[2-(2,6-diisopropylphenyl)amido(dimethyl)methyl-6-phenyl(2'-oxo)-pyridine]zirconium dimethyl
[2-(2,6-diisopropylphenyl)amino(dimethyl)methyl-6-phenyl(2'-oxo)-pyridine]hafnium dimethyl
[2-(2,4,6-trimethylphenyl)amido(dimethyl)methyl-6-phenyl(2'-oxo)-pyridine]titanium dimethyl
[2-(2,4,6-trimethylphenyl)amido(dimethyl)methyl-6-phenyl(2'-oxo)-pyridine]zirconium dimethyl
[2-(2,4,6-trimethylphenyl)amido(dimethyl)methyl-6-phenyl(2'-oxo)-pyridine]hafnium dimethyl
[2-(2,3,4,5,6-pentafluorophenyl)amido(dimethyl)methyl-6-phenyl(2'-oxo)-pyridine]titanium dimethyl
[2-(2,3,4,5,6-pentafluorophenyl)amido(dimethyl)methyl-6-phenyl(2'-oxo)-pyridine]zirconium dimethyl
[2-(2,3,4,5,6-pentafluorophenyl)amido(dimethyl)methyl-6-phenyl(2'-oxo)-pyridine]hafnium dimethyl
[2-(2,6-diisopropylphenyl)amido(dimethyl)methyl-6-phenyl(2'-oxo,3'-phenyl)-pyridine]titanium dimethyl
[2-(2,6-diisopropylphenyl)amido(dimethyl)methyl-6-phenyl(2'-oxo,3'-phenyl)-pyridine]zirconium dimethyl
[2-(2,6-diisopropylphenyl)amido(dimethyl)methyl-6-phenyl(2'-oxo,3'-phenyl)-pyridine]hafnium dimethyl
[2-(2,4,6-trimethylphenyl)amido(dimethyl)methyl-6-phenyl(2'-oxo,3'-phenyl)-pyridine]titanium dimethyl
[2-(2,4,6-trimethylphenyl)amido(dimethyl)methyl-6-phenyl(2'-oxo,3'-phenyl)-pyridine]zirconium dimethyl
[2-(2,4,6-trimethylphenyl)amido(dimethyl)methyl-6-phenyl(2'-oxo,3'-phenyl)-pyridine]hafnium dimethyl
[2-(2,3,4,5,6-pentafluorophenyl)amido(dimethyl)methyl-6-phenyl(2'-hydroxy,3'-phenyl)-pyridine]titanium dimethyl
[2-(2,3,4,5,6-pentafluorophenyl)amido(dimethyl)methyl-6-phenyl(2'-oxo,3'-phenyl)-pyridine]zirconium dimethyl
[2-(2,3,4,5,6-pentafluorophenyl)amido(dimethyl)methyl-6-phenyl(2'-oxo,3'-phenyl)-pyridine]hafnium dimethyl
[2-(2,6-diisopropylphenyl)amido(dimethyl)methyl-6-phenyl(2'-oxo,3'-t-butyl)-pyridine]titanium dimethyl
[2-(2,6-diisopropylphenyl)amido(dimethyl)methyl-6-phenyl(2'-oxo,3'-t-butyl)-pyridine]zirconium dimethyl
[2-(2,6-diisopropylphenyl)amido(dimethyl)methyl-6-phenyl(2'-oxo,3'-t-butyl)-pyridine]hafnium dimethyl
[2-(2,4,6-trimethylphenyl)amido(dimethyl)methyl-6-phenyl(2'-oxo,3'-t-butyl)-pyridine]titanium dimethyl
[2-(2,4,6-trimethylphenyl)amido(dimethyl)methyl-6-phenyl(2'-oxo,3'-t-butyl)-pyridine]zirconium dimethyl
[2-(2,4,6-trimethylphenyl)amido(dimethyl)methyl-6-phenyl(2'-oxo,3'-t-butyl)-pyridine]hafnium dimethyl
[2-(2,3,4,5,6-pentafluorophenyl)amido(dimethyl)methyl-6-phenyl(2'-hydroxy,3'-t-butyl)-pyridine]titanium dimethyl
[2-(2,3,4,5,6-pentafluorophenyl)amido(dimethyl)methyl-6-phenyl(2'-oxo,3'-t-butyl)-pyridine]zirconium dimethyl
[2-(2,3,4,5,6-pentafluorophenyl)amido(dimethyl)methyl-6-phenyl(2'-oxo,3'-t-butyl)-pyridine]hafnium dimethyl
[2-(2,6-diisopropylphenyl)amido(dimethyl)methyl-6-phenyl(2'-oxo)-pyridine]titanium dibenzyl
[2-(2,6-diisopropylphenyl)amido(dimethyl)methyl-6-phenyl(2'-oxo)-pyridine]zirconium dibenzyl
[2-(2,6-diisopropylphenyl)amido(dimethyl)methyl-6-phenyl(2'-oxo)-pyridine]hafnium dibenzyl
[2-(2,4,6-trimethylphenyl)amido(dimethyl)methyl-6-phenyl(2'-oxo)-pyridine]titanium dibenzyl
[2-(2,4,6-trimethylphenyl)amido(dimethyl)methyl-6-phenyl(2'-oxo)-pyridine]zirconium dibenzyl
[2-(2,4,6-trimethylphenyl)amido(dimethyl)methyl-6-phenyl(2'-oxo)-pyridine]hafnium dibenzyl
[2-(2,3,4,5,6-pentafluorophenyl)amido(dimethyl)methyl-6-phenyl(2'-oxo)-pyridine]titanium dibenzyl
[2-(2,3,4,5,6-pentafluorophenyl)amido(dimethyl)methyl-6-phenyl(2'-oxo)-pyridine]zirconium dibenzyl
[2-(2,3,4,5,6-pentafluorophenyl)amido(dimethyl)methyl-6-phenyl(2'-oxo)-pyridine]hafnium dibenzyl

[2-(2,6-diisopropylphenyl)amido(dimethyl)methyl-6-phenyl(2'-oxo,3'-phenyl)-pyridine]titanium dibenzyl
[2-(2,6-diisopropylphenyl)amido(dimethyl)methyl-6-phenyl(2'-oxo,3'-phenyl)-pyridine]zirconium dibenzyl
[2-(2,6-diisopropylphenyl)amido(dimethyl)methyl-6-phenyl(2'-oxo,3'-phenyl)-pyridine]hafnium dibenzyl
[2-(2,4,6-trimethylphenyl)amido(dimethyl)methyl-6-phenyl(2'-oxo,3'-phenyl)-pyridine]titanium dibenzyl
[2-(2,4,6-trimethylphenyl)amido(dimethyl)methyl-6-phenyl(2'-oxo,3'-phenyl)-pyridine]zirconium dibenzyl
[2-(2,4,6-trimethylphenyl)amido(dimethyl)methyl-6-phenyl(2'-oxo,3'-phenyl)-pyridine]hafnium dibenzyl
[2-(2,3,4,5,6-pentafluorophenyl)amido(dimethyl)methyl-6-phenyl(2'-hydroxy,3'-phenyl)-pyridine]titanium dibenzyl
[2-(2,3,4,5,6-pentafluorophenyl)amido(dimethyl)methyl-6-phenyl(2'-oxo,3'-phenyl)-pyridine]zirconium dibenzyl
[2-(2,3,4,5,6-pentafluorophenyl)amido(dimethyl)methyl-6-phenyl(2'-oxo,3'-phenyl)-pyridine]hafnium dibenzyl
[2-(2,6-diisopropylphenyl)amido(dimethyl)methyl-6-phenyl(2'-oxo,3'-t-butyl)-pyridine]titanium dibenzyl
[2-(2,6-diisopropylphenyl)amido(dimethyl)methyl-6-phenyl(2'-oxo,3'-t-butyl)-pyridine]zirconium dibenzyl
[2-(2,6-diisopropylphenyl)amido(dimethyl)methyl-6-phenyl(2'-oxo,3'-t-butyl)-pyridine]hafnium dibenzyl
[2-(2,4,6-trimethylphenyl)amido(dimethyl)methyl-6-phenyl(2'-oxo,3'-t-butyl)-pyridine]titanium dibenzyl
[2-(2,4,6-trimethylphenyl)amido(dimethyl)methyl-6-phenyl(2'-oxo,3'-t-butyl)-pyridine]zirconium dibenzyl
[2-(2,4,6-trimethylphenyl)amido(dimethyl)methyl-6-phenyl(2'-oxo,3'-t-butyl)-pyridine]hafnium dibenzyl
[2-(2,3,4,5,6-pentafluorophenyl)amido(dimethyl)methyl-6-phenyl(2'-hydroxy,3'-t-butyl)-pyridine]titanium dibenzyl
[2-(2,3,4,5,6-pentafluorophenyl)amido(dimethyl)methyl-6-phenyl(2'-oxo,3'-t-butyl)-pyridine]zirconium dibenzyl
[2-(2,3,4,5,6-pentafluorophenyl)amido(dimethyl)methyl-6-phenyl(2'-oxo,3'-t-butyl)-pyridine]hafnium dibenzyl
[2-(2,6-diisopropylphenyl)amido(dimethyl)methyl-6-phenyl(2'-oxo)-pyridine]titanium bis(dimethylamido)
[2-(2,6-diisopropylphenyl)amido(dimethyl)methyl-6-phenyl(2'-oxo)-pyridine]zirconium bis(dimethylamido)
[2-(2,6-diisopropylphenyl)amido(dimethyl)methyl-6-phenyl(2'-oxo)-pyridine]hafnium bis(dimethylamido)
[2-(2,4,6-trimethylphenyl)amido(dimethyl)methyl-6-phenyl(2'-oxo)-pyridine]titanium bis(dimethylamido)
[2-(2,4,6-trimethylphenyl)amido(dimethyl)methyl-6-phenyl(2'-oxo)-pyridine]zirconium bis(dimethylamido)
[2-(2,4,6-trimethylphenyl)amido(dimethyl)methyl-6-phenyl(2'-oxo)-pyridine]hafnium bis(dimethylamido)
[2-(2,3,4,5,6-pentafluorophenyl)amido(dimethyl)methyl-6-phenyl(2'-oxo)-pyridine]titanium bis(dimethylamido)
[2-(2,3,4,5,6-pentafluorophenyl)amido(dimethyl)methyl-6-phenyl(2'-oxo)-pyridine]zirconium bis(dimethylamido)
[2-(2,3,4,5,6-pentafluorophenyl)amido(dimethyl)methyl-6-phenyl(2'-oxo)-pyridine]hafnium bis(dimethylamido)
[2-(2,6-diisopropylphenyl)amido(dimethyl)methyl-6-phenyl(2'-oxo,3'-phenyl)-pyridine]titanium bis(dimethylamido)
[2-(2,6-diisopropylphenyl)amido(dimethyl)methyl-6-phenyl(2'-oxo,3'-phenyl)-pyridine]zirconium bis(dimethylamido)
[2-(2,6-diisopropylphenyl)amido(dimethyl)methyl-6-phenyl(2'-oxo,3'-phenyl)-pyridine]hafnium bis(dimethylamido)
[2-(2,4,6-trimethylphenyl)amido(dimethyl)methyl-6-phenyl(2'-oxo,3'-phenyl)-pyridine]titanium bis(dimethylamido)
[2-(2,4,6-trimethylphenyl)amido(dimethyl)methyl-6-phenyl(2'-oxo,3'-phenyl)-pyridine]zirconium bis(dimethylamido)
[2-(2,4,6-trimethylphenyl)amido(dimethyl)methyl-6-phenyl(2'-oxo,3'-phenyl)-pyridine]hafnium bis(dimethylamido)
[2-(2,3,4,5,6-pentafluorophenyl)amido(dimethyl)methyl-6-phenyl(2'-hydroxy,3'-phenyl)-pyridine]titanium bis(dimethylamido)
[2-(2,3,4,5,6-pentafluorophenyl)amido(dimethyl)methyl-6-phenyl(2'-oxo,3'-phenyl)-pyridine]zirconium bis(dimethylamido)
[2-(2,3,4,5,6-pentafluorophenyl)amino(dimethyl)methyl-6-phenyl(2'-oxo,3'-phenyl)-pyridine]hafnium bis(dimethylamido)
[2-(2,6-diisopropylphenyl)amido(dimethyl)methyl-6-phenyl(2'-oxo,3'-t-butyl)-pyridine]titanium bis(dimethylamido)
[2-(2,6-diisopropylphenyl)amido(dimethyl)methyl-6-phenyl(2'-oxo,3'-t-butyl)-pyridine]zirconium bis(dimethylamido)
[2-(2,6-diisopropylphenyl)amido(dimethyl)methyl-6-phenyl(2'-oxo,3'-t-butyl)-pyridine]hafnium bis(dimethylamido)
[2-(2,4,6-trimethylphenyl)amido(dimethyl)methyl-6-phenyl(2'-oxo,3'-t-butyl)-pyridine]titanium bis(dimethylamido)
[2-(2,4,6-trimethylphenyl)amido(dimethyl)methyl-6-phenyl(2'-oxo,3'-t-butyl)-pyridine]zirconium bis(dimethylamido)
[2-(2,4,6-trimethylphenyl)amido(dimethyl)methyl-6-phenyl(2'-oxo,3'-t-butyl)-pyridine]hafnium bis(dimethylamido)
[2-(2,3,4,5,6-pentafluorophenyl)amido(dimethyl)methyl-6-phenyl(2'-hydroxy,3'-t-butyl)-pyridine]titanium bis(dimethylamido)
[2-(2,3,4,5,6-pentafluorophenyl)amido(dimethyl)methyl-6-phenyl(2'-oxo,3'-t-butyl)-pyridine]zirconium bis(dimethylamido), and
[2-(2,3,4,5,6-pentafluorophenyl)amido(dimethyl)methyl-6-phenyl(2'-oxo,3'-t-butyl)-pyridine]hafnium bis(dimethylamido).

In a preferred embodiment, in any of the above formulae (except 11 and 12) M is a group 6, 7, 8, 9, or 10 metal, preferably Cr, Mn, Fe, Co, or Ni.

In a preferred embodiment in any of the above formulae:
A) X is selected from the group consisting of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, and allyl; and or
B) R, when present, is hydrogen, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl; and or
C) $R^1$ and $R^2$ are, independently, hydrogen, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, or independently, may join together to form a $C_4$ to $C_{62}$ cyclic or polycyclic ring structure; and or
D) $R^3$, $R^4$, $R^5$, are independently, hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, or independently, may join together to form a $C_4$ to $C_{62}$ cyclic or polycyclic ring structure; and or E) $R^6$ is, independently, hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl; and or F) $R^7$ is independently, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl; and or G) $R^8$ is independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl; and or H) $R^9$ is independently, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl; and or I) $R^{10}$ is independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl; and or J) $R^{11}$ is independently, a hydrogen, a hydrocarbyl, a substituted hydrocarbyl, a halocarbyl, a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl or a group selected from $NO_2$, sulfonate, halo, carboxyl, sulfonyl ester, a carboxylic ester group, or a perfluoroalkyl group; and or K) L' is selected from the group consisting of acetonitrile, diethyl ether, tetrahydrofuran, dimethylaniline, trimethylamine, tributylamine, trimethylphosphine, triphenylphosphine lithium chloride, ethylene, propylene, butene, octene, and styrene; and or L) the halocarbyl or substituted halocarbyl, if present, is a fluorocarbyl or a substituted fluorocarbyl; and or M) in formulae 1, 2, 3, 4, 5, 6, 7, 8, 9, and 10, M is a group 6, 7, 8, 9, or 10 metal, preferably Ni, Co, Fe, Mn, or Cr, OR in formulae 11 and 12 M is a group 4, 5 or 6 metal, preferably Ti, Zr or Hf; and or N) w is 1 and X is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, and allyl.

Mixed Catalysts

Mixed catalyst systems can also be used, for example, the invention catalyst can be used in conjunction with a "second catalyst" in the same reactor or in a series of reactors where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other C2 to C20 olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other C2 to C20 olefins. The "second catalyst" can be of the same family as the invention catalyst, or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Invention polymerization catalyst systems can comprise additional olefin polymerization catalysts, sometimes referred to as the "second catalyst". These additional olefin polymerization catalysts are any of those well known in the art to catalyze the olefin to polyolefin reaction. Some invention catalysts systems include Group-4-6 metallocenes as additional olefin polymerization catalysts. Metallocenes include (un)bridged compounds containing one (mono(cyclopentadienyl)metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937, 299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: monocyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known and can serve as the additional olefin polymerization catalysts with invention catalyst systems.

Invention catalyst systems can use non-cyclopentadienyl, Group-4-5 precursor compounds as the additional olefin polymerization catalysts. Non-cyclopentadienyl, Group-4-5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154-3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478-5480. Synthetic methods and compound characterization are presented. Further work appearing in D. H. McConville, et al, *Macromolecules* 1996, 29, 5241-5243, describes bridged bis (arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors; they are activable with this invention" ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Invention catalyst systems can use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.*, 1995, 117, 6414-6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.*, 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Activators and Catalyst Activation

The catalyst precursors, when activated by a commonly known activator such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such trimethyl aluminum, tri-isobutyl aluminum, triethyl aluminum, and tri-isopropyl aluminum. Co-activators are typically only used in combination with Lewis acid activators and ionic activators when the pre-catalyst is not a dihydrocarbyl or dihydride complex.

The alumoxane component useful as an activator typically is an oligomeric aluminum compound represented by the general formula $(R^x-Al-O)_n$, which is a cyclic compound, or $R^x(R^x-Al-O)_n AlR^x{}_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3\text{-}3,5\text{-}(CF_3)_2))_4]$, $[Ph_3C][B((C_6H_3\text{-}3,5\text{-}(CF_3)_2))_4]$, $[NH_4][B(C_6H_5)_4]$ or Lewis acidic activators such as $B(C_6F_5)_3$ or $B(C_6H_5)_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri (n-butyl) ammonium tetrakis (pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_6)_3$, which upon reaction with the hydrolyzable ligand (X') of the transition metal compound forms an anion, such as ($[B(C_6F_5)_3(X')]^-$), which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

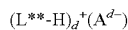

wherein L** is an neutral Lewis base;
H is hydrogen;
(L**-H)$^+$ is a Bronsted acid
$A^{d-}$ is a non-coordinating anion having the charge d–
d is an integer from 1 to 3.

The cation component, $(L^{**}\text{-H})_d^+$ may include Bronsted acids such as protons or protonated Lewis bases or reducible Lewis acids capable of protonating or abstracting a moiety, such as an alkyl or aryl, from the pre-catalyst after alkylation.

The activating cation $(L^{}\text{-H})_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiums from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}\text{-H})_d^+$ may also be a moiety such as silver, tropylium, carbeniums, ferroceniums and mixtures, preferably carboniums and ferroceniums; most preferably triphenyl carbonium.

The anion component $A^{d-}$ include those having the formula $[M^{k+}Q_n]^{d-}$ wherein k is an integer from 1 to 3; n is an integer from 2-6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl) ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (tert-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, trimethylammonium tetrakis(perfluoronaphthyl) borate, triethylammonium tetrakis(perfluoronaphthyl) borate, tripropylammonium tetrakis(perfluoronaphthyl) borate, tri(n-butyl)ammonium tetrakis(perfluoronaphthyl) borate, tri(tert-butyl)ammonium tetrakis(perfluoronaphthyl) borate, N,N-dimethylanilinium tetrakis(perfluoronaphthyl) borate, N,N-diethylanilinium tetrakis(perfluoronaphthyl) borate, N,N-dimethyl-(2,4,6-trimethylanilinium)tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis (trifluoromethyl)phenyl)borate, tri(n-butyl)ammonium tetrakis(3,5-bis(trifluoromethyl)phenyl)borate, tri(tert-butyl) ammonium tetrakis(3,5-bis(trifluoromethyl)phenyl)borate, N,N-dimethylanilinium tetrakis(3,5-bis(trifluoromethyl) phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium)tetrakis(3,5-bis(trifluoromethyl)phenyl)borate.

Most preferably, the ionic stoichiometric activator (L**-H)$_d^+$(A$^{d-}$) is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst precursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Invention process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst precursor and the co-activator. For example, tris(pentafluorophenyl)boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl)boron, and mixtures of trimethyl aluminum with dimethylanilinium tetrakis(pentafluorophenyl)borate or tris(pentafluorophenyl)boron.

In some embodiments, scavenging compounds are used with stoichiometric activators. Typical aluminum or boron alkyl components useful as scavengers are represented by the general formula R$^x$JZ$_2$ where J is aluminum or boron, R$^x$ is as previously defined above, and each Z is independently R$^x$ or a different univalent anionic ligand such as halogen (Cl, Br, I), alkoxide (OR$^x$) and the like. Most preferred aluminum alkyls include triethylaluminum, diethylaluminum chloride, tri-iso-butylaluminum, tri-n-octylaluminum, tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

The solubility of invention catalyst precursors allows for the ready preparation of supported catalysts. To prepare uniform supported catalysts, the catalyst or catalyst precursor preferably dissolves in the chosen solvent. The term "uniform supported catalyst" means that the catalyst, or the catalyst precursor and the activator, and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting pre-catalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 μm is suitable for use in this invention.

Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10-700 $m^2/g$, a pore volume of 0.1-4.0 cc/g and an average particle size of 10-500 μm. Some embodiments select a surface area of 50-500 $m^2/g$, a pore volume of 0.5-3.5 cc/g, or an average particle size of 20-200 μm. Other embodiments select a surface area of 100-400 $m^2/g$, a pore volume of 0.8-3.0 cc/g, and an average particle size of 30-100 μm. Invention carriers typically have a pore size of 10-1000 Angstroms, alternatively 50-500 Angstroms, or 75-350 Angstroms.

Invention catalysts are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1, 3-methylpentene-1, 3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention, particularly with group 4 and 6 metal compounds, include nitro substituted monomers including 6-nitro-1-hexene; amine substituted monomers including N-methylallylamine, N-allylcyclopentylamine, and N-allyl-hexylamine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1,2-diol, 10-undecen-1-ol, 10-undecene-1,2-diol, 2-methyl-3-buten-1-ol; acetal, epoxide and or ether substituted monomers including 4-hex-5-enyl-2,2-dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2-dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-10-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, 2-acetyl-5-norbornene, 7-syn methoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2-tetrafluoroethyl ether, 2,2,3,3-tetrafluoro-non-8-enoic acid ethyl ester, 1,1,2,2-tetrafluoro-2-(1,1,2,2-tetrafluoro-oct-7-enyloxy)-ethanesulfonyl fluoride, acrylic acid 2,2,3,3,4,4,5,5,6,6,7,7,8,8,8-pentadecafluorooctyl ester, and 1,1,2,2-tetrafluoro-2-(1,1,2,2,3,3,4,4-octafluoro-dec-9-enyloxy)-ethanesulfonyl fluoride.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1, 3-methylpentene-1, 3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1, 3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment the copolymers described herein comprise at least 50 mole % of a first monomer and up to 50 mole % of other monomers.

In another embodiment, the polymer comprises:

a first monomer present at from 40 to 95 mole %, preferably 50 to 90 mole %, preferably 60 to 80 mole %, and a comonomer present at from 5 to 60 mole %, preferably 10 to 40 mole %, more preferably 20 to 40 mole %, and a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the pre-catalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system is in liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and or temperature polymerizations to prepare propylene homopolymers and copolymers of propylene with $C_3$ to $C_{10}$ olefins and optionally other copolymerizable olefins have been reported. See U.S. patent applications 60/431,185 filed Dec. 5, 2002; 60/431,077, filed Dec. 5, 2002; and 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, 6,255,410, which are incorporated herein by reference.

Experimental

Preparation of Ligands

The electrospray (ES) mass spectra were recorded using a micromass Quattra LC mass spectrometer with methanol as the matrix [Masslynx software; open-access autosampler injection]. The infrared spectra were recorded as Nujol mulls between 0.5 mm NaCl plates on a Perkin Elmer 1600 series. $^1$H and $^{13}$C NMR spectra were recorded on a Bruker ARX spectrometer 250/300 MHz; chemical shifts (ppm) are referred to the residual protic solvent peaks. The reagents, 2-acetyl-6-phenyl(2'-methoxy)-pyridine, 2-acetyl-6-phenyl(2'-methoxy,3'-phenyl)-pyridine, 2-acetyl-6-phenyl(2'-methoxy,3',5'-di-tert-butyl)-pyridine, formyl-6-phenyl(2'-methoxy)-pyridine and formyl-6-phenyl(2'-methoxy,5'-tert-butyl)-pyridine, were made by unpublished procedures at the University of Leicester. The compound $Pd(PPh_3)_4$ [1] was prepared via a previously reported procedure referenced below. $Pd(PPh_3)_4$ may also be purchased from Aldrich. All other chemicals were obtained commercially and used without further purification.

[1] F. Tellier, R. Sauvetre and J-F. Normant, *J. Organomet. Chem.*, 1985, 292(1-2), 19-28.

EXAMPLES 1-7

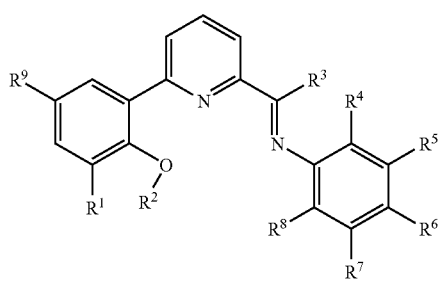

Example 1 (1a): $R^1=R^5=R^6=R^7=R^9=H$; $R^2=R^3=Me$; $R^4=R^8=i-Pr$
Example 2 (1b): $R^1=Ph$; $R^2=R^3=Me$; $R^4=R^8=i-Pr$; $R^5=R^6=R^7=R^9=H$
Example 3 (2a): $R^1=R^2=R^5=R^6=R^7=R^9=H$; $R^3=Me$; $R^4=R^8=i-Pr$
Example 4 (2b): $R^1=Ph$; $R^2=R^5=R^6=R^7=R^9=H$; $R^3=Me$; $R^4=R^8=i-Pr$
Example 5 (2c): $R^1=R^9=t-Bu$; $R^3=Me$; $R^4=R^3=i-Pr$; $R^2=R^5=R^6=R^7=H$
Example 6 (2d): $R^1=R^2=R^3=R^5=R^6=R^7=R^9=H$; $R^4=R^8=i-Pr$
Example 7 (2e): $R^1=R^2=R^3=R^5=R^6=R^7=H$; $R^9=t-Bu$; $R^4=R^8=i-Pr$

EXAMPLES 8-10

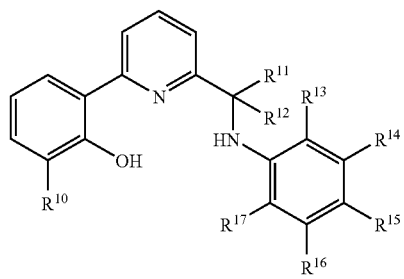

Example 8 (3a): $R^{10}=R^{14}=R^{15}=R^{16}=H$; $R^{11}=R^{12}=Me$; $R^{13}=R^{17}=i-Pr$
Example 9 (3b): $R^{10}=R^{11}=R^{14}=R^{15}=R^{16}=H$; $R^{12}=Me$; $R^{13}=R^{17}=i-Pr$
Example 10 (3c): $R^{10}=Ph$; $R^{11}=R^{14}=R^{15}=R^{16}=H$; $R^{12}=Me$; $R^{13}=R=i-Pr$

EXAMPLE 1

Preparation of 2-acetyl(2,6-diisopropylanil)-6-phenyl (2'-methoxy)-pyridine (1a)

Compound 1a was prepared via the following procedure:

To a solution of 2-acetyl-6-phenyl(2'-methoxy)-pyridine (500 mg, 2.2 mmol) in the minimum volume of absolute ethanol was added 1.5 equivalents of 2,6-diisopropylaniline (0.62 ml, 3.3 mmol). After the addition of a few drops of formic acid, the solution was refluxed overnight. Upon cooling to room temperature the product recrystallized from the ethanol. After filtration the yellow solid was washed with cold ethanol to give $C_5H_3N(CMeN(2,6-i-Pr_2—C_6H_3))(C_6H_4OMe)$ (1a). Yield: 66% (565 mg, 1.46 mmol).

Compound 1a. Melting point 173-177° C. ES mass spectrum: m/z 387 [M+H]$^+$. I.R. (nujol mull, cm$^{-1}$): ν 1644 (C=N). $^1$H NMR (CDCl$_3$, 250 MHz, ppm): δ 1.44 (dd, 12H, $^3J_{H-H}$ 6.8 Hz, $^2J_{H-H}$ 1.9 Hz, CH$_3$), 2.55 (s, 3H, CH$_3$), 3.05 (septet, 2H, $^3J_{H-H}$ 7 Hz, CH), 4.15 (s, 3H, CH$_3$), 7.25-7.5 (m, 5H, CH), 7.65 (dt, 1H, $^3J_{H-H}$ 7.6 Hz, $^4J_{H-H}$ 1.8 Hz, CH), 8.07 (t, 1H, $^3J_{H-H}$ 7.8 Hz, CH), 8.27 (m, 2H, CH), 8.55 (dd, 1H, $^3J_{H-H}$ 7.8 Hz, $^4J_{H-H}$ 0.8 Hz CH). $^{13}$C NMR (CDCl$_3$, 250 MHz, ppm): δ 17.8, 22.9, 23.3, 23.7, 28.7, (CH$_3$ or CH), 39.6 (1C, CH$_3$), 56.1 (1C, CH$_3$), 112.0 (1C, CH), 119.6 (1C, CH), 121.5 (1C, CH), 123.4 (2C, CH), 123.9 (1C, CH), 126.6 (1C, CH), 129.3 (1C, C), 130.5 (1C, CH), 131.8 (1C, CH), 136.3 (1C, CH), 136.5 (1C, C), 147.1 (1C, C), 154.9 (1C, C), 156.4 (1C, C), 157.7 (1C, C) 168.0 (1C, C).

EXAMPLE 2

Preparation of 2-acetyl(2,6-diisopropylanil)-6-phenyl (2'-methoxy,3'-phenyl)-pyridine (1b)

Compound 1b was prepared using an analogous route to that outlined for 1a employing 2-acetyl-6-phenyl(2'-methoxy,3'-phenyl)-pyridine (115 mg, 0.38 mmol) and 1.5 equivalents of 2,6-diisopropylaniline (0.10 cm³, 0.57 mmol). Compound 1b was obtained as a brown solid. Yield: 82% (145 mg, 0.31 mmol).

Compound 1b: Melting point 183-185° C. ES mass spectrum: m/z 463 [M+H]⁺. IR (nujol mull, cm⁻¹): ν 1631 (C=N). ¹H NMR (CDCl₃, 250 MHz, ppm): δ 1.38 (dd, 12H, ³$J_{H-H}$ 6.9 Hz, ²$J_{H-H}$ 1.8 Hz, CH₃), 2.51 (s, 3H, CH₃), 2.99 (septet, 2H, ³$J_{H-H}$ 7 Hz, CH), 3.54 (s, 3H, CH₃), 7.29-7.71 (m, 8H, CH), 7.83 (dd, 2H, CH), 8.10 (m, 2H, CH), 8.3 (dd, 1H, CH), 8.55 (dd, 1H, CH). ¹³C NMR (CDCl₃, 250 MHz, ppm): δ 16.4, 21.9, 22.3, 27.2, (1C, CH₃ or 1C, CH), 38 (1C, CH₃), 60.0 (1C, CH₃), 118.4 (1C, CH), 122.0 (2C, CH), 122.5 (1C, CH), 123.5 (1C, CH), 124.8 (1C, CH), 126.2 (1C, CH), 127.3 ((2C, CH), 128.3 (2C, CH), 129.7 (1C, CH), 130.8 (1C, CH), 133.0 (1C, CH), 134.8 (1C, CH), 134.9 (1C, C), 135.5 (1C, C), 137.6 (1C, C), 145.6 (1C, C), 153.9 (1C, C), 154.7 (1C, C), 155.1 (1C, C), 166.4 (1C, C).

EXAMPLE 3

Preparation of 2-acetyl(2,6-diisopropylanil)-6-phenyl (2'-hydroxy)-pyridine (2a)

Compound 2a was prepared in a two-step procedure:
(i) To a 25 ml round bottom flask equipped with a stir bar and distillation apparatus, concentrated HCl (4.85 ml, 154 mmol) was added to technical grade pyridine (4.5 ml, 57.2 mmol). Water was distilled from the mixture at 250° C. for 4 h to give molten pyridinium chloride. On cooling to 140° C., 2-acetyl-6-phenyl(2'-methoxy)-pyridine (500 mg, 2.2 mmol) was added and the reaction mixture heated to 250° C. for 4 h. After cooling to room temperature, the solution was diluted with an equal volume of water and the pH adjusted to 7 with aqueous NaOH. The aqueous phase was extracted by washing with CHCl₃ (3×50 ml) and dried over MgSO₄. The volatiles were removed under reduced pressure to give 2-(COMe),6-(C₆H₄OH)C₅H₃N as a red solid. Yield: 90% (0.42 g, 1.98 mmol). Compound 2-acetyl-6-phenyl (2'-hydroxy)-pyridine: ES mass spectrum: m/z 214 [M+H]⁺.
(ii) To a solution of 2-acetyl-6-phenyl(2'-hydroxy)-pyridine (1.874 g, 8.8 mmol) in the minimum volume of absolute ethanol was added 1.5 equivalents of 2,6-diisopropylaniline (2.5 ml, 13.0 mmol). After the addition of a few drops of formic acid, the solution was refluxed for 48 h. Upon cooling to room temperature the product crystallized from the ethanol. After filtration the yellow solid was washed with cold ethanol to give C₅H₃N (CMeN(2,6-i-Pr₂—C₆H₃))(C₆H₄OH) (2a). Yield: 80% (2.60 g, 7.0 mmol).

Compound 2a: Melting point: 190-192° C. ES mass spectrum: m/z 373 [M+H]⁺. ¹H NMR (CDCl₃, 250 MHz, ppm): δ 1.08 (dd, 12H, $J_{H-H}$ 6.9 Hz, $J_{H-H}$ 1.7 Hz, CH₃), 2.18 (s, 3H, CH₃), 1.54 (broad s, 1H, OH), 2.65 (septet, 2H, ³$J_{H-H}$ 6.9 Hz, CH), 6.88 (dt, 1H, ³$J_{H-H}$ 6.3 Hz, ⁴$J_{H-H}$ 0.73 Hz, CH), 6.97 (dd, 3H, ³$J_{H-H}$ 6.5 Hz, ⁴$J_{H-H}$ 0.75 Hz, CH), 7.11-7.15 (m, 3H, CH), 7.28 (dt, 1H, ³$J_{H-H}$ 6.6 Hz, ⁴$J_{H-H}$ 0.98 Hz, CH), 7.79 (dd, 1H, ³$J_{H-H}$ 6.9 Hz, ⁴$J_{H-H}$ 1.4 Hz, CH), 7.85-8.00 (m, 2H, CH), 8.23 (dd, ³$J_{H-H}$ 7.1 Hz, ⁴$J_{H-H}$ 1.2 Hz, CH). ¹H NMR (CDCl₃: D₂O, 250 MHz, ppm): δ 1.08 (dd, 12H, ³$J_{H-H}$ 6.9 Hz, CH₃), 2.18 (s, 3H, CH₃), 2.65 (septet, 2H, ³$J_{H-H}$ 6.9 Hz, CH), 6.88 (dt, 1H, ³$J_{H-H}$ 6.3 Hz, ⁴$J_{H-H}$ 0.73 Hz, CH), 6.97 (dd, 3H, ³$J_{H-H}$ 6.5 Hz, ⁴$J_{H-H}$ 0.75 Hz, CH), 7.11-7.15 (m, 3H, CH), 7.28 (dt, 1H, ³$J_{H-H}$ 6.6 Hz, ⁴$J_{H-H}$ 0.98 Hz, CH), 7.79 (dd, 1H, ³$J_{H-H}$ 6.9 Hz, ⁴$J_{H-H}$ 1.4 Hz, CH), 7.85-8.00 (m, 2H, CH), 8.23 (dd, ³$J_{H-H}$ 7.1 Hz, ⁴$J_{H-H}$ 1.2 Hz, CH). ¹³C NMR (CDCl₃, 250 MHz, ppm): δ 16.4, 21.8, 22.2, 27.4 (1C, CH or 1C, CH₃), 38.0 (1C, CH₃), 117.5 (1C, CH), 117.8 (1C, C), 118.1 (1C, CH), 118.4 (1C, CH), 119.3 (1C, CH), 122.1 (1C, CH), 122.9 (1C, CH), 125.4 (1C, CH), 130.7 (1C, CH), 134.7 (2C, C), 137.4 (1C, CH), 144.9 (1C, C), 152.1 (1C, C), 155.6 (1C, C), 158.6 (1C, C), 163.7 (1C, C).

EXAMPLE 4

Preparation of 2-acetyl(2,6-diisopropylanil)-6-phenyl (2'-hydroxy,3'-phenyl)-pyridine (2b)

Compound 2b was prepared in a two-step procedure using:
(i) The deprotection procedure outlined for 2-acetyl-6-phenyl(2'-hydroxy)-pyridine but with 2-acetyl-6-phenyl (2'-methoxy,3'-phenyl)-pyridine (500 mg, 1.65 mmol), compound 2-(COMe),6-(3'-PhC₆H₃OH)C₅H₃N was obtained as a brown oil after heating at 250° C. for 6 h. Yield: 75% (358 mg, 1.24 mmol). Compound 2-acetyl-6-phenyl(2'-hydroxy,3'-phenyl)-pyridine: ES mass spectrum: m/z 290 [M+H]⁺.
(ii) The procedure outlined for 2a but with 2-acetyl-6-phenyl(2'-hydroxy,3'-phenyl)-pyridine (358 mg, 1.24 mmol), 1.5 equivalents of 2,6-diisopropylaniline (0.35 ml, 1.86 mmol) and ethanol as the solvent, compound 2b was obtained as a brown solid. Yield: 61% (339 mg, 0.76 mmol).

Compound 2b: Melting point 197-199° C. ES mass spectrum: m/z 449 [M+H]⁺. IR (nujol mull, cm⁻¹): ν 3387 (OH), 1632 (C=N). ¹H NMR (CDCl₃, 250 MHz, ppm): δ 1.07 (d, 12H, ³$J_{H-H}$ 6.9 Hz, CH₃), 2.15 (s, 3H, CH₃), 2.64 (septet, 2H, ³$J_{H-H}$ 6.9 Hz, CH), 6.92-7.14 (m, 4H, CH), 7.22-7.43 (m, 4H, CH), 7.59 (dd, 2H, ³$J_{H-H}$ 7.1 Hz, CH), 7.79 (dd, 1H, ³$J_{H-H}$ 6.7 Hz, CH), 7.92 (dt, 1H, ³$J_{H-H}$ 7.9 Hz, CH), 8.02 (dd, 1H, ³$J_{H-H}$ 8 Hz, CH), 8.28 (dd, 1H, ³$J_{H-H}$ 7.6 Hz, CH).

EXAMPLE 5

Preparation of 2-acetyl(2,6-diisopropylanil)-6-phenyl (2'-hydroxy,3',5'-di-tert-butyl)-pyridine (2c)

Compound 2c was prepared in a two-step procedure analogous to that outlined for 2a using:
(i) The deprotection procedure given for 2-acetyl-6-phenyl (2'-hydroxy)-pyridine but with 2-acetyl-6-phenyl(2'-methoxy,3',5'-di-tert-butyl)-pyridine, compound 2-(COMe),6-(3',5'-t-Bu₂-PhC₆H₂OH)C₅H₃N was obtained a brown oil after heating at 250° C. for 12 h. Yield: 71% (397 mg, 1.17 mmol). Compound 2-acetyl-6-phenyl(2'-hydroxy,3',5'-di-tert-butyl)-pyridine: ES mass spectrum: m/z 326 [M+H]⁺.
(ii) Compound 2-acetyl-6-phenyl(2'-hydroxy,3',5'-di-tert-butyl)-pyridine (1.00 g, 4.7 mmol), 1.5 equivalents of 2,6-diisopropylaniline (1.40 ml, 7.1 mmol) and ethanol as the solvent, compound 2c was obtained as a brown solid. Yield: 83% (1.23 g, 3.9 mmol).

Compound 2c: ES mass spectrum: m/z 485 [M+H]⁺.

EXAMPLE 6

Preparation of 2-formyl(2,6-diisopropylanil)-6-phenyl(2'-hydroxy)-pyridine (2d)

Compound 2d was prepared in a two-step procedure:
(i) 2-formyl-6-phenyl(2'-methoxy)-pyridine (0.200 g, 0.939 mmol) was dissolved in dry dichloromethane (5 ml) in an oven-dried Schlenk. Boron tribromide (1.98 mmol, 1.98 ml, 1.0M in $CH_2Cl_2$, 2.1 eq.) was added to the solution at −78° C. to afford a dark brown solution. The solution was allowed to warm to room temperature and left to stir for 4 h. Water (5 ml) was carefully added to the solution and the mixture neutralised (with 2M $K_2CO_3$) and then stirred overnight. The organic phase was separated and the aqueous layer washed with chloroform several times until the extracts became colorless. The combined organic layers were dried over $MgSO_4$ and the solvent removed under reduced pressure to afford 2-(CH=O)-6-(2'-OH—$C_6H_4$)$C_5H_3N$ as an orange/brown solid. Yield: 63% (0.117 g, 0.588 mmol).

Compound 2-formyl-6-phenyl(2'-methoxy)-pyridine: FAB mass spectrum: m/z 200 [M+H]⁺. ¹H NMR ($CDCl_3$, 300 MHz, ppm): δ 1.51 (s, br, 1H, OH), 6.89 (t, 1H, Ar—H), 6.99 (d, 1H, Ar—H), 7.29 (t, 1H, Ar—H), 7.72 (d, 1H, Py/Ar—H), 7.80 (d, 1H, Py/Ar—H), 7.91 (t, 1H, Py-H), 8.05 (d, 1H, Py-H), 10.02 (s, 1H, CHO).

(ii) To a solution of 2-formyl-6-phenyl(2'-methoxy)-pyridine (0.100 g, 0.50 mmol) in the minimum volume of absolute ethanol (ca. 3-4 ml) was added 1.2 equivalents of 2,6-diisopropylaniline (0.106 g, 0.60 mmol). The solution was stirred at 50° C. for 5 min. before the addition of one drop of glacial acetic acid. After stirring at 50° C. overnight, the reaction mixture was to cooled to room temperature, the suspension filtered and washed with cold ethanol to give 2-{(2,6-i-$Pr_2C_6H_3$)N=CH}-6-(2'-OH—$C_6H_4$)$C_5H_3N$ (2d) as pale yellow solid Yield: 67% (0.120 g, 0.34 mmol).

Compound 2d: FAB mass spectrum: m/z 359 [M+H]⁺. ¹H NMR ($CDCl_3$, 300 MHz, ppm): δ 1.08 (d, 12H, $^3J_{H-H}$ 6.9 Hz, $CH_3$), 2.87 (septet, 2H, CH), 6.8-7.1 (m, 6H, Ar—H), 7.7-8.1 (m, 4H, Py-H, Ar—H), 8.21 (s, CH=N). ¹³C NMR ($CDCl_3$, 300 MHz, ppm): δ 23.5 (4C, $CH_3$), 28.1 (2C, CH), 118.6 (1C, CH), 118.7 (1C, C), 119.2 (1C, CH), 119.4 (1C, CH), 121.0 (1C, CH), 123.2 (1C, CH), 124.8 (1C, CH), 126.5 (1C, CH), 131.9 (1C, CH), 137.2 (1C, CH), 138.6 (1C, CH), 148.3 (1C, C), 151.0 (1C, C), 158.1 (1C, C), 159.8 (1C, C), 161.1 (1C, HC=N).

EXAMPLE 7

Preparation of 2-formyl(2,6-diisopropylanil)-6-phenyl(2'-hydroxy,5'-tert-butyl)-pyridine (2e)

Compound 2e was prepared in a two-step procedure analogous to that outlined for 2d using:

(i) The deprotection procedure given for 2-formyl-6-phenyl(2'-methoxy)-pyridine but using 2-formyl-6-phenyl (2'-methoxy,5'-tert-butyl)-pyridine, compound 2-(CH=O)-6-(2'-OH,5'-t-$BuC_6H_3$)$C_5H_3N$ was obtained as an orange/brown solid. Yield: 56% (0.230 g, 0.902 mmol).

Compound 2-formyl-6-phenyl(2'-hydroxy,5'-tert-butyl)-pyridine: FAB mass spectrum: m/z 256 [M+H]⁺. ¹H NMR ($CDCl_3$, 300 MHz, ppm): δ 1.29 (s, 9H, C($CH_3$)$_3$), 6.91 (d, 1H, Ar—H), 7.35 (dd, 1H, Ar—H), 7.71 (d, 1H, Ar—H), 7.80 (d, 1H, Py-H), 7.92 (t, 1H, Py-H), 8.10 (d, 1H, Py-H), 10.01 (s, 1H, CHO). ¹³C NMR ($CDCl_3$, 300 MHz, ppm): δ 30.5 (3C, C($CH_3$)$_3$), 33.2 (1C, C($CH_3$)$_3$), 116.3 (1C, C), 117.4 (1C, CH), 118.6 (1C, CH), 121.8 (1C, CH), 122.6 (1C, CH), 128.8 (1C, CH), 137.7 (1C, C), 140.9 (1C, C), 148.4 (1C, C), 156.3 (1C, C), 158.0 (1C, C), 190.1 (C, CHO).

(ii) Compound 2-formyl-6-phenyl(2'-methoxy,5'-tert-butyl)-pyridine (0.100 g, 0.39 mmol) in the minimum volume of absolute ethanol (ca. 3-4 ml) was added 1.2 equivalents of 2,6-diisopropylaniline (0.083 g, 0.47 mmol), compound 2e was obtained as a pale yellow solid.

Yield: 67% (0.101 g, 0.26 mmol).

Compound 2e: FAB mass spectrum: m/z 415 [M+H]⁺. ¹H NMR ($CDCl_3$, 300 MHz, ppm): δ 1.10 (d, 12H, $^3J_{H-H}$ 6.9 Hz, $CH_3$), 1.29 (s, 9H, C($CH_3$)$_3$), 2.86 (septet, 2H, CH), 6.8-7.3 (m, 5H, Ar—H), 7.7-8.1 (m, 4H, Py-H, Ar—H), 8.21 (s, CH=N). ¹³C NMR ($CDCl_3$, 300 MHz, ppm): δ 23.5 (4C, $CH(CH_3)_2$), 28.1 (2C, CH), 31.6 (3C, C($CH_3$)$_3$), 34.2 (1C, C($CH_3$)$_3$), 117.8 (1C, C), 118.2 (1C, CH), 119.1 (1C, CH), 120.9 (1C, CH), 122.9 (1C, CH), 123.2 (1C, CH), 124.8 (1C, CH), 129.3 (1C, CH), 137.2 (1C, CH), 138.5 (1C, CH), 141.7 (1C, C), 148.3 (1C, C), 151.1 (1C, C), 157.4 (1C, CH), 158.1 (1C, C), 161.2 (1C, HC=N).

EXAMPLE 8

Preparation of 2-(2,6-diisopropylphenyl)amino(dimethyl)methyl-6-phenyl(2'-hydroxy)-pyridine (3a)

Compound 3a was prepared in a two-step procedure:

(i) An oven-dried Schlenk flask equipped with a magnetic stir bar was evacuated and backfilled with nitrogen. To the flask charged with 3a (500 mg, 1.34 mmol) dissolved in toluene (15 ml) was introduced two equivalents of $AlMe_3$ (2M solution in toluene, 1.34 ml, 2.69 mmol). The reaction mixture was stirred at reflux for 12 h. After removal of the volatiles under reduced pressure, acetonitrile (15 ml) was added and the suspension refluxed until dissolution. Upon filtration and cooling to room temperature large red crystals of [{$C_5H_3N(CMe_2N(2,6$-i-$Pr_2$—$C_6H_3$))($C_6H_4O$)}AlMe(NCMe)] formed which were filtered and collected.

(ii) Pentane (10 ml) was added to [{$C_5H_3N(CMe_2N(2,6$-i-$Pr_2$—$C_6H_3$))($C_6H_4O$)}AlMe(NCMe)] followed by the dropwise addition of an equal volume of water. After stirring for a further three hours, the aqueous phase was extracted into chloroform (3×20 ml) and dried over $MgSO_4$. The volatiles were removed under reduced pressure to give 3a as a yellow solid. Yield: 75% (390 mg, 1.00 mmol).

Compound 3a: ES mass spectrum: m/z 389 [M+H]⁺. ES mass spectrum: m/z 389 [M+H]⁺. ¹H NMR ($CDCl_3$, 250 MHz, ppm): δ 0.97 (d, 12H, $^3J_{H-H}$ 7.0 Hz, C-$Me_2$), 1.48 (s, 6H, N-$Me_2$), 2.94 (septet, 2H, $^3J_{H-H}$ 7.0 Hz, CH), 6.81 (dt, 1H, $^3J_{H-H}$ 7.5 Hz, $^4J_{H-H}$ 1.4 Hz, CH), 6.91-6.97 (m, 4H, CH), 7.22 (dt, 1H, $^3J_{H-H}$ 7.7 Hz, $^4J_{H-H}$ 1.6 Hz, CH), 7.58 (dd, 1H, $^3J_{H-H}$ 7.0 Hz, $^4J_{H-H}$ 1.8 Hz, CH), 7.72-7.78 (m, 3H, CH). ¹³C NMR ($CDCl_3$, 250 MHz, ppm, ¹H composite pulse decoupled): δ 22.8 (4C, Me), 27.4, 28.2 (2C, Me or CH), 58.1 (1C, C), 115.7 (1C, CH), 117.2 (1C, CH), 117.4 (1C, CH), 117.7 (1C, CH), 118.1 (1C, C), 122.1 (1C, CH), 123.5, (1C, CH), 125.3 (1C, CH), 127.8 (1C, C), 129.9 (1C, C), 130.3 (1C, CH), 137.0 (1C, CH), 138.7 (1C, C), 144.3 (1C, C), 155.5 (1C, C), 159.0 (1C, C), 165.1 (1C, C).

EXAMPLE 9

Preparation of 2-(2,6-diisopropylphenyl)amino(methyl)methyl-6-phenyl(2'-hydroxy)-pyridine (3b)

Compound 3b was prepared via the following procedure:

An oven-dried Schlenk flask equipped with a magnetic stir bar was evacuated and backfilled with nitrogen. To the flask charged with 2a (500 mg, 1.3 mmol) dissolved in diethyl ether (15 ml) at −78° C. was added dropwise LiAlH$_4$ (1.95 ml, 1.95 mmol, 1M solution in diethyl ether) in diethyl ether 20 ml at −10° C. The reaction mixture was warmed to rt and stirred for 0.5 h. The reaction was quenched by the slow addition of water (5 ml). The aqueous phase was extracted by washing with CHCl$_3$ (3×25 ml) and dried over MgSO$_4$. The volatiles were removed under reduced pressure to give 2-{(2,6-i-Pr$_2$C$_6$H$_3$)NCMeH}-6-(2'-OH-5'-t-Bu-C$_6$H$_3$)C$_5$H$_3$N (3b) as a yellow solid. Yield: 80% (389 mg, 1.04 mmol).

Compound 3b: ES mass spectrum: m/z 375 [M+H]$^+$.

EXAMPLE 10

Preparation of 2-(2,6-diisopropylphenyl)amino(methyl)methyl-6-phenyl(2'-hydroxy,3'-phenyl)-pyridine (3c)

Compound 3c was prepared in a two-step procedure analogous to that outlined for 3b but employing 2b (500 mg, 1.1 mmol) and 1.5 equivalents of LiAlH$_4$ (1M solution in diethyl ether, 1.7 ml, 1.7 mmol). Following work-up, 3c was obtained as a yellow solid. Yield: 74% (366 mg, 0.81 mmol).

Compound 3c: ES mass spectrum: m/z 351 [M+H]$^+$.

Preparation of Complexes

All complexation reactions were carried out under an atmosphere of dry, oxygen-free nitrogen, using standard Schlenk techniques or in a nitrogen purged glove box. n-Butanol and thf were dried and deoxygenated by distillation over sodium metal under nitrogen. The metal dichlorides were purchased from Aldrich Chemical Co. and used without any further purification. The metal precursor FeCl$_2$(thf)$_2$ was prepared via methods reported in the literature. FAB mass spectra were recorded using a Kratos Concept spectrometer with NBA (nitrobenzyl alcohol) as the matrix [samples placed on the end of probe within matrix and bombarded with xenon atoms at ca. 7 kV; Mach3 software, probe temperature 50° C.]. Elemental analyses were performed by S. Boyer at the Department of Chemistry, University of North London (UK). Data for the crystal structure determinations were collected on a Bruker APEX 2000 CCD diffractometer and solved using SHELXTL version 6.10. Magnetic susceptibility studies were performed using an Evans Balance at ambient temperature.

[2] D. Astruc and J. R. Morow, *Bull. Chem. Soc. Fr.* 1992, 129, 319-328.

EXAMPLES 11, 12, 15, 16, 19, 20

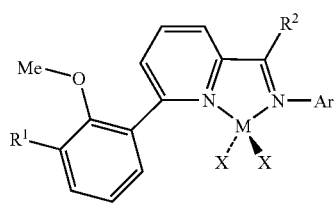

Example 11 (4a): R$^1$=H; R$^2$=Me; Ar=2,6-i-Pr$_2$—C$_6$H$_3$; X=Cl; M=Fe
Example 12 (4b): R$^1$=Ph; R$^2$=Me; Ar=2,6-i-Pr$_2$—C$_6$H$_3$; X=Cl; M=Fe
Example 15 (5a): R$^1$=H; R$^2$=Me; Ar=2,6-i-Pr$_2$—C$_6$H$_3$; X=Cl; M=Co
Example 15 (5b): R$^1$=Ph; R$^2$=Me; Ar=2,6-i-Pr$_2$—C$_6$H$_3$; X=Cl; M=Co
Example 19 (6a): R$^1$=H; R$^2$=Me; Ar=2,6-i-Pr$_2$—C$_6$H$_3$; X=Cl; M=Ni
Example 20 (6b): R$^1$=Ph; R$^2$=Me; Ar=2,6-i-Pr$_2$—C$_6$H$_3$; X=Cl; M=Ni

EXAMPLES 13, 14, 17, 18, 21, 22

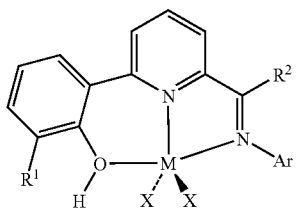

Example 13 (4c): R$^1$=H; R$^2$=Me; Ar=2,6-i-Pr$_2$—C$_6$H$_3$; X=Cl; M=Fe
Example 14 (4d): R$^1$=Ph; R$^2$=Me; Ar=2,6-i-Pr$_2$—C$_6$H$_3$; X=Cl; M=Fe
Example 17 (5c): R$^1$=H; R$^2$=Me; Ar=2,6-i-Pr$_2$—C$_6$H$_3$; X=Cl; M=Co
Example 18 (5d): R$^1$=Ph; R$^2$=Me; Ar=2,6-i-Pr$_2$—C$_6$H$_3$; X=Cl; M=Co
Example 21 (6c): R$^1$=H; R$^2$=Me; Ar=2,6-i-Pr$_2$—C$_6$H$_3$; X=Cl; M=Ni
Example 22 (6d): R$^1$=Ph; R$^2$=Me; Ar=2,6-i-Pr$_2$—C$_6$H$_3$; X=Cl; M=Ni

EXAMPLES 23, 25, 27, 28

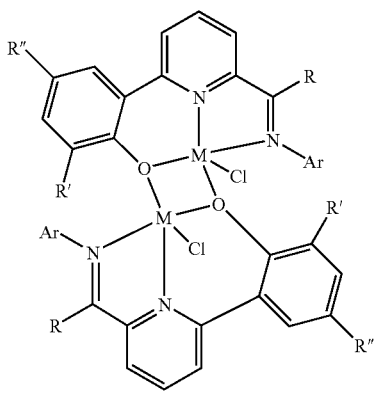

Example 23 (7a): R=Me, R'=R"=H; Ar=2,6-i-Pr$_2$—C$_6$H$_3$; X=Cl; M=Fe
Example 25 (8a): R=Me, R'=R"=H; Ar=2,6-i-Pr$_2$—C$_6$H$_3$; X=Cl; M=Co
Example 27 (8c): R=R'=R"=H; Ar=2,6-i-Pr$_2$—C$_6$H$_3$; X=Cl; M=Co
Example 28 (8d): R=Me, R"=t-Bu; Ar=2,6-i-Pr$_2$—C$_6$H$_3$; X=Br; M=Co

EXAMPLE 24, 26, 29

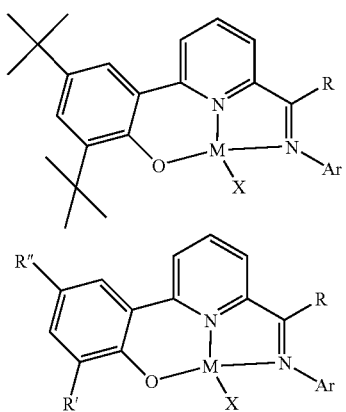

Example 24 (7b): R=Me, R'=Ph, R''=H; Ar=2,6-i-Pr$_2$—C$_6$H$_3$; X=Cl; M=Fe
Example 26 (8b): R=Me, R'=Ph, R''=H; Ar=2,6-i-Pr$_2$—C$_6$H$_3$; X=Cl; M=Co
Example 29 (8e): R=Me; R'=R''=t-Bu; Ar=2,6-i-Pr$_2$—C$_6$H$_3$; X=Cl; M=Co

EXAMPLE 11

Preparation of {2-acetyl(2,6-diisopropylanil)-6-phenyl(2'-methoxy)-pyridine}FeCl$_2$ (4a)

A solution of 1a (673 mg, 1.74 mmol) in n-butanol was added to a solution of FeCl$_2$ (221 mg, 1.74 mmol) in n-butanol (20 cm$^3$) at 90° C. to form a red solution. After being stirred at 90° C. for 1 h, the reaction was allowed to cool to room temperature. The reaction mixture was concentrated and hexane added to induce precipitation of 4a as a red solid. The suspension was stirred overnight, filtered, washed with hexane (2×30 cm$^3$) and dried under reduced pressure.
Yield: 78% (700 mg, 1.40 mmol). Complex 4a: FAB mass spectrum: m/z 512 [M]$^+$, 477 [M–Cl]$^+$. Crystals of 4a suitable for single crystal X-ray diffraction study were obtained from a chloroform solution (FIG. 1).

EXAMPLE 12

Preparation of {2-acetyl(2,6-diisopropylanil)-6-phenyl(2'-methoxy,3'-phenyl)-pyridine}FeCl$_2$ (4b)

Compound 4b was prepared as red solid using an analogous route to that outlined for 4a employing FeCl$_2$ (19 mg, 0.15 mmol), 1b (65 mg, 0.15 mmol) and n-butanol as the solvent.
Yield: 88% (78 mg, 0.13 mmol). Complex 4b: FAB mass spectrum: m/z 590 [M]$^+$, 553 [M–Cl]$^+$.

EXAMPLE 13

Preparation of {2-acetyl(2,6-diisopropylanil)-6-phenyl(2'-hydroxy)-pyridine}FeCl$_2$ (4c)

Compound 4c was prepared as a dark red solid using an analogous route to that outlined for 4a employing FeCl$_2$ (51 mg, 0.40 mmol), 2a (149 mg, 0.40 mmol) and n-butanol as the solvent.
Yield: 66% (132 mg, 0.26 mmol). Complex 4c: FAB mass spectrum: m/z 497 [M]$^+$, 462 [M–Cl]$^+$.

EXAMPLE 14

Preparation of {2-acetyl(2,6-diisopropylanil)-6-phenyl(2'-hydroxy,3'-phenyl)-pyridine}FeCl$_2$ (4d)

Compound 4d was prepared as a dark red solid in analogous route to that outlined for 4a employing FeCl$_2$ (28 mg, 0.22 mmol), 2b (99 mg, 0.22 mmol) and n-butanol as the solvent.
Yield: 83% (105 mg, 0.18 mmol). Complex 4d: FAB mass spectrum: m/z 538 [M–Cl]$^+$, 503 [M–2Cl]$^+$.

EXAMPLE 15

Preparation of {2-acetyl(2,6-diisopropylanil)-6-phenyl(2'-methoxy)-pyridine}CoCl$_2$ (5a)

Compound 5a was prepared as a green solid using an analogous route to that outlined for 4a from CoCl$_2$ (30 mg, 0.23 mmol), 1a (92 mg, 0.23 mmol) and n-butanol as the solvent.
Yield: 34% (40 mg, 68 μmol). Complex 5a: FAB mass spectrum: m/z 480 [M–Cl]$^+$.

Figure 2:
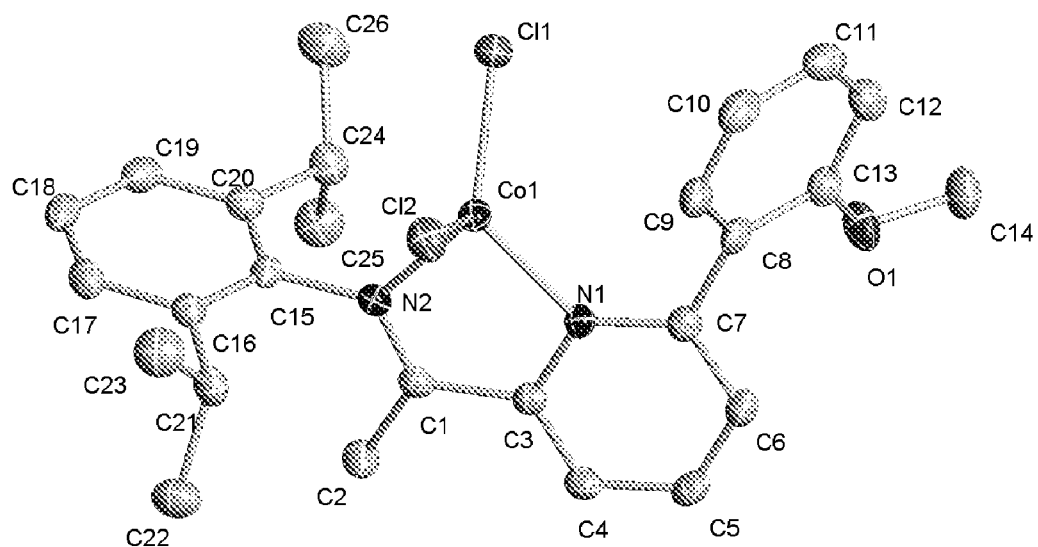

Crystals of 5a suitable for single crystal X-ray diffraction study were obtained from a chloroform solution (FIG. 2).

EXAMPLE 16

Preparation of {2-acetyl(2,6-diisopropylanil)-6-phenyl(2'-methoxy-3'-phenyl)-pyridine}CoCl$_2$ (5b)

Compound 5b was prepared as a green solid using an analogous route to that outlined for 4a employing CoCl$_2$ (20 mg, 0.15 mmol), 1b (71 mg, 0.15 mmol) and n-butanol as the solvent.
Yield: 89% (79 mg, 0.13 mmol). Complex 5b: FAB mass spectrum: m/z 556 [M–Cl]$^+$.

EXAMPLE 17

Preparation of {2-acetyl(2,6-diisopropylanil)-6-phenyl(2'-hydroxy)-pyridine}CoCl$_2$ (5c)

Figure 3:
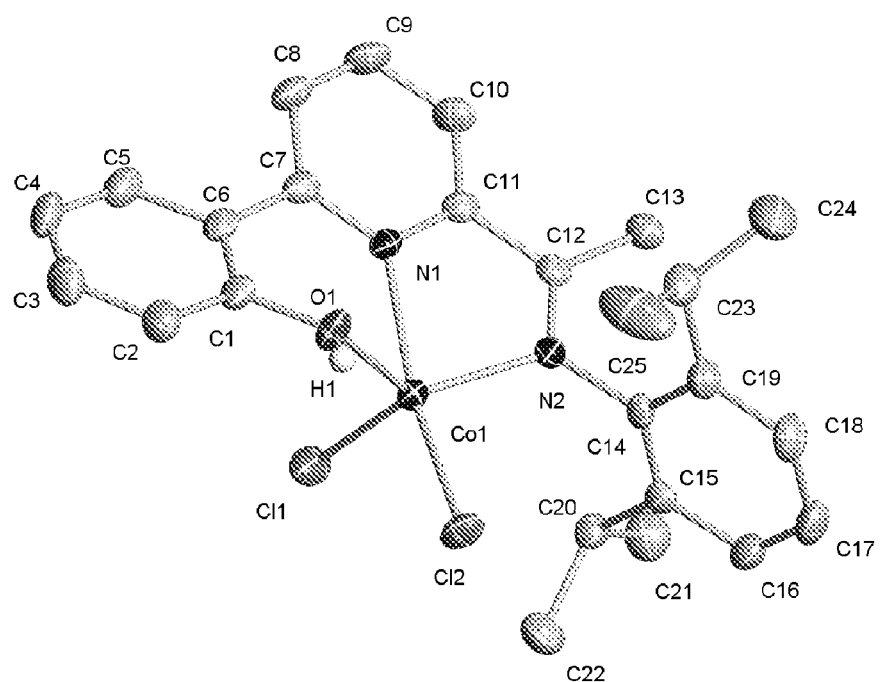
FIG. 3 is a drawing of the molecular structure of compound 5c.

A solution of 2a (149 mg, 0.40 mmol) in thf (10 ml) was added to a suspension of CoCl$_2$ (52 mg, 0.40 mmol) in thf (5 ml) at rt to form a green solution. After being stirred overnight at rt the reaction mixture was concentrated and hexane added to induce precipitation of 5c as a green solid. The suspension was stirred overnight, filtered, washed with hexane (2×30 ml) and dried under reduced pressure. Yield: 67% (135 mg, 0.27 mmol).
Complex 5c: FAB mass spectrum: m/z 465 [M–Cl]$^+$, 430 [M–2Cl]$^+$ Crystals of 5c suitable for single crystal X-ray diffraction study were obtained the slow cooling of a hot acetonitrile solution (FIG. 3).

EXAMPLE 18

Preparation of {2-acetyl(2,6-diisopropylanil)-6-phenyl(2'-hydroxy-3'-phenyl)-pyridine}CoCl$_2$ (5d)

Compound 5d was prepared as a green solid using an analogous route to that outlined for 4a employing CoCl$_2$ (29 mg, 0.22 mmol), 2b (99 mg, 0.22 mmol) and n-butanol as the solvent.

Yield: 85% (108 mg, 0.19 mmol). Complex 5d: FAB mass spectrum: m/z 543 [M−Cl]$^+$.

EXAMPLE 19

Preparation of {2-acetyl(2,6-diisopropylanil)-6-phenyl(2'-methoxy)-pyridine}NiCl$_2$ (6a)

Compound 6a was prepared as a brown solid using an analogous route to that outlined for 4a employing NiCl$_2$ (30 mg, 0.23 mmol), 1a (89 mg, 0.23 mmol) and n-butanol as the solvent.

Yield: 29% (35 mg, 68 μmol). Complex 6a: FAB mass spectrum: m/z 479 [M−Cl]$^+$.

EXAMPLE 20

Preparation of {2-acetyl(2,6-diisopropylanil)-6-phenyl(2'-methoxy,3'-phenyl)-pyridine}NiCl$_2$ (6b)

Compound 6b was prepared as a brown solid using an analogous route to that outlined for 4a employing NiCl$_2$ (20 mg, 0.15 mmol), 1b (70 mg, 0.15 mmol) and n-butanol as the solvent.

Yield: 79% (70 mg, 0.12 mmol). Complex 6b: FAB mass spectrum: m/z 555 [M−Cl]$^+$.

EXAMPLE 21

Preparation of {2-acetyl(2,6-diisopropylanil)-6-phenyl(2'-hydroxy)-pyridine}NiCl$_2$ (6c)

Compound 6c was prepared as a brown solid using an analogous route to that outlined for 4a employing NiCl$_2$ (52 mg, 0.40 mmol), 2a (149 mg, 0.40 mmol) and n-butanol as the solvent.

Yield: 62% (125 mg, 0.25 mmol). Complex 6c: FAB mass spectrum: m/z 429 [M−2Cl]$^+$.

EXAMPLE 22

Preparation of {2-acetyl(2,6-diisopropylanil)-6-phenyl(2'-hydroxy,3'-phenyl)-pyridine}NiCl$_2$ (6d)

Compound 6d was prepared as a brown solid using an analogous route to that outlined for 4a employing NiCl$_2$ (36 mg, 0.28 mmol), 2b (126 mg, 0.28 mmol) and n-butanol as the solvent.

Yield: 89% (145 mg, 0.25 mmol). Complex 6d: FAB mass spectrum: m/z 543 [M−Cl]$^+$.

EXAMPLE 23

Preparation of [{2-acetyl(2,6-diisopropylanil)-6-phenyl(2'-oxo)-pyridine}FeCl]$_2$ (7a)

An oven-dried Schlenk flask equipped with a magnetic stir bar was evacuated and backfilled with nitrogen. The flask was charged with 2a (100 mg, 0.27 mmol) in thf (10 cm$^3$) and NaH (20 mg, 0.81 mmol) was added to form a yellow solution. After being stirred at 70° C. for 16 h, the reaction mixture was filtered into a Schlenk flask containing FeCl$_2$(thf)$_2$ (82 mg, 0.27 mmol) and stirred at rt for 4 h. The reaction mixture was concentrated and hexane added to induce precipitation of [{2-(CMeN(2,6-i-Pr$_2$C$_6$H$_3$)),6-(C$_6$H$_4$O)C$_5$H$_3$N}FeCl]$_2$ (7a) as a dark red solid. The suspension was washed with hexane (2×30 ml) and dried under reduced pressure. Recrystallisation from hot acetonitrile gave 7a as a dark red microcrystalline powder.

Yield: 70% (92 mg, 0.10 mmol). Complex 7a: FAB mass spectrum: m/z 889 [M−Cl]$^+$, 427 [M/2−Cl]$^+$.

EXAMPLE 24

Preparation of [{2-acetyl(2,6-diisopropylanil)-6-phenyl(2'-oxo,3'-phenyl)-pyridine}FeCl] (7b)

Compound 7b was prepared as a red solid using an analogous route to that outlined for 7a employing 2b (130 mg, 0.29 mmol), NaH (21 mg, 0.87 mmol), FeCl$_2$ (37 mg, 0.29 mmol), and thf as the solvent.

Yield: 75% (117 mg, 0.22 mmol). Complex 7b: FAB mass spectrum: m/z 539 [M]$^+$, 504 [M−Cl]$^+$.

EXAMPLE 25

Preparation of [{2-acetyl(2,6-diisopropylanil)-6-phenyl(2'-oxo)-pyridine}CoCl]$_2$ (8a)

Compound 8a was prepared as a green solid using an analogous route to that outlined for 7a employing 2a (126 mg, 0.27 mmol), NaH (20 mg, 0.81 mmol), CoCl$_2$ (35 mg, 0.27 mmol), and thf as the solvent.

Yield: 80% (108 mg, 0.11 mmol). Complex 8a: FAB mass spectrum: m/z 895 [M−Cl]$^+$, 430 [M/2−Cl]$^+$.

Figure 4:
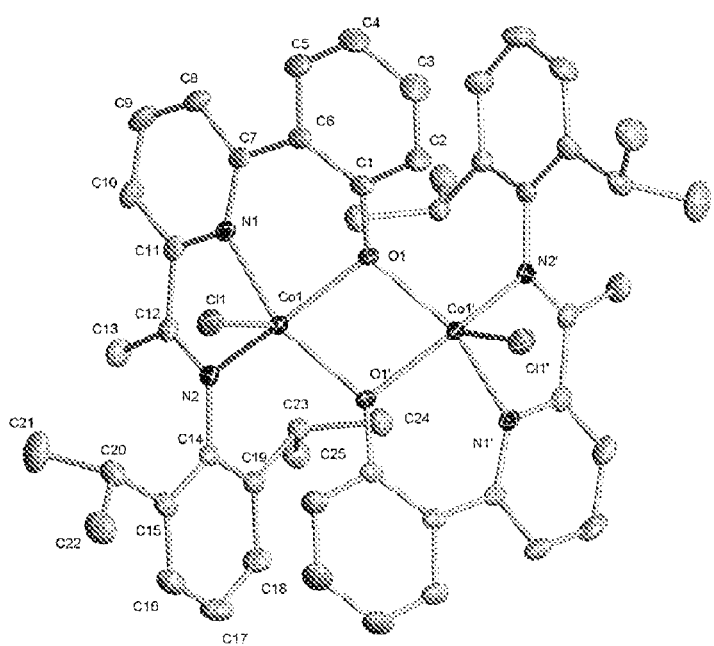

Red crystals of 8a suitable for a single crystal X-ray diffraction study were obtained from the slow cooling of a hot acetonitrile solution (FIG. 4).

EXAMPLE 26

Preparation of [{2-acetyl(2,6-diisopropylanil)-6-phenyl(2'-oxo,3'-phenyl)-pyridine}CoCl] (8b)

Compound 8b was prepared as a green solid using an analogous route to that outlined for 7a employing 2b (130 mg, 0.29 mmol), NaH (21 mg, 0.87 mmol), CoCl$_2$ (37 mg, 0.29 mmol), and thf as the solvent.

Yield: 80% (132 mg, 0.23 mmol). Complex 8b: FAB mass spectrum: m/z 542 [M]$^+$, 506 [M−Cl]$^+$.

EXAMPLE 27

Preparation of [{2-formyl(2,6-diisopropylanil)-6-phenyl(2'-oxo)-pyridine}CoCl]$_2$ (8c)

An oven-dried Schlenk flask equipped with a magnetic stir bar was evacuated and backfilled with nitrogen. The flask was charged with CoCl$_2$ (36 mg, 0.28 mmol) and dissolved in n-butanol (10 ml) at 90° C. Compound 2d (90 mg, 0.25 mmol) was introduced and the reaction mixture stirred at 90° C. for 30 min. The reaction mixture was concentrated and hexane added to induce precipitation of [{2-(CHN(2,6-i-Pr$_2$C$_6$H$_3$))6-(C$_6$H$_4$O)C$_5$H$_3$N}CoCl]$_2$ (8c) as a red/green solid. The green suspension was stirred overnight, filtered, washed with hexane (2×30 ml) and dried under reduced pressure.

Yield: 80% (98 mg, 0.11 mmol). Complex 8c: FAB mass spectrum: m/z 867 [M−Cl]$^+$, 416 [M/2−Cl]$^+$.

Figure 5:
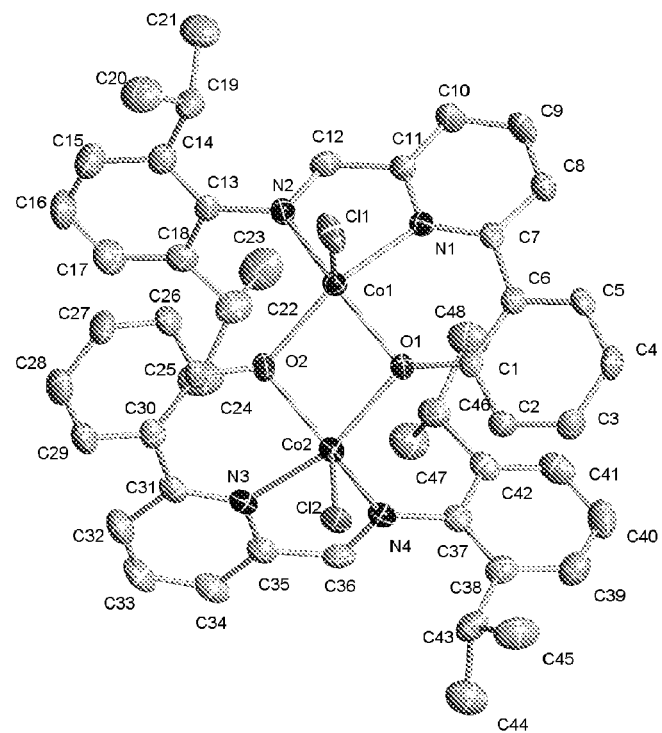
FIG. 5 is a drawing of the molecular structure of compound 8c.

Red crystals of 8c suitable for a single crystal X-ray diffraction study were obtained from the slow cooling of a hot acetonitrile solution (FIG. 5).

EXAMPLE 28

Preparation of [{2-formyl(2,6-diisopropylanil)-6-phenyl(2'-oxo,5'-t-butyl)-pyridine}CoBr]$_2$ (8d)

An oven-dried Schlenk flask equipped with a magnetic stir bar was evacuated and backfilled with nitrogen. The flask was charged with CoCl$_2$ (55 mg, 0.43 mmol) and dissolved in n-butanol (10 ml) at 90° C. Compound 2e (0.15 mg, 0.35 mmol) was introduced and the reaction mixture stirred at 90° C. for 30 min. The reaction mixture was concentrated and hexane added to induce precipitation of [{2-(CHN(2,6-i-Pr$_2$C$_6$H$_3$))6-(5'-t-BuC$_6$H$_3$O)C$_5$H$_3$N}CoBr]$_2$ (8d) as a red/green solid. The green suspension was stirred overnight, filtered, washed with hexane (2×30 ml) and dried under reduced pressure.

Yield: 80% (98 mg, 0.11 mmol). Complex 8d: FAB mass spectrum: m/z 1036 [M−Br]$^+$.

Figure 6:
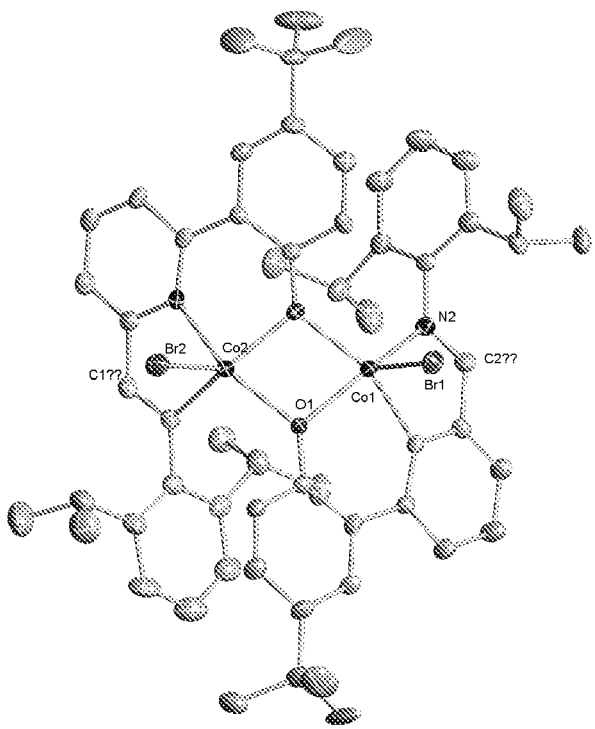
FIG. 6 is a drawing of the molecular structure of compound 8d.

Red crystals of 8d suitable for a single crystal X-ray diffraction study were obtained from the slow cooling of a hot acetonitrile solution (FIG. 6).

EXAMPLE 29

Preparation of {2-acetyl(2,6-diisopropylanil)-6-phenyl(2'-oxo,3',5'-di-tert-butyl)-pyridine}CoCl (8e)

An oven-dried Schlenk flask equipped with a magnetic stir bar was evacuated and backfilled with nitrogen. The flask was charged with 2c (130 mg, 0.27 mmol) in ethanol (10 ml) and NaOMe (37 mg, 0.68 mmol) was added to form a yellow solution. After being stirred at 90° C. for 24 h, the reaction mixture was filtered into a schlenk flask containing CoCl$_2$ (35 mg, 0.27 mmol) and stirred at 60° C. for 12 h. The reaction mixture was concentrated and hexane added to induce precipitation of [{2-(CMeN(2,6-i-Pr$_2$C$_6$H$_3$))6-(3',5'-t-Bu$_2$-C$_6$H$_4$O)C$_5$H$_3$N}CoCl (8e) as a green solid. The suspension was stirred overnight, filtered, washed with hexane (2×30 ml) and dried under reduced pressure.

Yield: 65% (110 mg, 0.18 mmol). Complex 8e: FAB mass spectrum: m/z 578 [M−Cl]$^+$.

Schlenk Test Polymerizations

The reagents used in the polymerization tests were Ethylene Grade 3.5 (supplied from BOC), toluene (dried and deoxygenated by distillation over sodium metal under nitrogen, supplied by Fisher) and methylaluminoxane (MAO, 10% wt solution in toluene, supplied by Aldrich).

EXAMPLE 30

Schlenk Test

The complexes 4a and 4c made in Examples 11 and 14 were dissolved or suspended in toluene (40 cm$^3$) and MAO introduced. The schlenk flask was purged with ethylene and the contents stirred under one bar of ethylene pressure at 25° C. for the duration of the polymerization. After 0.5 h the polymerization was terminated by the addition of aqueous hydrogen chloride. The solid produced was filtered off, washed with methanol and dried in a vacuum oven at 50° C.

TABLE 1

Schlenk test runs using complexes 4a and 4c[a].

| Run | Pre-catalyst (mmol) | Activator[b] (mmol/equiv.) | C2 Pressure (bar) | Polymer (g)[c] | Activity (g/mmol/h/bar) |
|---|---|---|---|---|---|
| 1 | 4a (0.010) | MAO (10/200) | 1 | 0.029 | 6 |
| 2 | 4a (0.010) | MAO (10/1000) | 1 | 0.011 | 2 |
| 3 | 4c (0.010) | MAO (10/200) | 1 | trace | trace |
| 4 | 4c (0.010) | MAO (10/1000) | 1 | | |

[a]General Conditions: Toluene solvent (40 cm$^3$), 25° C., reaction time 0.5 h, ethylene pressure 1 bar, reaction quenched with dil. HCl;
[b]MAO = methylaluminoxane;
[c]Solid washed with methanol (50 cm$^3$) and dried in vacuum oven at 50° C.

Ethylene Parallel Polymerization Reactor (PPRA)

The reagents used in the polymerization tests were toluene, ethylene (polymerization grade) which, were purified by passing through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves (Aldrich Chemical Company) and methylaluminoxane (MAO, 10% wt in toluene), from Albamarle Corporation.

For analytical testing, polymer sample solutions were prepared by dissolving in 2,6-di-tert-butyl-4-methylphenol (BHT, 99% purity was purchased from Aldrich) stabilized polymer in 1,2,4-trichlorobenzene (TCB 99+% purity from Aldrich; 5 gm of BHT in 4 L of TCB), at 160° C. in a shaker oven for approximately 3 hours. The typical concentration of polymer in solution is between 0.4 to 0.9 mg/ml. Samples cooled to 135° C. for GPC testing.

Molecular weights, weight average molecular weight (Mw), number average molecular weight (Mn) and molecular weight distribution (MWD=Mw/Mn), which is also sometimes referred to as the polydispersity index (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples were run in TCB at (135° C. sample temperatures, 160° C. oven/columns) using three Polymer Laboratories: PLgel 10 μm Mixed-B 300×7.5 mm columns in series. No column spreading corrections were employed. Numerical analyses were performed using Epoch® software available from Symyx Technologies.

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes's MappIR specular reflectance sample accessory. Spectra, covering a spectral range of 5000 cm$^{-1}$ to 500 cm$^{-1}$, were collected at a 2 cm$^{-1}$ resolution with 32 scans.

For ethylene octene copolymers, the wt. % copolymer is determined via measurement of the methyl deformation band at ~1375 cm$^{-1}$. The peak height of this band is normalized by the combination and overtone band at ~4321 cm$^{-1}$, which corrects for path length differences. The normalized peak height is correlated to individual calibration curves from H-NMR data to predict the wt. % copolymer content within a concentration range of ~2 to 35 wt. % for octene. Typically, $R^2$ correlations of 0.98 or greater are achieved.

EXAMPLE 31

PPRA Screening

Polymerizations were performed in glass-lined 23.5 ml reactors equipped with disposable PEEK mechanical stirrers, an external heater for temperature control, septum inlet regulated supply of nitrogen and ethylene, in a nitrogen purged glove box. The complexes 4a, 4b, 4c, 4d, 5d and 6d were employed in runs 1-179. The reactor was dried and degassed at 115° C. for 5 h and then purged with nitrogen at room temperature for another 5 h. It was finally purged with ethylene. A mixture of toluene, octene and MAO (source Albamarle 10% wt in toluene, % wt altered when necessary) was added at rt, followed by heating the reactor to process temperature 40-75° C. while stirring at 800 rpm. The pre-catalyst dissolved in chlorobenzene (0.1 ml, 0.2 mM), was injected at process conditions. Ethylene was fed to the reactor on demand to keep pressure constant at 50-250 psig (dependent upon run). The reaction was quenched with 5 mol % Oxygen in Argon after the total duration of one hour or a predetermined amount of ethylene had been consumed (20 psig). The reactor was then cooled, vented and the polymer recovered by vacuum centrifugation of the reaction mixture. The catalysts were validated with the literature precedent [2,6-i-PrC$_6$H$_3$N=C(Me)-C(Me)=N2,6-i-PrC$_6$H$_3$]NiBr$_2$ and [2,6-(2',6'-i-PrC$_6$H$_3$N)$_2$C$_5$H$_3$N]FeCl$_2$ complexes and MAO as activator.

TABLE 2

PPRA evaluation with complexes 4a, 4b, 4c, 4d, 5d and 6d[a].

| Run/Cat (μmol)[a/b] | Activator[c] (μmol/eq.) | Time/s | T/° C. | P/bar[d] | Mw[e] | Wt % Oct | mmol Oct | Yield/g | Activity g/mmol/h | Activity g/mmol/h/bar |
|---|---|---|---|---|---|---|---|---|---|---|
| 1/4a (0.8) | MAO (80/100) | 1526 | 40.1 | 17.2 | 376221 | — | 0 | 0.1153 | 339.962 | 19.7 |
| 2/4a (0.8) | MAO (80/100) | 1321 | 40.5 | 17.2 | 330173 | — | 0 | 0.2427 | 826.71 | 48.0 |
| 3/4a (0.8) | MAO (80/100) | 1942 | 40.3 | 17.2 | 325866 | — | 0 | 0.1884 | 436.495 | 25.3 |
| 4/4a (0.8) | MAO (80/100) | 659 | 40 | 10.3 | 198191 | — | 0 | 0.0404 | 275.764 | 26.8 |
| 5/4a (0.8) | MAO (80/100) | 586 | 40.2 | 10.3 | 200833 | — | 0 | 0.0613 | 470.903 | 45.5 |
| 6/4a (0.8) | MAO (80/100) | 668 | 40.2 | 10.3 | 182918 | — | 0 | 0.0438 | 295.055 | 28.5 |
| 7/4a (0.4) | MAO (40/100) | 3600 | 40.1 | 3.45 | 296351 | — | 0 | 0.0434 | 108.494 | 31.48 |
| 8/4a (0.4) | MAO (40/100) | 3601 | 39.9 | 3.45 | 355798 | — | 0 | 0.044 | 109.962 | 31.9 |
| 9/4a (0.4) | MAO (40/100) | 3600 | 40.1 | 3.45 | 296505 | — | 0 | 0.0215 | 53.7375 | 15.6 |
| 10/4a (0.8) | MAO (80/100) | 3601 | 75 | 17.2 | 80625 | — | 0 | 0.0339 | 42.3608 | 2.46 |
| 11/4a (0.8) | MAO (80/100) | 3601 | 75 | 17.2 | 94783 | — | 0 | 0.0279 | 34.8697 | 2.02 |
| 12/4a (0.8) | MAO (80/100) | 2657 | 75 | 17.2 | 54112 | — | 0 | 0.0466 | 78.9325 | 4.58 |
| 13/4a (0.4) | MAO (40/100) | 1832 | 75.1 | 10.3 | 40507 | — | 0 | 0.046 | 225.964 | 21.9 |
| 14/4a (0.4) | MAO (40/100) | 1347 | 75.1 | 10.3 | 36818 | — | 0 | 0.052 | 347.444 | 33.6 |
| 15/4a (0.4) | MAO (40/100) | 2005 | 74.9 | 10.3 | 45172 | — | 0 | 0.0437 | 196.13 | 18.97 |
| 16/4a (0.4) | MAO (40/100) | 3601 | 75.1 | 3.45 | — | — | 0 | 0.0028 | 6.99833 | 2.03 |
| 17/4a (0.4) | MAO (40/100) | 3601 | 75 | 3.45 | — | — | 0 | 0.0031 | 7.7469 | 2.25 |
| 18/4a (0.4) | MAO (40/100) | 3600 | 74.9 | 3.45 | 41412 | — | 0 | 0.029 | 72.4915 | 21.0 |
| 19/4a (0.4) | MAO (40/100) | 3601 | 75.1 | 10.3 | 60137 | 5.1 | 6.37 | 0.0196 | 48.9826 | 4.746 |
| 20/4a (0.8) | MAO (80/100) | 1542 | 40 | 10.3 | 214439 | 0.81 | 6.37 | 0.0437 | 127.552 | 12.3 |
| 21/4a (0.8) | MAO (80/100) | 3600 | 40 | 10.3 | — | — | 6.37 | 0.0112 | 13.9992 | 1.35 |
| 22/4a (0.8) | MAO (80/100) | 37 | 40.1 | 10.3 | — | — | 6.37 | 0.0026 | 315.875 | 30.6 |
| 23/4a (0.4) | MAO (40/100) | 3601 | 40.1 | 3.45 | 203176 | 1.5 | 6.37 | 0.0165 | 41.2404 | 12.0 |
| 24/4a (0.4) | MAO (40/100) | 3601 | 40 | 3.45 | — | — | 6.37 | 0.0034 | 8.4975 | 2.47 |
| 25/4a (0.4) | MAO (40/100) | 3601 | 40 | 3.45 | — | — | 6.37 | 0.0035 | 8.74745 | 2.54 |
| 26/4a (0.4) | MAO (40/100) | 1940 | 74.9 | 10.3 | 47280 | 5.1 | 6.37 | 0.0508 | 235.637 | 22.8 |
| 27/4a | MAO | — | — | 0 | — | — | 6.37 | — | #DIV/0! | #DIV/0! |

TABLE 2-continued

PPRA evaluation with complexes 4a, 4b, 4c, 4d, 5d and 6d[a].

| Run/Cat (μmol)[a/b] | Activator[c] (μmol/eq.) | Time/s | T/° C. | P/bar[d] | Mw[e] | Wt % Oct | mmol Oct | Yield/g | Activity g/mmol/h | Activity g/mmol/h/bar |
|---|---|---|---|---|---|---|---|---|---|---|
| 28/4a (0.4) | MAO (40/100) | 3600 | 75.1 | 3.45 | — | — | 6.37 | 0.0002 | 0.49995 | 0.145 |
| 29/4a (0.4) | MAO (40/100) | 3601 | 75.1 | 3.45 | — | — | 6.37 | 0.0043 | 10.748 | 3.12 |
| 30/4a (0.4) | MAO (40/100) | 3600 | 75 | 3.45 | 66116 | 2.2 | 6.37 | 0.0107 | 26.7466 | 7.76 |
| 31/4b (0.8) | MAO (80/100) | 2154 | 40 | 17.2 | 351022 | — | 0 | 0.0576 | 120.326 | 6.98 |
| 32/4b (0.8) | MAO (80/100) | 1513 | 40.2 | 17.2 | 294595 | — | 0 | 0.194 | 577.064 | 33.5 |
| 33/4b (0.8) | MAO (80/100) | 1308 | 40.2 | 17.2 | 294980 | — | 0 | 0.0674 | 232.11 | 13.47 |
| 34/4b (0.8) | MAO (80/100) | 1439 | 40 | 10.3 | 298602 | — | 0 | 0.0333 | 104.117 | 10.1 |
| 35/4b (0.8) | MAO (80/100) | 619 | 39.9 | 10.3 | 151305 | — | 0 | 0.0606 | 440.734 | 42.6 |
| 36/4b (0.8) | MAO (80/100) | 825 | 40.1 | 10.3 | 221605 | — | 0 | 0.0171 | 93.3225 | 9.03 |
| 37/4b (0.4) | MAO (40/100) | 3601 | 40.1 | 3.45 | 313066 | — | 0 | 0.0301 | 75.2251 | 21.8 |
| 38/4b (0.4) | MAO (40/100) | 3601 | 40 | 3.45 | 268136 | — | 0 | 0.0201 | 50.2376 | 14.6 |
| 39/4b (0.4) | MAO (40/100) | 3601 | 40.2 | 3.45 | — | — | 0 | 0.0081 | 20.2435 | 5.87 |
| 40/4b (0.8) | MAO (80/100) | 3601 | 75.1 | 17.2 | 55806 | — | 0 | 0.0462 | 57.7386 | 3.35 |
| 41/4b (0.8) | MAO (80/100) | 3602 | 75.1 | 17.2 | — | — | 0 | 0.0144 | 17.9922 | 1.04 |
| 42/4b (0.8) | MAO (80/100) | 3601 | 75 | 17.2 | 25994 | — | 0 | 0.0576 | 71.9794 | 4.18 |
| 43/4b (0.4) | MAO (40/100) | 1008 | 75 | 10.3 | 32688 | — | 0 | 0.0516 | 460.541 | 44.5 |
| 44/4b (0.4) | MAO (40/100) | 931 | 75.1 | 10.3 | 31831 | — | 0 | 0.0503 | 486.371 | 47.0 |
| 45/4b (0.4) | MAO (40/100) | 1186 | 75 | 10.3 | 35202 | — | 0 | 0.0486 | 368.806 | 35.7 |
| 46/4b (0.4) | MAO (40/100) | 3601 | 75.1 | 3.45 | — | — | 0 | 0.0018 | 4.49924 | 1.31 |
| 47/4b (0.4) | MAO (40/100) | 3601 | 75 | 3.45 | — | — | 0 | 0.0017 | 4.24929 | 1.23 |
| 48/4b (0.4) | MAO (40/100) | 2234 | 74.9 | 3.45 | 40479 | — | 0 | 0.05 | 201.4 | 58.4 |
| 49/4b (0.8) | MAO (80/100) | 2166 | 40.1 | 10.3 | 210963 | 1.6 | 6.37 | 0.047 | 97.6639 | 9.45 |
| 50/4b (0.8) | MAO (80/100) | 3600 | 40.1 | 10.3 | — | — | 6.37 | 0.0058 | 7.24909 | 0.70 |
| 51/4b (0.8) | MAO (80/100) | 1179 | 40.1 | 10.3 | 164073 | 2.1 | 6.37 | 0.0414 | 158.031 | 15.3 |
| 52/4b (0.4) | MAO (40/100) | 3601 | 40 | 3.45 | 0 | 2.1 | 6.37 | 0.2441 | 610.091 | 177 |
| 53/4b (0.4) | MAO (40/100) | 3601 | 39.9 | 3.45 | — | — | 6.37 | 0.0016 | 3.99876 | 1.16 |
| 54/4b (0.4) | MAO (40/100) | 3600 | 39.9 | 3.45 | — | — | 6.37 | 0.0051 | 12.7483 | 3.70 |
| 55/4b (0.4) | MAO (40/100) | 1556 | 74.8 | 10.3 | 42989.6 | 6.4 | 6.37 | 0.0512 | 296.079 | 28.6 |
| 56/4b (0.4) | MAO (40/100) | 1943 | 75 | 10.3 | 47539 | 4.3 | 6.37 | 0.0458 | 212.2 | 20.5 |
| 57/4b (0.4) | MAO (40/100) | 1577 | 75 | 0 | 45133 | 6.4 | 6.37 | 0.0432 | 246.472 | 23.8 |
| 58/4b (0.4) | MAO (40/100) | 3601 | 75 | 3.45 | — | — | 6.37 | −0.0003 | −0.74977 | −0.218 |
| 59/4b (0.4) | MAO (40/100) | 3601 | 75.1 | 3.45 | 75445 | 2.4 | 6.37 | 0.0149 | 37.2442 | 10.8 |
| 60/4b (0.4) | MAO (40/100) | 3601 | 75 | 3.45 | 62938 | 3.0 | 6.37 | 0.0144 | 35.9916 | 10.4 |
| 61/4c (0.8) | MAO (80/100) | 3601 | 39.9 | 17.2 | 439232 | — | 0 | 0.0969 | 121.123 | 7.03 |
| 62/4c (0.8) | MAO (80/100) | 131 | 41.2 | 17.2 | 35365 | — | 0 | 0.5529 | 18994.2 | 1102 |
| 63/4c (0.8) | MAO (80/100) | 124 | 40.7 | 17.2 | 35834 | — | 0 | 0.4616 | 16804.5 | 975 |
| 64/4c | MAO | 2722 | 39.9 | 10.3 | 382593 | — | 0 | 0.0404 | 66.7972 | 6.46 |

TABLE 2-continued

PPRA evaluation with complexes 4a, 4b, 4c, 4d, 5d and 6d[a].

| Run/Cat (μmol)[a/b] | Activator[c] (μmol/eq.) | Time/s | T/° C. | P/bar[d] | Mw[e] | Wt % Oct | mmol Oct | Yield/g | Activity g/mmol/h | Activity g/mmol/h/bar |
|---|---|---|---|---|---|---|---|---|---|---|
| (0.8) | (80/100) | | | | | | | | | |
| 65/4c (0.8) | MAO (80/100) | 272 | 40.2 | 10.3 | 36509 | — | 0 | 0.3823 | 6317.15 | 611 |
| 66/4c (0.8) | MAO (80/100) | 58 | 39.9 | 10.3 | 25897 | — | 0 | 0.2121 | 16473.1 | 1593 |
| 67/7a (0.4) | MAO (40/100) | 1608 | 40 | 3.45 | 177533 | — | 0 | 0.0538 | 301.147 | 87.4 |
| 68/4c (0.4) | MAO (40/100) | 3600 | 40.2 | 3.45 | 196172 | — | 0 | 0.0292 | 72.9972 | 21.2 |
| 69/4c (0.4) | MAO (40/100) | 1365 | 40.1 | 3.45 | 214406 | — | 0 | 0.0532 | 350.81 | 101.8 |
| 70/4c (0.8) | MAO (80/100) | 73 | 74.2 | 17.2 | 26460 | — | 0 | 0.5325 | 32897.4 | 1909 |
| 71/4c (0.8) | MAO (80/100) | 3600 | 75 | 17.2 | 112336 | — | 0 | 0.0426 | 53.2472 | 3.09 |
| 72/4c (0.8) | MAO (80/100) | 65 | 74.3 | 17.2 | 21382 | — | 0 | 0.3814 | 26259.2 | 1524 |
| 73/4c (0.4) | MAO (40/100) | 275 | 75 | 10.3 | 30126 | — | 0 | 0.0641 | 2096.6 | 203 |
| 74/4c (0.4) | MAO (40/100) | 278 | 74.9 | 10.3 | 29473 | — | 0 | 0.0596 | 1931.93 | 187 |
| 75/4c (0.4) | MAO (40/100) | 3601 | 75.1 | 3.45 | — | — | 0 | 0.0039 | 9.74626 | 2.83 |
| 76/4c (0.4) | MAO (40/100) | 3600 | 75 | 3.45 | — | — | 0 | 0.0041 | 10.2488 | 2.97 |
| 77/4c (0.4) | MAO (40/100) | 1002 | 75.1 | 3.45 | 51265 | — | 0 | 0.0522 | 468.867 | 136 |
| 78/4c (0.8) | MAO (80/100) | 70 | 39.8 | 10.3 | 43779 | 5.0 | 6.37 | 0.2271 | 14588.9 | 1411 |
| 79/4c (0.8) | MAO (80/100) | 3600 | 40 | 10.3 | — | — | 6.37 | 0.0069 | 8.62469 | 0.834 |
| 80/4c (0.8) | MAO (80/100) | 74 | 39.8 | 10.3 | 47568 | 4.0 | 6.37 | 0.2181 | 13193.3 | 1276 |
| 81/4c (0.4) | MAO (40/100) | 3261 | 40.1 | 3.45 | 166172 | 7.9 | 6.37 | 0.0499 | 137.731 | 40.0 |
| 82/4c (0.4) | MAO (40/100) | 1036 | 40 | 3.45 | 164673 | 0.98 | 6.37 | 0.0583 | 506.374 | 147.0 |
| 83/4c (0.4) | MAO (40/100) | 1465 | 40 | 3.45 | 188109 | 1.1 | 6.37 | 0.0558 | 342.867 | 99.5 |
| 84/4c (0.4) | MAO (40/100) | 396 | 74.9 | 10.3 | 35439 | 11 | 6.37 | 0.0582 | 1323.66 | 128 |
| 85/4c (0.4) | MAO (40/100) | 610 | 75.1 | 10.3 | 39389 | 2.7 | 6.37 | 0.0509 | 751.082 | 72.6 |
| 86/4c (0.4) | MAO (40/100) | 661 | 75.1 | 0 | 36958 | 4.4 | 6.37 | 0.0481 | 655.234 | 63.4 |
| 87/4c (0.4) | MAO (40/100) | 3601 | 75.1 | 3.45 | — | — | 6.37 | −0.0003 | −0.74979 | −0.218 |
| 88/4c (0.4) | MAO (40/100) | 3601 | 75 | 3.45 | 123007 | 1.7 | 6.37 | 0.0355 | 88.7212 | 25.7 |
| 89/4c (0.4) | MAO (40/100) | 3600 | 75 | 3.45 | 122888 | 1.9 | 6.37 | 0.0108 | 26.9969 | 7.83 |
| 90/4d (0.8) | MAO (80/100) | 1620 | 40 | 17.2 | 444313 | — | 0 | 0.0963 | 267.492 | 15.5 |
| 91/4d (0.8) | MAO (80/100) | 547 | 40.6 | 17.2 | 100968 | — | 0 | 0.3361 | 2764.74 | 160 |
| 92/4d (0.8) | MAO (80/100) | 1127 | 40.1 | 17.2 | 259759 | — | 0 | 0.3169 | 1265.49 | 73.4 |
| 93/4d (0.8) | MAO (80/100) | 900 | 40.1 | 10.3 | 344733 | — | 0 | 0.0418 | 208.961 | 20.2 |
| 94/4d (0.8) | MAO (80/100) | 274 | 40.5 | 10.3 | 64093 | — | 0 | 0.1919 | 3157.06 | 305 |
| 95/4d (0.8) | MAO (80/100) | 651 | 39.9 | 10.3 | 291955 | — | 0 | 0.0401 | 277.078 | 26.8 |
| 96/4d (0.4) | MAO (40/100) | 3600 | 40 | 3.45 | 330666 | — | 0 | 0.0388 | 96.9908 | 28.1 |
| 97/4d (0.4) | MAO (40/100) | 3600 | 40.1 | 3.45 | 311026 | — | 0 | 0.0345 | 86.2454 | 25.0 |
| 98/4d (0.4) | MAO (40/100) | 1236 | 40 | 3.45 | 199732 | — | 0 | 0.0562 | 409.24 | 119 |
| 99/4d (0.8) | MAO (80/100) | 897 | 75.1 | 17.2 | 62318 | — | 0 | 0.1096 | 549.906 | 31.9 |
| 100/4d (0.8) | MAO (80/100) | 3600 | 75 | 17.2 | 133644 | — | 0 | 0.0607 | 75.8617 | 4.40 |
| 101/4d | MAO | 260 | 75 | 17.2 | 32656 | — | 0 | 0.194 | 3358.21 | 194.9 |

TABLE 2-continued

PPRA evaluation with complexes 4a, 4b, 4c, 4d, 5d and 6d[a].

| Run/Cat (μmol)[a/b] | Activator[c] (μmol/eq.) | Time/s | T/° C. | P/bar[d] | Mw[e] | Wt % Oct | mmol Oct | Yield/g | Activity g/mmol/h | Activity g/mmol/h/bar |
|---|---|---|---|---|---|---|---|---|---|---|
| (0.8) | (80/100) | | | | | | | | | |
| 102/4d (0.4) | MAO (40/100) | 292 | 75 | 10.3 | 37395 | — | 0 | 0.0526 | 1618.68 | 156.6 |
| 103/4d (0.4) | MAO (40/100) | 446 | 75 | 10.3 | 41474 | — | 0 | 0.0547 | 1103.64 | 107 |
| 104/4d (0.4) | MAO (40/100) | 544 | 75.1 | 10.3 | 43217 | — | 0 | 0.0512 | 846.841 | 81.9 |
| 105/4d (0.4) | MAO (40/100) | 3601 | 75 | 3.45 | — | — | 0 | 0.0051 | 12.7479 | 3.70 |
| 106/4d (0.4) | MAO (40/100) | 3600 | 75 | 3.45 | — | — | 0 | 0.0045 | 11.2499 | 3.26 |
| 107/4d (0.4) | MAO (40/100) | 3601 | 75.1 | 3.45 | 92793 | — | 0 | 0.0381 | 95.2328 | 27.6 |
| 108/4d (0.8) | MAO (80/100) | 560 | 40 | 10.3 | 149627 | 1.7 | 6.37 | 0.0532 | 427.553 | 41.4 |
| 109/4d (0.8) | MAO (80/100) | 3601 | 40 | 10.3 | — | — | 6.37 | 0.0107 | 13.3723 | 1.29 |
| 110/4d (0.8) | MAO (80/100) | 373 | 40.1 | 10.3 | 123533 | 2.7 | 6.37 | 0.0722 | 871.84 | 84.3 |
| 111/4d (0.4) | MAO (40/100) | 3600 | 40 | 3.45 | — | — | 6.37 | 0.0092 | 22.9992 | 6.67 |
| 112/4d (0.4) | MAO (40/100) | 1087 | 40 | 3.45 | 198224 | 1.1 | 6.37 | 0.0608 | 503.538 | 146 |
| 113/4d (0.4) | MAO (40/100) | 1901 | 40.1 | 3.45 | 198591 | 1.1 | 6.37 | 0.0529 | 250.383 | 72.7 |
| 114/4d (0.4) | MAO (40/100) | 683 | 74.9 | 10.3 | 48273 | 4.0 | 6.37 | 0.0495 | 652.747 | 63.1 |
| 115/4d (0.4) | MAO (40/100) | 1165 | 74.9 | 10.3 | 56500 | 3.7 | 6.37 | 0.0492 | 380.05 | 36.8 |
| 116/4d (0.4) | MAO (40/100) | 1682 | 75 | 0 | 66218 | 2.8 | 6.37 | 0.0493 | 263.729 | 25.5 |
| 117/4d (0.4) | MAO (40/100) | 3600 | 75 | 3.45 | — | — | 6.37 | −0.0001 | −0.24997 | −0.0725 |
| 118/4d (0.4) | MAO (40/100) | 3600 | 75.1 | 3.45 | — | — | 6.37 | 0.008 | 19.9984 | 5.80 |
| 119/4d (0.4) | MAO (40/100) | 3600 | 74.9 | 3.45 | — | — | 6.37 | 0.0066 | 16.499 | 4.79 |
| 120/5d (0.8) | MAO (80/100) | 1113 | 39.9 | 17.2 | — | — | 0 | 0.0043 | 17.3809 | 1.01 |
| 121/5d (0.8) | MAO (80/100) | 747 | 40.3 | 17.2 | 105105 | — | 0 | 0.298 | 1795.9 | 104 |
| 122/5d (0.8) | MAO (80/100) | 828 | 40.4 | 17.2 | 161942 | — | 0 | 0.1833 | 995.63 | 57.8 |
| 123/5d (0.8) | MAO (80/100) | 669 | 40 | 10.3 | — | — | 0 | 0.0021 | 14.1163 | 1.37 |
| 124/5d (0.8) | MAO (80/100) | 194 | 40.5 | 10.3 | 73365 | — | 0 | 0.1266 | 2937.81 | 284 |
| 125/5d (0.8) | MAO (80/100) | 623 | 40.3 | 10.3 | — | — | 0 | 0.0066 | 47.6879 | 4.61 |
| 126/5d (0.4) | MAO (40/100) | 3601 | 40 | 3.45 | — | — | 0 | 0.0043 | 10.7461 | 3.12 |
| 127/5d (0.4) | MAO (40/100) | 3601 | 40 | 3.45 | — | — | 0 | 0.0027 | 6.7473 | 1.96 |
| 128/5d (0.4) | MAO (40/100) | 3077 | 40.2 | 3.45 | 221805 | — | 0 | 0.0347 | 101.482 | 29.4 |
| 129/5d (0.8) | MAO (80/100) | 3601 | 75 | 17.2 | 45509 | — | 0 | 0.0681 | 85.0917 | 4.94 |
| 130/5d (0.8) | MAO (80/100) | 3601 | 75 | 17.2 | — | — | 0 | 0.0032 | 3.99863 | 0.23 |
| 131/5d (0.8) | MAO (80/100) | 719 | 75 | 17.2 | 34188 | — | 0 | 0.1394 | 872.887 | 50.7 |
| 132/5d (0.4) | MAO (40/100) | 2139 | 74.9 | 10.3 | 64632 | — | 0 | 0.0371 | 156.1 | 15.1 |
| 133/5d (0.4) | MAO (40/100) | 3601 | 75.1 | 10.3 | 53310 | — | 0 | 0.0265 | 66.2261 | 6.41 |
| 134/5d (0.4) | MAO (40/100) | 3601 | 75 | 10.3 | 55615 | — | 0 | 0.0207 | 51.732 | 5.00 |
| 135/5d (0.4) | MAO (40/100) | 3601 | 75 | 3.45 | — | — | 0 | −0.0003 | −0.74988 | −0.218 |
| 136/5d (0.4) | MAO (40/100) | 3601 | 75 | 3.45 | — | — | 0 | −0.0003 | −0.74988 | −0.218 |
| 137/5d (0.4) | MAO (40/100) | 3600 | 75 | 3.45 | — | — | 0 | 0.0096 | 23.9993 | 6.96 |
| 138/5d | MAO | 422 | 40.1 | 10.3 | 78331 | 2.1 | 6.37 | 0.0485 | 517.303 | 50.0 |

TABLE 2-continued

PPRA evaluation with complexes 4a, 4b, 4c, 4d, 5d and 6d[a].

| Run/Cat (μmol)[a/b] | Activator[c] (μmol/eq.) | Time/s | T/° C. | P/bar[d] | Mw[e] | Wt % Oct | mmol Oct | Yield/g | Activity g/mmol/h | Activity g/mmol/h/bar |
|---|---|---|---|---|---|---|---|---|---|---|
| (0.8) | (80/100) | | | | | | | | | |
| 139/5d (0.8) | MAO (80/100) | 1641 | 40 | 10.3 | — | — | 6.37 | 0.0027 | 7.4047 | 0.716 |
| 140/5d (0.8) | MAO (80/100) | 273 | 39.9 | 10.3 | 85760 | 2.7 | 6.37 | 0.0546 | 899.374 | 87.0 |
| 141/5d (0.4) | MAO (40/100) | 3601 | 40.1 | 3.45 | — | — | 6.37 | 0.0018 | 4.49859 | 1.31 |
| 142/5d (0.4) | MAO (40/100) | 1531 | 40.1 | 3.45 | 173593 | 1.3 | 6.37 | 0.0499 | 293.386 | 85.1 |
| 143/5d (0.4) | MAO (40/100) | 3552 | 40.1 | 3.45 | 213602 | 1.2 | 6.37 | 0.0415 | 105.147 | 30.5 |
| 144/5d (0.4) | MAO (40/100) | 3601 | 74.9 | 10.3 | 75489 | 4.5 | 6.37 | 0.0203 | 50.7373 | 4.91 |
| 145/5d (0.4) | MAO (40/100) | 3600 | 75 | 10.3 | 71002 | 2.6 | 6.37 | 0.0206 | 51.4973 | 4.98 |
| 146/5d (0.4) | MAO (40/100) | 3602 | 75 | 0 | — | — | 6.37 | 0.0096 | 23.9894 | 2.32 |
| 147/5d (0.4) | MAO (40/100) | 3600 | 75.1 | 3.45 | — | — | 6.37 | −0.0004 | −0.99991 | −0.290 |
| 148/5d (0.4) | MAO (40/100) | 3601 | 75.1 | 3.45 | — | — | 6.37 | 0.0025 | 6.24908 | 1.81 |
| 149/5d (0.4) | MAO (40/100) | 3601 | 75 | 3.45 | — | — | 6.37 | 0.002 | 4.99917 | 1.45 |
| 150/6d (0.8) | MAO (80/100) | 907 | 40 | 17.2 | — | — | 0 | 0.0043 | 21.3374 | 1.24 |
| 151/6d (0.8) | MAO (80/100) | 933 | 40.4 | 17.2 | 134945 | — | 0 | 0.0561 | 270.576 | 15.7 |
| 152/6d (0.8) | MAO (80/100) | 613 | 40.4 | 17.2 | 86118 | — | 0 | 0.0242 | 177.755 | 10.3 |
| 153/6d (0.8) | MAO (80/100) | 1611 | 40 | 10.3 | — | — | 0 | 0.0016 | 4.46697 | 0.432 |
| 154/6d (0.8) | MAO (80/100) | 455 | 40.3 | 10.3 | 87342 | — | 0 | 0.0661 | 653.607 | 63.2 |
| 155/6d (0.8) | MAO (80/100) | 482 | 40.2 | 10.3 | — | — | 0 | 0.004 | 37.356 | 3.61 |
| 156/6d (0.4) | MAO (40/100) | 3600 | 40.1 | 3.45 | — | — | 0 | 0.0068 | 16.9981 | 4.93 |
| 157/6d (0.4) | MAO (40/100) | 3601 | 40.1 | 3.45 | — | — | 0 | 0.0042 | 10.4969 | 3.05 |
| 158/6d (0.4) | MAO (40/100) | 3600 | 40.1 | 3.45 | — | — | 0 | 0.0007 | 1.74991 | 0.508 |
| 159/6d (0.8) | MAO (80/100) | 3601 | 75.1 | 17.2 | — | — | 0 | 0.0128 | 15.9958 | 0.928 |
| 160/6d (0.8) | MAO (80/100) | 3601 | 74.9 | 17.2 | — | — | 0 | 0.0075 | 9.37172 | 0.544 |
| 161/6d (0.8) | MAO (80/100) | 2258 | 75 | 17.2 | 37145 | — | 0 | 0.0946 | 188.564 | 10.9 |
| 162/6d (0.4) | MAO (40/100) | 1333 | 75 | 10.3 | 45405 | — | 0 | 0.034 | 229.563 | 22.2 |
| 163/6d (0.4) | MAO (40/100) | 2139 | 75 | 10.3 | 48400 | — | 0 | 0.0433 | 182.222 | 17.6 |
| 164/6d (0.4) | MAO (40/100) | 3601 | 74.9 | 10.3 | 53529 | — | 0 | 0.0275 | 68.7374 | 6.65 |
| 165/6d (0.4) | MAO (40/100) | 3601 | 75 | 3.45 | — | — | 0 | −0.0001 | −0.24996 | −0.0725 |
| 166/6d (0.4) | MAO (40/100) | 3601 | 75.1 | 3.45 | — | — | 0 | −0.0004 | −0.99974 | −0.290 |
| 167/6d (0.4) | MAO (40/100) | 3601 | 75 | 3.45 | 51320 | — | 0 | 0.0104 | 25.9922 | 7.54 |
| 168/6d (0.8) | MAO (80/100) | 1548 | 40.2 | 10.3 | 72379 | 2.9 | 6.37 | 0.0403 | 117.127 | 11.3 |
| 169/6d (0.8) | MAO (80/100) | 1652 | 40.2 | 10.3 | — | — | 6.37 | 0.0018 | 4.90353 | 0.474 |
| 170/6d (0.8) | MAO (80/100) | 1186 | 40.2 | 10.3 | 97895 | 3.0 | 6.37 | 0.0289 | 109.676 | 10.61 |
| 171/6d (0.4) | MAO (40/100) | 3600 | 40 | 3.45 | — | — | 6.37 | 0.0015 | 3.74957 | 1.09 |
| 172/6d (0.4) | MAO (40/100) | 3600 | 40.3 | 3.45 | 140824 | 2.0 | 6.37 | 0.033 | 82.4897 | 23.9 |
| 173/6d (0.4) | MAO (40/100) | 3601 | 40 | 3.45 | — | — | 6.37 | 0.0015 | 3.74873 | 1.09 |
| 174/6d (0.4) | MAO (40/100) | 3601 | 75 | 10.3 | 61954 | 5.8 | 6.37 | 0.023 | 57.481 | 5.56 |
| 175/6d | MAO | 3601 | 75 | 10.3 | — | — | 6.37 | 0.0097 | 24.2427 | 2.34 |

TABLE 2-continued

PPRA evaluation with complexes 4a, 4b, 4c, 4d, 5d and 6d[a].

| Run/Cat (μmol)[a/b] | Activator[c] (μmol/eq.) | Time/s | T/° C. | P/bar[d] | Mw[e] | Wt % Oct | mmol Oct | Yield/g | Activity g/mmol/h | Activity g/mmol/h/bar |
|---|---|---|---|---|---|---|---|---|---|---|
| (0.4) 176/6d (0.4) | (40/100) MAO (40/100) | 3601 | 74.9 | 0 | — | — | 6.37 | −0.024 | −59.9897 | −5.80 |
| 177/6d (0.4) | MAO (40/100) | 3601 | 74.9 | 3.45 | — | — | 6.37 | −0.0005 | −1.2497 | −0.363 |
| 178/6d (0.4) | MAO (40/100) | 3600 | 75 | 3.45 | — | — | 6.37 | 0.0011 | 2.74985 | 0.80 |
| 179/6d (0.4) | MAO (40/100) | 3601 | 75.1 | 3.45 | — | — | 6.37 | 0.0017 | 4.2484 | 1.23 |

[a]General Conditions: Toluene solvent, ethylene (50-250 psig), reaction quenched with a 5 mol % Oxygen in Argon after the total duration of one hour or a predetermined amount of ethylene had been consumed (20 psig);
[b]General Conditions: Toluene solvent, ethylene (50-250 psig), octene (6.37 mmol), reaction quenched with 5 mol % Oxygen in Argon after the total duration of one hour or a predetermined amount of ethylene had been consumed (20 psig);
[c]MAO = methylaluminoxane;
[d]1 bar = 100 KPa = 14.508 psi;
[e]Determined by GPC at 135° C. Validated with the literature precedent complexes [2,6-i-PrC$_6$H$_3$N=C(Me)—C(Me)=N2,6-i-PrC$_6$H$_3$]NiBr$_2$ and [2,6-(2',6',-i-PrC$_6$H$_3$N)$_2$C$_5$H$_3$N]FeCl$_2$ complexes and MAO as activator.

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

We claim:

1. A process to polymerize or oligomerize an unsaturated monomer comprising contacting the monomer with a transition metal catalyst compound represented by the formula:

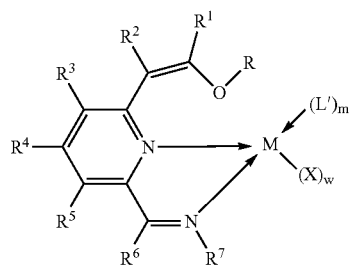

wherein
M is a group 4, 5, 6, 7, 8, 9, 10, or 11 transition metal;
N is nitrogen;
O is oxygen;
each X is, independently, an anionic monodentate ligand;
w is 1, 2 or 3;
each R is, independently, a hydrogen, a hydrocarbyl, a substituted hydrocarbyl, a halocarbyl, or a substituted halocarbyl;
each $R^1$ and $R^2$ is, independently, selected from the group consisting of hydrogen, methyl, ethyl, propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, $CF_3$, $NO_2$, t-butyl, i-propyl, naphthyl, and fluoride, or may join together to form a cyclic or polycyclic ring structure;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl
each $R^7$ is, independently, a hydrocarbyl, a substituted hydrocarbyl, a halocarbyl, or a substituted halocarbyl;
each L' is a neutral ligand bonded to M; and
m is 0 or 1.

2. A process to polymerize or oligomerize an unsaturated monomer comprising contacting the monomer with a transition metal catalyst compound represented by the formula:

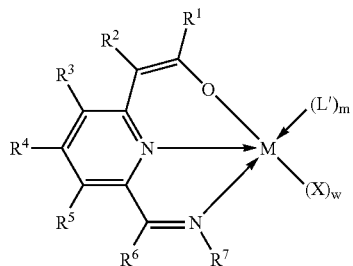

wherein
M is a group 4, 5, 6, 7, 8, 9, 10, or 11 transition metal;
N is nitrogen;
O is oxygen;
each X is, independently, an anionic monodentate ligand;
w is 1, 2 or 3;
each $R^1$ and $R^2$ is, independently, selected from the group consisting of hydrogen, methyl, ethyl, propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, $CF_3$, $NO_2$, t-butyl, i-propyl, naphthyl, and fluoride, or may join together to form a cyclic or polycyclic ring structure;

each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;

each $R^6$ is, independently, a hydrogen, a $C_3$ to $C_{50}$ hydrocarbyl or a $C_3$ to $C_{50}$ halocarbyl;

each $R^7$ is, independently, a hydrocarbyl, a substituted hydrocarbyl, a halocarbyl, or a substituted halocarbyl;

L' is a neutral ligand bonded to M; and

M is 0, 1 or 2.

3. A process to polymerize or oligomerize an unsaturated monomer comprising contacting the monomer with a transition metal catalyst compound represented by the formula:

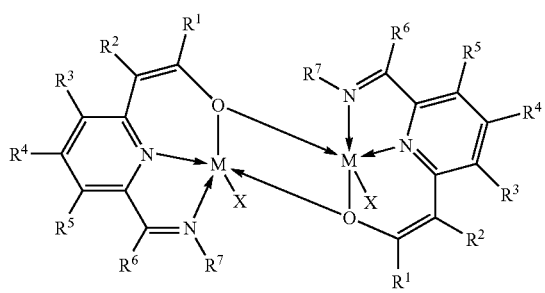

wherein
each M is, independently, a group 4, 5, 6, 7, 8, 9, 10, or 11 transition metal;
N is nitrogen;
O is oxygen;
each X is, independently, a hydride, hydrocarbyl, substituted hydrocarbyl, halocarbyl, substituted halocarbyl;
each $R^1$ and $R^2$ is, independently, selected from the group consisting of hydrogen, methyl, ethyl, propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, $CF_3$, $NO_2$, t-butyl, i-propyl, naphthyl, and fluoride, or may join together to form a cyclic or polycyclic ring structure;

each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;

each $R^6$ is, independently, a hydrogen, a $C_3$ to $C_{50}$ hydrocarbyl or a $C_3$ to $C_{50}$ halocarbyl; and and each $R^7$ is, independently, a hydrocarbyl, a substituted hydrocarbyl, a halocarbyl, or a substituted halocarbyl.

4. A process to polymerize or oligomerize an unsaturated monomer comprising contacting the monomer with a transition metal catalyst compound represented by the formula:

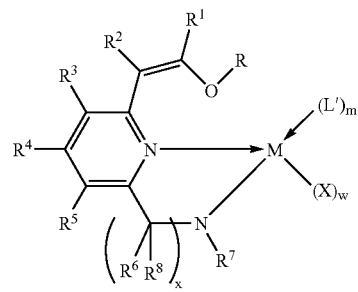

wherein
M is a group 4, 5, 6, 7, 8, 9, 10, or 11 transition metal;
N is nitrogen;
O is oxygen;
each X is, independently, an anionic monodentate ligand;
w is 1, 2 or 3;
each R is, independently, a hydrogen, a hydrocarbyl, a substituted hydrocarbyl, a halocarbyl, or a substituted halocarbyl;
each $R^1$ and $R^2$ is, independently, selected from the group consisting of hydrogen, methyl, ethyl, propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, $CF_3$, $NO_2$, t-butyl, i-propyl, naphthyl, and fluoride, or may join together to form a cyclic or polycyclic ring structure;

each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;

each $R^6$ is, independently, a hydrogen, a $C_3$ to $C_{50}$ hydrocarbyl or a $C_3$ to $C_{50}$ halocarbyl;

each $R^7$ is, independently, a hydrocarbyl, a substituted hydrocarbyl, a halocarbyl, or a substituted halocarbyl;

each $R^8$ is, independently, a hydrogen, a $C_3$ to $C_{50}$ hydrocarbyl or a $C_3$ to $C_{50}$ halocarbyl;

each x is, independently, 1, 2, 3 or 4;

L' is a neutral ligand bonded to M; and m is 0, 1 or 2.

5. A process to polymerize or oligomerize an unsaturated monomer comprising contacting the monomer with a transition metal catalyst compound represented by the formula:

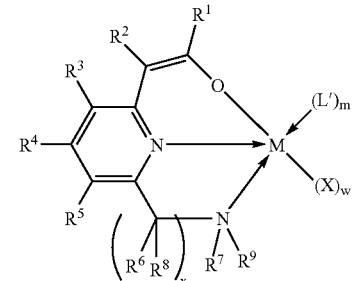

wherein
M is a group 4, 5, 6, 7, 8, 9, 10. or 11 transition metal;
N is nitrogen;
O is oxygen;
each X is, independently, an anionic monodentate ligand;
w is 1, 2 or 3;
each $R^1$ and $R^2$ is, independently, selected from the group consisting of hydrogen, methyl, ethyl, propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, $CF_3$, $NO_2$, t-butyl, i-propyl, naphthyl, and fluoride, or may join together to form a cyclic or polycyclic ring structure;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl, a halocarbyl, or a substituted halocarbyl;
each $R^8$ is, independently, a hydrogen, a $C_3$ to $C_{50}$ hydrocarbyl or a $C_3$ to $C_{50}$ halocarbyl;
x is 1, 2, 3 or 4;
each $R^9$ is, independently, a hydrocarbyl, a substituted hydrocarbyl, a halocarbyl, or a substituted halocarbyl;
L' is a neutral ligand bonded to M; and
m is 0, 1 or 2.

6. A process to polymerize or oligomerize an unsaturated monomer comprising contacting the monomer with a transition metal catalyst compound represented by the formula:

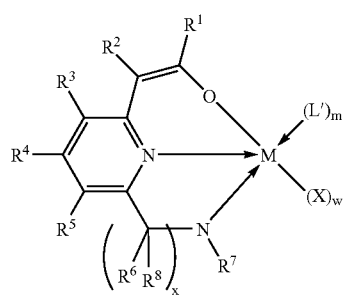

wherein
M is a group 4, 5 or 6 transition metal;
N is nitrogen;
O is oxygen;
each X is, independently, an anionic monodentate ligand;
w is 1, 2 or 3;
each $R^1$ and $R^2$ is, independently, selected from the group consisting of hydrogen, methyl, ethyl, propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, $CF_3$, $NO_2$, t-butyl, i-propyl, naphthyl, and fluoride, or may join together to form a cyclic or polycyclic ring structure;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl. a halocarbyl, or a substituted halocarbyl;
each $R^8$ is independently, a hydrogen, a $C_3$ to $C_{50}$ hydrocarbyl or a $C_3$ to $C_{50}$ halocarbyl;
x is 1, 2, 3 or 4;
L' is a neutral ligand bonded to M; and
m is 0, 1 or 2.

7. A process to polymerize or oligomerize an unsaturated monomer comprising contacting the monomer with a transition metal catalyst compound represented by the formula:

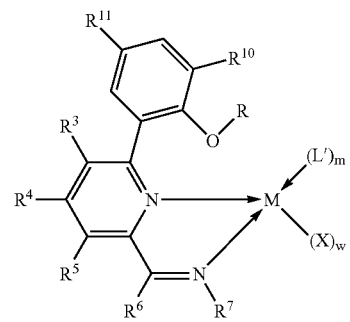

wherein:
each M is, independently, a group 4, 5, 6, 7, 8, 9, 10, or 11 transition metal;
N is nitrogen;
O is oxygen;
each X is, independently, an anionic monodentate ligand;
w is 1, 2 or 3;
each R is, independently, a hydrogen, a hydrocarbyl, a substituted hydrocarbyl, a halocarbyl, or a substituted halocarbyl;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl, a halocarbyl, or a substituted halocarbyl:
each $R^{10}$ is, independently, a hydrocarbyl, a substituted hydrocarbyl, a halocarbyl, or a substituted halocarbyl;
each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group;
L' is a neutral ligand bonded to M; and
m is 0, 1 or 2.

8. A process to polymerize or oligomerize an unsaturated monomer comprising contacting the monomer with a transition metal catalyst compound represented by the formula:

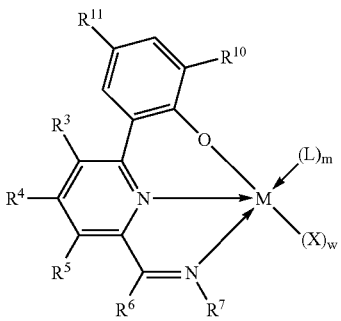

wherein
- M is a group 4, 5, 6. 7, 8, 9, 10, or 11 transition metal;
- N is nitrogen;
- O is oxygen;
- each X is, independently, an anionic monodentate ligand;
- w is 1, 2 or 3;
- each $R^3$, $R^4$, $R^5$ is, independently, a hydrogen, a hydrocarbyl, a substituted hydrocarbyl, a halocarbyl, or a substituted halocarbyl, or independently, may join together to form a cyclic or polycyclic ring structure;
- each $R^6$ is, independently, a hydrogen, a $C_3$ to $C_{50}$ hydrocarbyl or a $C_3$ to $C_{50}$ halocarbyl;
- each $R^7$ is, independently, a hydrocarbyl, a substituted hydrocarbyl, a halocarbyl, or a substituted halocarbyl;
- each $R^{10}$ is, independently, a hydrocarbyl, a substituted hydrocarbyl, a halocarbyl, or a substituted halocarbyl;
- each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group;
- L' is a neutral ligand bonded to M; and
- m is 0, 1 or 2.

9. A process to polymerize or oligomerize an unsaturated monomer comprising contacting the monomer with a transition metal catalyst compound represented by the formula:

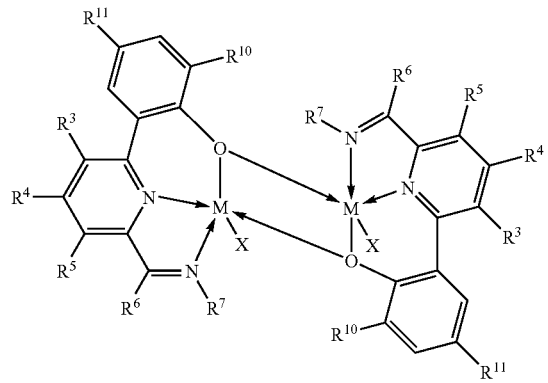

wherein
- each M is, independently, a group 4, 5, 6, 7, 8, 9, 10, or 11 transition metal;
- N is nitrogen;
- O is oxygen;
- each X is, independently, a hydride, hydrocarbyl, substituted hydrocarbyl, halocarbyl, substituted halocarbyl;
- w is 1, 2 or 3;
- each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
- each $R^6$ is, independently, a hydrogen, a $C_3$ to $C_{50}$ hydrocarbyl or a $C_3$ to $C_{50}$ halocarbyl;
- each $R^7$ is, independently, a hydrocarbyl, a substituted hydrocarbyl, a halocarbyl, or a substituted halocarbyl;
- each $R^{10}$ is, independently, a hydrocarbyl, a substituted hydrocarbyl, a halocarbyl, or a substituted halocarbyl; and
- each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group.

10. A process to polymerize or oligomerize an unsaturated monomer comprising contacting the monomer with a transition metal catalyst compound represented by the formula:

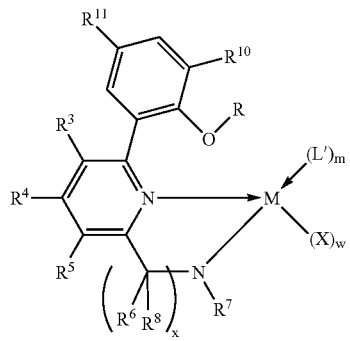

wherein
- M is a group 4, 5. 6, 7. 8 9, 10 or 11 transition metal;
- N is nitrogen;
- O is oxygen;
- each X is, independently, a hydride, hydrocarbyl, substituted hydrocarbyl, halocarbyl, substituted halocarbyl;
- w is 1, 2 or 3;
- each R is, independently, a hydrogen, a hydrocarbyl, a substituted hydrocarbyl, a halocarbyl, or a substituted halocarbyl;
- each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
- each $R^6$ is, independently, a hydrogen, a $C_3$ to $C_{50}$ hydrocarbyl or a $C_3$ to $C_{50}$ halocarbyl;
- each $R^7$ is, independently, a hydrocarbyl, a substituted hydrocarbyl, a halocarbyl, or a substituted halocarbyl;
- each $R^8$ is, independently, a hydrogen, a $C_3$ to $C_{50}$ hydrocarbyl or a $C_3$ to $C_{50}$ halocarbyl;
- each $R^{10}$ is, independently, a hydrocarbyl, a substituted hydrocarbyl, a halocarbyl, or a substituted halocarbyl;
- each $R^{11}$ is, independently, a hydrocarbyl, a substituted hydrocarbyl, a halocarbyl, a substituted halocarbyl or an electron withdrawing group selected from $NO_2$, sulfonate, halo, carboxyl, sulfonyl ester, a carboxylic ester group, or a perfluoroalkyl group;
- x is 1, 2, 3 or 4;
- L' is a neutral ligand bonded to M; and
- m is 0, 1 or 2.

11. A process to polymerize or oligomerize an unsaturated monomer comprising contacting the monomer with a transition metal catalyst compound represented by the formula:

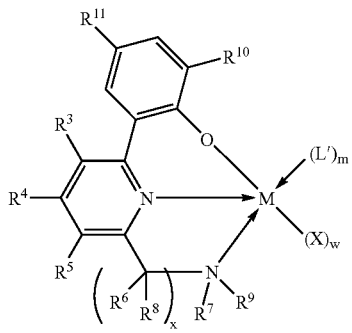

wherein:
M is a group 4, 5, 6, 7, 8 9, 10 or 11 transition metal;
N is nitrogen;
O is oxygen;
each X is, independently, a hydride, hydrocarbyl, substituted hydrocarbyl, halocarbyl, substituted halocarbyl;
w is 1, 2 or 3;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl, a halocarbyl, or a substituted halocarbyl;
each $R^8$ is, independently, a hydrogen, a $C_3$ to $C_{50}$ hydrocarbyl or a $C_3$ to $C_{50}$ halocarbyl;
each $R^9$ is, independently, a hydrocarbyl, a substituted hydrocarbyl, a halocarbyl, or a substituted halocarbyl;
each $R^{10}$ is, independently, a hydrocarbyl, a substituted hydrocarbyl, a halocarbyl, or a substituted halocarbyl;
each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group;
x is 1, 2, 3 or 4;
L' is a neutral ligand bonded to M; and
m is 0, 1 or 2.

12. A process to polymerize or oligomerize an unsaturated monomer comprising contacting the monomer with a transition metal catalyst compound represented by the formula:

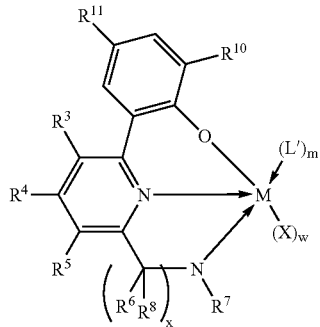

wherein
M is a group 4, 5 or 6 transition metal;
N is nitrogen;
O is oxygen;
each X is, independently, a hydride, hydrocarbyl, substituted hydrocarbyl, halocarbyl, substituted halocarbyl;
w is 1, 2 or 3;
each $R^3$, $R^4$, $R^5$, is, independently, a hydrogen, a hydrocarbyl, a substituted hydrocarbyl, a halocarbyl, or a substituted halocarbyl, or independently, may join together to form a cyclic or polycyclic ring structure;
each $R^6$ is, independently, a hydrogen, a $C_3$ to $C_{50}$ hydrocarbyl or a $C_3$ to $C_{50}$ halocarbyl;
each $R^7$ is, independently, a hydrocarbyl, a substituted hydrocarbyl, a halocarbyl, or a substituted halocarbyl;
each $R^8$ is, independently, a hydrogen, a $C_3$ to $C_{50}$ hydrocarbyl or a $C_3$ to $C_{50}$ halocarbyl;
each $R^{10}$ is, independently, a hydrocarbyl, a substituted hydrocarbyl, a halocarbyl, or a substituted halocarbyl;
each $R^{11}$ is, independently, a hydrocarbyl, a substituted hydrocarbyl, a halocarbyl, a substituted halocarbyl or a group selected from $NO_2$, sulfonate, halo, carboxyl, sulfonyl ester, a carboxylic ester group, or a perfluoroalkyl group;
x is 1, 2, 3 or 4;
L' is a neutral ligand bonded to M; and
m is 0, 1 or 2.

13. The process of claim 6 wherein M is titanium, zirconium or hafnium.

14. The process of claim 1 wherein L' is selected from the group consisting of acetonitrile, diethyl ether, tetrahydrofuran, dimethylaniline, trimethylamine, tributylamine, trimethylphosphine, triphenylphosphine, lithium chloride, ethylene, propylene, butene, octene, and styrene.

15. The process of claim 2 where w is equal to 1 and X is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, and allyl.

16. The process of claim 1 further comprising an activator.
17. The process of claim 2 further comprising an activator.
18. The process of claim 3 further comprising an activator.
19. The process of claim 4 further comprising an activator.
20. The process of claim 5 further comprising an activator.
21. The process of 6 further comprising an activator.
22. The process of 7 further comprising an activator.
23. The process of claim 8 further comprising an activator.
24. The process of claim 8 further comprising an activator.
25. The process of claim 9 further comprising an activator.
26. The process of claim 10 further comprising an activator.
27. The process of claim 11 further comprising an activator.
28. The process of claim 12 further comprising an activator.
29. The process of claim 16 wherein the activator comprises an alumoxane.
30. The process of claim 1 wherein the transition metal catalyst compound is present on a support.
31. The process of claim 30 wherein the support is silica.
32. The process of claim 1 wherein each $R^1$ and $R^2$ is, independently, selected from the group consisting of cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, and naphthyl.

33. The process of claim 2 wherein each $R^1$ and $R^2$ is, independently, selected from the group consisting of cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, and naphthyl.

34. The process of claim 3 wherein each $R^1$ and $R^2$ is, independently, selected from the group consisting of cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, and naphthyl.

35. The process of claim 4 wherein each $R^1$ and $R^2$ is, independently, selected from the group consisting of cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, and naphthyl.

36. The process of claim 5 wherein each $R^1$ and $R^2$ is, independently, selected from the group consisting of cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, and naphthyl.

37. The process of claim 6 wherein each $R^1$ and $R^2$ is, independently, selected from the group consisting of cyclohexyl, cyclopentyl, cycloheptyl, cyclooctyl, cyclodecyl, cyclododecyl, naphthyl, phenyl, tolyl, benzyl, phenethyl, dimethylphenyl, diethylphenyl, anthracenyl, adamantyl, norbornyl, and naphthyl.

* * * * *